US006440696B1

(12) United States Patent
Band et al.

(10) Patent No.: US 6,440,696 B1
(45) Date of Patent: Aug. 27, 2002

(54) E6 TARGETED PROTEIN (E6TP1)

(75) Inventors: Vimla Band, Waban; Qingshen Gao, Winchester, both of MA (US)

(73) Assignee: New England Medical Center, Boston, MA (US)

( * ) Notice: Subject to any disclaimer, the term of this patent is extended or adjusted under 35 U.S.C. 154(b) by 0 days.

(21) Appl. No.: 09/362,336

(22) Filed: Jul. 28, 1999

(51) Int. Cl.$^7$ ............... C12N 15/00; C12N 15/63; C12N 5/00; C07H 21/04

(52) U.S. Cl. ............ 435/69.1; 435/320.1; 435/325; 536/23.5

(58) Field of Search ............... 536/23.1, 23.5; 514/44; 435/320.1, 325, 69.1

(56) References Cited

PUBLICATIONS

J Rudinger, Peptide Hormones, "Characteristics of the amino acids as components of a peptide hormone sequence," Jun. 1976, pp. 1–7.*
TM Clay et al., Pathology Oncology Res., "Potential Use of T Cell Receptor Genes to Modify Hematopoietic Stem Cells for the Gene Therapy of Cancer," 1999, vol. 5, No. 1, 3–11.*
IM Verma et al., Nature, "Gene therapy–promises, problems and prospects," Sep. 1997, vol. 389, pp. 239–242.*
WF Anderson, Nature, "Human gene therapy," Apr. 1998, vol. 392, Supp., pp. 25–30.*
M. Takeuchi et al., Database GenEmbl., Accession No. AF026504, Oct. 1997.*
Altschuler and Ribeiro–Neto, "Mitogenic and oncogenic properties of the small G protein Rap1b." Proc. Natl. Acad. Sci. USA 95: 7475–7479 (1998).
Band et al., "Loss of p53 protein in human papillomavirus type 16 E6–immortalized human mammary epithelial cells." Journal of virology 65(12): 6671–6676 (1991).
Cao et al., "Abrogation of Wild–type p53–mediated trans-activation is insufficient for mutant p53–induced immortalization of normal human mammary epithelial cells." Cancer Research 57: 5584–5589 (1997).
Chen et al., "Interaction of Papillomavirus E6 Oncoproteins with a Putative Calcium–Binding Protein." Scient 269: 529–531 (1995).
Dalal et al., "Mutational Analysis of Human Papillomavirus Type 16 E6 Demonstrates that p53 Degradation IS Necessary for Immortalization of Mammary Epithelial Cell." Journal of Virology 70(2): 683–688 (1996).
Gao et al., "Mutant p53–induced Immortalization of Primary Human Mammary Epithelial Cells." Cancer Research 56: 3129–3133 (1996).
Hattori et al., "Molecular Cloning of a Novel Mitogen–Inducible Nuclear Protein with a Ran GTPase–Activating Domain That Affects Cell Cycle Progression." Molecular and Cellular Biology 15(1): 552–560 (1995).

Huibregrtse et al., "Cloning and Expression of the CDNA for E6–AP, a Protein That Mediates the Interaction of the Human Papillomavirus E6 Oncoprotein with p53." Molecular and Cellular Biology 775–784 (1993).
Huibregtse et al., "A cellular protein mediates association of p53 with the E6 oncoprotein of human papillomavirus types 16 or 18." EMBO Journal 10(13): 4129–4135 (1991).
Kiyono et al., "Binding of high–risk human papillomavirus E6 oncoproteins to the human homologue of the Drosophila discs large tumor suppressor protein." Proc. Natl. Acad. Sci. USA 94: 11612–11616 (1997).
Kiyono et al., "Both Rb/p161NK4a inactivation and telomerase activity are required to immortalize human epithelial cells." Nature 396: 84–88 (1998).
Kobayachi et al., "Transgenic rescue from embryonic lethality and renal carcinogenesis in the Eker rat model by introduction of a wild–type Tsc2 gene." Proc. Natl. Acad. Sci. USA 94: 3990–3993 (1997).
Kuhne and Banks, "E3–Ubiquitin Ligase/E6–AP Links Multicopy Maintenance Protein 7 to the Ubiquitination Pathway by a Novel Motif, the L2G Box." The Journal of Biological Chemistry 273(51): 34302–34309 (1998).
Kurachi et al., "Human SPA–1 Gene Product Selectivity Expressed in Lymphoid Tissues Is a Specific GTPase–activating Protein for Rap1 and Rap2." 272(44) 28081–28088 (1997).
Lee et al., "Binding of human virus oncoproteins to hD1g/SAP97, a mammalian homolog of the Drosophila discs large tumor suppressor proteins." Proc. Natl. Acad. Sci. USA 94: 6670–6675 (1997).
Maki et al., "In Vivo Ubiquitination and Proteasome–mediated Degradation of p53." Cancer Research 56: 2649–2654 (1996).
Menon et al., "Frequent loss of chromosome 14 in atypical and malignant meningioma: identification of a putative 'tumor progression' locus." Oncogene 14: 611–616 (1997).
Munger et al., "Complex formation of human papillomavirus E7 proteins with the retinoblastoma tumor suppressor gene product." EMBO Journal 8(13): 4099–4105 (1989).
Munger et al., "The E6 and E7 Genes of the Human Papillomavirus Type 16 Together Are Necessary and Sufficient for Transformation of Primary Human Keratinocytes." Journal of Virology 4417–4421 (1989).

(List continued on next page.)

Primary Examiner—Dave T. Nguyen
Assistant Examiner—Ram R. Shukla
(74) Attorney, Agent, or Firm—Ingrid A. Beattie; Mintz Levin Cohn Ferris Glovsky & Popeo, P.C

(57) ABSTRACT

The invention relates to a putative human tumor suppressor protein identified as a novel GAP protein, designated "E6TP1" (for E6–targeted protein), its nucleic acid and amino acid sequences, and methods of use thereof in the regulation of small G protein signaling pathways. In addition, methods of use of E6TP1 as a Therapeutic for treatment or prevention of carcinomas, especially HPV-associated carcinomas of anogenital origin, and other diseases is encompassed in the invention.

19 Claims, 12 Drawing Sheets

OTHER PUBLICATIONS

Nellist et al., "Identification and Characterization of the Tuberous Sclerosis Gene on Chromosome 16." Cell 75: 1305–1315 (1993).

Polakis et al., "Phosphorylation of rap1GAP in Vivo and by cAMP–dependent Kinase and the Cell Cycle p34cdc2 Kinase in Vitro." The Journal of Biological Chemistry 267(15): 10780–10785 (1992).

Ronco et al., "Human paillomavirus 16 E6 oncoprotein binds to interferon regulatory factor–3 and inhibits its transcriptional activity." Genes & Development 12: 2061–2072 (1998).

Rubinfeld et al., "Localization of the rap1GAP Catalytic Domain and Sites of Phosphorylation by Mutational Analysis." Molecular and Cellular Biology 12(10): 4634–4642 (1992).

Rubinfeld et al., "Molecular Cloning of a GTPase Activating Protein Specific for the Krev–1 Protein P21rap1." 65: 1033–1042 (1991).

Scheffner et al., "The HPV–16 E6 and E6–AP Complex Functions as a Ubiquitin–Protein Ligase in the Ubiquitination of p53." Call 75: 495–505 (1993).

Simon et al, "Allelic Losses on Chromosomes 14, 10,and 1 in Atypical and Malignant Meningiomas: A Genetic Model of Meningioma Progression." Cancer Research 55: 4696–4701 (1995).

Thomas and Banks, "Inhibition of Bak–induced apoptosis by HPV–18 E6." Oncogene 2943–2954 (1998).

Tong and Howley, "The bovine paillomavirus E6 oncoprotein interacts with paxillin and disrupts the actin cytoskeleton." Proc. Natl. Acad. Sci. USA 94: 4412–4417 (1997).

Tse et al., "Loss of Heterozygosity of Chromosome 14q in Low– and High–Grade Meningiomas." Human Pathology 28(7): 779–785 (1997).

Vossler et al., "cAmP Activates MAP Kinase and Elk–1 through a B–Raf– and Rap1—Dependent Pathway." 89: 1–22 (1997).

Wazer et al., "Immortalization of distinct human mammary epithelial cell types by human papilloma virus 16 E6 or E7." Proc. Natl. Acad. Sci. USA 92: 3687–3691 (1995).

Weinecke et al., "Identification of Tuberin, the Tuberous Sclerosis–2 Product." The Journal of Biological Chemistry 270(27): 16409–16414 (1995).

Xiao et al., "The Tuberous Sclerosis 2 Gene Product, Tuberin, Functions as Rab5 GTPase Acivating Protein (GAP) in Modulating Endocytosis." The Journal of Biological Chemistry 272: 6097–6100, 1997.

Yeung et al., "Predisposition to renal carninoma in the Eker rat is determined by germ–line mutation of the tuberous sclerosis 2 (TSC2) gene." Proc. Natl. 91: 11413–11416 (1994).

Yoshida et al., "Microinjection of smg/rap1/Krev–1 p21 into Swiss 3T3 Cells Induces DNA Synthesis and Morphological Changes." Molecular and Cellular Biology 12(8): 3407–3414 (1992).

Gao et al., "The E6 Oncoproteins of High–risk Papilloma Viruses Bind to Novel Putative GAP Protein, E6TP1, and Target it for Degradation" Abstract; *Proc. Cellular Targets of Viral Carcinogenesis*; Sep. 24–28, 1998.

Gao et al., "The E6 Oncoproteins of High–risk Papilloma Viruses Bind to a Novel Putative GAP Protein, E6TP1, and Target it for Degradation" Abstract; $17^{th}$ *International Papillomavirus Conference*, Jan. 9–15, 1999.

Band, "Molecular Mechanisms of Human Mammary Epithelial Cell Transformation" Abstract, *American Association for Cancer Research* Apr. 10–14, 1999.

Band, "Molecular Mechanisms of Mammary Epithelial Cell Immortalization" Abstract *FASEB J– Biochemistry & Molecular Biology '99*; May 16–20, 1999.

Gao et al., "The E6 Oncoproteins of high–Risk Papillomaviruses Bind to a Novel Putative GAP Protein, E6TP1, and Target It for Degradation" Mol. Cell. Biol. 19(1); 733–744 (1999).

* cited by examiner

```
  1 MTSLKRSQTERPLATDRASVVGTDGTPKVHTDDFYMRRFRSQNGSLGSSV
 51 MAPVGPPRSEGSHHITSTPGVPKMGVRARIADWPPRKENIKESSRSSQEI
101 ETSSCLDSLSSKSSPVSQGSSVSLNSNDSAMLKSIQNTLKNKTRPSENMD
151 SRFLMPEAYPSSPRKALRRIRQRSNSDITISELDVDSFDECISPTYKTGP
201 SLHREYGSTSSIDKQGTSGESFFDLLKGYKDDKSDRGPTPTKLSDFLITG
251 GGKGSGFSLDVIDGPISQRENLRLFKEREKPLKRRSKSETGDSSIFRKLR
301 NAKGEELGKSSDLEDNRSEDSVRPWTCPKCFAHYDVQSILFDLNEAIMNR
351 HNVIKRRNTTTGASAAVASLVSGPLSHSASFSSPMGSTEDLNSKGSLSM
401 DQGDDKSNELVMSCPYFRNEIGGEGERKISLSKSNSGSFSGGESASFEST
451 LSSHCTNAGVAVLEVPKENLVLHLDRVKRYIVEHVDLGAYYYRKFFYQKE
501 HWNYFGADENLGPVAVSIRREKPDEMKENGSPYNYRIIFRTSELMTLRGS
551 VLEDAIPSTAKHSTARGLPLKEVLEHVVPELNVQCLRLAFNTPKVTEQLM
601 KLDEQGLNYQQKVGIMYCKAGQSTEEEMYNNESAGPAFEEFLQLLGERVR
651 LKGFEKYRAQLDTKTDSTGHSLYTTYKDYEIMFHVSTMLPYTPNNKQQL
701 LRKRHIGNDIVTIVFQEPGAQPFSPKNIRSHFQHVFVIVRVHNPCSDSVC
751 YSVAVTRSRDVPSFGPPIPKGVTFPKSNVFRDFLLAKVINAENAAHKSEK
801 FRAMATRTRQEYLKDLAEKNVTNTPIDPSGKFPFISLASKKKEKSKPYPG
851 AELSSMGAIVWAVRAEDYNKAMELDCLLGISNEFIVLIEQETKSVVFNCS
901 CRDVIGWTSTDTSLKIFYERGECVSVGSFINIEEIKEIVKRLQFVSKGCE
951 SVEMTLRRNGLGQLGFHVNYEGIVADVEPYGYAWQAGIRQGSRLVEICKV
1001 AVATLSHEQMIDLLRTSVTVKVVIIPPHDDCTPRRSCSETYRMPVMEYKM
1051 NEGVSYEFKFPFRNNNKWQRNASKGPHSPQVPSQVQSPMTSRLNAGKGDG
1101 KMPPPERAANIPRSISSDGRPLERRLSPGSDIYVTVSSMALARSQCRNSP
1151 SNLSSSSDTGSVGGTYRQKSMPEGFGVSRRSPASIDRQNTQSDIGGSGKS
1201 TPSWQRSEDSIADQMEPTCHLPAVSKVLPAFRESPSGRLMRQDPVVHLSP
1251 NKQGHSDSHYSSHSSSNTLSSNASSAHSDEKWYDGDRTESELNSYNYLQG
1301 TSADSGIDTTSYGPSHGSTASLGAATSSPRSGPGKEKVAPLWHSSSEVIS
1351 MADRTLETESHGLDRKTESSLSLDIHSKSQAGSTPLTRENSTFSINDAAS
1401 HTSTMSSRHSASPVVFTSARSSPKEELHPAAPSQLAPSFSSSSSSSSGPR
1451 SFYPRQGATSKYLIGWKKPEGTINSVGFMDTRKRHQSDGNEIAHTRLRAS
1501 TRDLRASPKPTSKSTIEEDLKKLIDLESPTPESQKSFKFHALSSPQSPFP
1551 STPTSRRALHRTLSDESIYNSQREHFFTSRASLLDQALPNDVLFSSTYPS
1601 LPKSLPLRRPSYTLGMKSLHGEFSASDSSLTDIQETRRQPMPDPGLMPLP
1651 DTAADLDWSNLVDAAKAYEVQRASFFAASDENHRPLSAASNSDQLEDQAL
1701 AQMKPYSSSKDSSPTLASKVDQLEGMLKMLREDLKKEKEDKAHLQAEVQH
1751 LREDNLRLQEESQNASDKLKKFTEWVFNTIDMS 1783
```

Fig. 2A

```
  1 AYSYRGPQDFNSFVLEQHEYT 21
```

Fig. 2B

```
319  EDSVRPWTCPKCFAHYDVQSILFDLNEAIMNRHNVIKRRNTTTGASAAAVASLVSGPLSHSASFSSPMGS  E6TP1α
104  EPAFPPVLEPRWFAHYDVQSLLFDW---------------------APRSQGMGSHSEASSGTLAS     SPA-1

389  TEDLNSKGSLSMDQGDDKSNEIVMSCPYFRNEIGGEGERKISLSKSNSGSFSGCESASFESTLSSHCTNA  E6TP1α
149  AEDQAA----------SSDLLHGAPGFVCELGGEGEL------------GLGGPAFPPVPPA-LPNA    SPA-1

459  GVAVLEVPKENLVLHLDRVKRYIVEHVDLGAYYYRKFFYQKEHWNYFGADENLGPVAVSIRREKPDEMKE  E6TP1α
193  AVSILEEPQ-------NRTSAYSLEHADLGAGYYRKYFYGKEHQNFFGMDESLGPVAVSLRREEK-EGSG  SPA-1
87   ---------------------------ARIYRKHFLGKEHFNYYSLDTALGHLVFSLKYDVI-----   Rap1GAP

529  NGSPYNYRIIFRTSELMTLRGSVLEDAIPSTAKHSTARGLPLKEVLEHVVPELNVQCLRLAFNIPKVIEQ  E6TP1α
255  GGTLHSYRVIVRTTQLRTLRGTISEDALPP----GPPRGLSPRKLLEHVAPQLSPSCLRLGSASPKVPRT  SPA-1
122  -GDQEHLRLLLRT------KCRTYHDVLPISCLTEFPNVVQMAKL---VCEDVNVDRFYPVLY-PKASRL Rap1GAP
1499 ------------------------------------------------NESQSFER              Tuberin 599  LMKLDEQGLNYQ-QKVGIMYCKAGQSTEE-EMYNNESAGPAFEEFLQLLGERVRLKGFEKYRAQLDTKTD E6TP1α
321  LLTLDEQVLSFQ-RKVGILYCRAGQGSEE-EMYNNQEAGPAFMQFLTLLGDVVRLKGFESYRAQLDTKTD SPA-1
181  IVTFDEHVISNN-FKFGVIYQKLGQTSEE-ELFSTNEESPAFVEFLEFLGQKVKLQDEKGFRGGLDVTHG Rap1GAP
1507 SVQLLDQIPSYDTHKIAVLYVGEGQSNSELAILSNEHGSYRYTEFLTGLGRLIELKDCQPDKVYLGG-LD Tuberin 667  STGTHSLYTTYKDYEIM---FHVSTMLPYTPNNKQQLLRKRHIGNDIVTIVFQEPGAQPFSPKNIRSHFQ E6TP1α
389  STGTHSLYTTYQDHEIM---FHVSTMLPYTPNNQQQLLRKRHIGNDIVTIVFQEPGSKPFCPTTIRSHFQ SPA-1
249  QTGTESVYCNFRNKEIM---FHVSTKLPYTEGDAQQLQRKRHIGNDIVAVVFQDENT-PFVPDMIASNFL Rap1GAP
1576 VCGEDGQFLYCWHDDIMQAVFHIAILMPTKDVDKHRCDKKRHLGNDFVSIVYNDSG-EDFKLGTIKGQFN Tuberin 734  HVFVIVRVHNPCSDSVCYSVAVTRSRDVPSFGPPBIPK-GVIFPKSNVFRDFLLAKVINAENAAHKSEKFR E6TP1α
456  HVFLVVRAHTPCTPHTTYRVAVSRTQDTPAFGPALPAGGGPFAANADFRAFLLAKAINGEQAAGHARQFH SPA-1
315  HAYMVVQAEGGGPDGPLYKVSVTARDDVPFFGPPLPDPAV-FRKGPEFQEFLLTKLINAEYACYKAEKFA Rap1GAP
1645 FVHVIV                                                                Tuberin 803  AMATRTRQEYLKDLAEKNVTNTPIDPSGKFPFISLASKKKEKSKPYPGAELSSMGAIVWAVRA------  E6TP1α
526  AMATRTRQQYLQDLATNEVITISLDSASRFGLPSLGGRRRAAPRG-PGAELQAAGSLVWGVRAAPGARVA SPA-1
384  KLEERTRAAILETLYEE                                                     Rap1GAP 866  ----EDYNKAMELDCLLGISNEFIVLIEQETKSVVFNCSCRDVIGWTSTDTSLKIFYERGECVSV---GS E6TP1α
595  AGAQASGPEGIEVPCLLGISAEAIVLVAPRDGRVVFNCACRDVLAWTFSEQQLDLYHGRGEAITLRFDGS SPA-1

929  FINIEEIKEIVKRLQFVSKGCESVEMTL-RRNGLG-QLGFHVNYEGIVADVEPYGYAWQAGLRQGSRIVE E6TP1α
665  --PGQAVGEVVARLQLVSRGCETRELAL-PRDGQG-RLGFEVDAEGFVTHVERFTFAETAGLRPGARLLR SPA-1

997  ICKVAVATLSHEQMIDLLRTSVIVKVVIIPPHDDCTPRRSCSETYRMPVMEYKMNEGVSYEFKFPFRNNN E6TP1α
731  VCGQTLPSLRPEAAAQLLRSAPKVCVTVLPPDESGRPRRSFSELYTLSLQEP---------------   SPA-1

1067 KWQRNASKGPHSPQVPSQVQSPMTSR-LNAGKGDGKMPP------PERAANI-------PRSISSDGRPL E6TP1α
783  --SRRGAPDPVQDEVHGVTLLPTIKQLLHLCLQDGGSPPGPGDLAEERTEFLHSQNSLSPRSSLSDEAPV SPA-1

1705 --------------/ /------------PYSSSKDSSPTLASKVDQLEGMLKMLREDLKKEKEDKAH  E6TP1α
963                              PKSDAEPEPGNLSEKVSHLESMLRKLQEDLQKEKADRAA   SPA-1
                                         *       *      *     *

1744 LQAEVQHLREDNLRLQEESQNASDKLKKFTEWVFNTIDMS   E6TP1α
1002 LEEEVRSLRHNNRRLQAESESAATRL                SPA-1
```

Fig. 2C

E6 TARGETED PROTEIN (E6TP1)

GRANT SUPPORT

Work described herein was supported in part by funding from the National Institute of Health, grant numbers CA 56803 and CA 64823. The United States Government has certain rights in the invention.

FIELD OF THE INVENTION

The present invention relates to compositions and methods of use for a novel putative GTPase activating protein ("GAP") that interacts with papilloma virus E6 oncoprotein and is thereby targeted for degradation. Said novel protein, herein designated "E6TP1" for E6 targeted protein, its nucleic acid and polypeptide sequences, and derivatives, fragments, and analogues thereof, are described. The invention further relates to cells containing recombinant E6TP1 nucleic acid and protein sequences; animal models of the same, including transgenic and "knock-out" animal models; anti-E6TP1 specific antibodies, and derivatives, fragments, and analogues thereof; oligonucleotides hybridizable to sense or antisense E6TP1 nucleic acids; oligonucleotide pairs capable of PCR amplifying E6TP1; and use of any of the above compositions in diagnostics, therapeutics, and treatments of tumors. Specific embodiments include methods of use of E6TP1 in tumor suppression. In addition, the present invention relates to compositions and methods of use of E6TP1 in high-risk human papilloma virus ("HPV") associated carcinomas of cervix and other anogenital tumors.

BACKGROUND OF THE INVENTION

Carcinomas, the tumors originating from epithelial cells, constitute nearly 80% of all human cancers. In the U.S. alone, a predicted 650,000 new cases of the carcinomas of lung, colon, breast, prostate and cervix will be diagnosed in 1998, and nearly 300,000 of these will be fatal. See, e.g., American Cancer Society Cancer Facts and Figures, *American Cancer Society, Inc.* (1998). Despite these astonishing statistics, much of our knowledge into cell biology of the oncogenic process stems from studies of fibroblasts, reflecting the available experimental models.

A critical event in carcinogenesis is the conversion of normal epithelial cells, with a finite proliferative potential, into cells that are endowed with an ability to multiply continuously, a trait that allows accumulation of further genetic alterations enroute to full malignancy. In vitro, this behavior manifests as continuous proliferation of cells beyond their limited life span. This process is referred to as immortalization. Understanding the biochemical basis of immortalization is therefore likely to identify crucial cellular pathways involved in cellular control. The recently identified ability of viral oncogenes to immortalize normally senescent epithelial cells has provided practical approaches to delineate the regulatory cascades involved in these critical paths.

For example, normal human mammoplasty-derived mammary epithelial cells reproducibly proliferate in vitro for about 20 passages, followed by their senescence. See, e.g., Band and Sager, *Proc Natl Acad Sci USA.*, 86:1249–1253 (1989); Band, *Sem Cancer Biol,* 6: 185–192 (1995). A similar finite life span is exhibited in vitro by other epithelial cells. A number of viral oncogenes, including SV40 large T and adenovirus E1A and E1B, were inefficient at immortalizing the epithelial cells, in sharp contrast to rodent fibroblasts which were efficiently transformed by these oncoprotein. See, e.g., Sager, *Cancer Cells,* 2: 487–494 (1984). Strikingly, however, we found that transfection of the genome of high risk human papilloma viruses ("HPVs")-16 or -18, which are naturally associated with epithelial oncogenesis in the genitourinary tract, led to reproducible and highly efficient immortalization of MECs. See, e.g., Band et al., *Proc Natl Acad Sci USA,* 87: 463–467 (1990). The HPV genome transfection also efficiently immortalized keratinocytes (a natural host epithelial cell type for these viruses) and other epithelial cell types. See, e.g., Kaur and McDougall, *J Virol,* 62: 1917–1924 (1988); Yeager et al., *Cancer Res,* 55: 493–497 (1995). In all of these cases, the HPV genome-transformed cells were immortal but not fully tumorigenic, as shown by their inability to grow in soft agar or form tumors when implanted in nude mice. However, when these immortal cells are transfected with additional oncogenes (e.g., activated H-ras or mutant erbB-2), they attained a tumorigenic phenotype. See, e.g., Woodworth, In: Neoplastic Transformation in Human Cell Culture: Mechanisms of Carcinogenesis, Eds. Rhim and Dritschilo, Humana Press, New Jersey, pp 153–161 (1991). Thus, introduction of the HPV genome into primary human epithelial cells induces a preneoplastic transformation.

The human papilloma viruses ("HPVs") are associated with epithelial tumors or benign lesions, especially those of anogenital origin. See, e.g., Zur Hausen and Schneider, "The Papillomaviruses" In: The Papillomaviruses, Howley and Salzman (ed.), Vol. 2 of The Papovaviridae, (Plenum, New York) pp 245–263 (1987). These viruses are grouped into low-risk HPVs, such as HPV6 and HPV11, which are usually associated with benign warts, and high-risk HPVs, such as HPV 16 and HPV18, which are associated with carcinomas of cervix and other genital tumors. See, e.g., Zur Hausen, ibid. Previous studies have identified two viral oncoproteins "E6" and "E7", which are expressed in the majority of HPV-associated carcinomas, and which functionally inactivate cellular tumor suppressor proteins p53 and retinoblastoma (Rb), respectively. See, e.g., Dyson et al., *Science* 243: 934–937 (1989); Huibregtse et al., *Mol Cell Biol* 13: 4918–4927 (1993); Scheffner et al., *Cell* 75: 495–505 (1993). This is thought to provide the basis for the ability of high-risk, but not the low-risk, HPVs to promote oncogenesis.

In recent years, a distinct mechanism of viral oncoprotein-induced inactivation of tumor suppressor protein function has emerged, involving the targeting of tumor suppressor protein(s) to ubiquitin-proteasome mediated degradation machinery. See, e.g., Boyer et al., ibid.; Ciechanover, *Cell* 79: 13–21 (1994); Huibregtse et al., *Mol Cell Biol* 13: 4918–4927 (1993). The ubiquitin-proteasome pathway participates in physiological regulation of the levels of cell-cycle related proteins such as cyclins, cdks, and tumor suppressor proteins such as p53 and Rb proteins. See, e.g., Boyer et al., ibid.; Ciechanover, ibid.; Maki et al., *Cancer Res* 56: 2649–2654 (1996). Viral oncoproteins target cellular tumor suppressor proteins to this pathway for enhanced degradation. See, e.g., Huibregtse et al., *EMBO J* 10: 4129–4135 (1991); Scheffner et al., *Cell* 63: 1129–1136 (1990). High-risk HPV E6 oncoproteins associate with E6-AP, a ubiquitin ligase, which in turn interacts with p53 and targets it for degradation. See, e.g., Huibregtse et al (1991), ibid.; Scheffner et al., ibid. We have since found that the high-risk HPV16 E7 oncoprotein also uses the ubiquitin proteasome pathway for enhanced degradation of bound Rb protein. See, e.g, Boyer et al., *Cancer Res* 56: 4620–4624 (1996).

Characterization of oncogenesis-related cellular targets of HPV oncoproteins has been facilitated by the ability of HPV to dominantly immortalize primary human cells in vitro. See, e.g., supra; Band et al., *Proc Natl Acad Sci USA* 87: 463–467 (1990); Woodworth et al., *J Virol* 63: 159–164 (1989). Both E7 and E6 proteins of high-risk HPVs are required for efficient immortalization of cervical keratinocytes, E6 alone is not enough. See, e.g., Hawley-Nelson et al., *EMBO J* 8: 3905–3910 (1989); Munger et al., *J Virol* 63: 4417–4421 (1989).

Surprisingly, we found that HPV E6 alone is sufficient to immortalize a subtype of normal human mammary epithelial cells ("MECs"). See, e.g., Band et al., *J Virol* 65: 6671–6676 (1991). Use of HPV16 DNA constructs with disruption of individual open reading frames of early ("E") viral genes demonstrated that E1, E2, E4 and E7 genes were dispensable for MEC immortalization. In contrast, the E6 open reading frame was indispensable. See, e.g., Band et al., ibid. Introduction of the E6 gene alone demonstrated that this gene was sufficient to immortalize MECs. See, e.g., Band et al., *EMBO J,* 12: 1847–1852 (1993). Thus, immortalization of the human MECs by E6 provides a simple single-oncogene model wherein to define the cellular pathways whose alterations underlie immortalization of epithelial cells. See e.g., Band et al., ibid.

Mutational analysis of HPV16 E6 revealed a direct correlation between MEC immortalization and the ability of E6 proteins to induce in vivo p53 degradation in these cells, confirming the crucial role enhanced p53 degradation plays in E6-mediated immortalization. See, e.g., Band et. al., *EMBO J* 12: 1847–1852, (1993); Dalal et al., *J Virol* 70: 683–688 (1996). However, when tested, loss of p53 itself was insufficient for immortalization. Of a panel of dominant-negative p53 missense mutants, known to complex with and functionally inactivate the endogenous wild-type p53 protein, nine out of the twelve mutants tested failed to immortalize MECs, even though they were expressed at high levels. See, e.g., Scheffner et al., *J Virol* 66: 5100–5105 (1992); Takahashi et al. *Science,* 246: 491–494 (1989). Furthermore, the remaining three mutants immortalized the MECs much less efficiently compared to HPV16 E6. See, e.g., Band et al., *EMBO J,* 12: 1847–1852 (1993); Dalal et al., *J Virol,* 70: 683–688 (1996); Gao et al., *Cancer Res,* 56: 3129–3133 (1996); and Cao et al., *Cancer Res,* 57: 5584–5589(1997). Together, these results strongly suggest that the HPV 16 E6 oncoprotein targets additional biochemical pathways whose functional inactivation is important for immortalization.

Consistent with this possibility, HPV16 E6 has recently been shown to interact with three proteins: "ERC55", a putative calcium binding protein; "paxillin", a protein involved in transducing signals from the plasma membrane to the actin cytoskeleton; and "hDlg", the human homologue of the Drosophila discs large tumor suppressor protein. See, e.g., Chen et al., *Science* 269: 529–531 (1995); Kiyono et al., *Proc Natl Acad Sci USA* 94: 11612–11616 (1997); Lee et al., *Proc Natl Acad Sci USA* 94: 6670–6675 (1997); Tong and Howley, *Proc Natl Acad Sci USA* 94: 4412–4417 (1997). Binding of these proteins to high or low risk HPV E6 mutants correlates with the immortalizing ability of the E6 proteins, suggesting a potential role for these non-p53 E6-binding proteins in cellular transformation, although direct studies to demonstrate such a role have not been carried out.

In nonviral associated carcinomas, when the gene that encodes tuberin ("TSC2"), a tumor suppressor protein frequently mutated in the autosomal dominant syndrome of tuberous sclerosis, was introduced into a renal carcinoma cell line derived from the Eker rat, a model of hereditary renal carcinoma, tumorigenicity was suppressed. See, e.g., Jin et al., *Proc Natl Acad Sci USA* 93: 9154–9159 (1996).

Signals that activate growth, and therefore antagonize the function of cellular tumor suppressor proteins, are mediated through growth factor receptors located on the plasma membrane that interact with highly regulated signaling pathways. The small Ras-like GTPases are a family of signaling proteins that includes Ras, Rap1, Rap2, R-ras, TC21, Ral, and Rhob, and are defined by a common homology domain known in Ras to interact with downstream targets. Mutant Ras proteins are found in around 15% of all human tumors, and in 50 to 90% of all adenocarcinomas of the colon and pancreas, respectively. See, e.g., Bos, *EMBO J* 17: 6776–6782 (1998). Therefore, the Ras family of proteins plays an important role in non-HPV associated carcinomas.

Ras and Ras-related proteins act as molecular switches for controlling cellular signaling pathways by cycling between GTP-bound "on" and GDP-bound "off" states. In the GTP-bound "on" state, these proteins interact with and activate effector proteins (e.g., raf activation by Ras). Intrinsic GTPase activity hydrolyzes GTP to GDP, returning the G-binding proteins to the "off" (GDP-bound) state. Two families of regulatory proteins control the G-protein cycle. Guanine nucleotide exchange factors (GEFs) stimulate the release of bound GDP, promoting GTP loading. See, e.g., Feig, *Curr Opin Cell Biol,* 6: 204–211 (1994); Polakis and McCormick, *Cancer Surveys,* 12: 25–42 (1992); Polakis and McCormick, *J Biol Chem,* 268: 9157–9160 (1993). In contrast, GTPase-activating proteins (GAPs) stimulate the otherwise slow intrinsic GTPase activity by several orders of magnitude, inducing GTP hydrolysis to GDP and returning the G-binding proteins to an "off" state. Many members of this protein signaling family act as activated oncogenes in their mutated form. Oncogenic mutations of Ras invariably lead to an inability of GAP proteins to stimulate GTPase activity, resulting in a constitutively "on" state. Thus, GAP proteins provide a critical regulatory mechanism to ensure normal function of small G proteins.

Analogous to the Ras-specific GEF "son-of-sevenless" ("SOS"), a Rap-specific GEF "C3G" has been recently identified. See, e.g., Ichiba et al., *J. Biol Chem.,* 35: 22215–22220 (1997); Okada et al., *EMBO J,* 17: 2554–2565 (1998). C3G associates with the SH3 domains of the Crk adaptor proteins and their SH2 domains recruit it to tyrosine phosphorylated membrane receptors near the membrane-associated Rap (e.g., epidermal growth factor receptor (EGFR) and nerve growth factor receptor (NGFR). See, e.g., Okada and Pessin, *J. Biol Chem.,* 272: 28179–28182 (1997); York et al., *Nature,* 392: 622–626 (1998). However, while a clear role has been delineated of Ras G-protein pathway in controlling cell proliferation and differentiation through MAP kinase cascades, the role of Rap1, a known suppressor of Ras activity, has remained enigmatic.

Rap1 was originally identified by its ability to revert the phenotype of viral K-ras transformed NIH3T3 cells. See, e.g., Kitayama et al., *Cell* 56: 77–84 (1989). Rap1, whose effector domain is nearly identical to that of Ras, was shown to interact with the Ras effectors. See, e.g., Frech et al., *Science* 249: 169–171 (1990); Hata et al., *J Biol Chem* 265: 7104–7107 (1990); Herrmann et al., *J Biol Chem* 271: 6794–6800 (1996). Thus it is hypothesized that Rap1 antagonizes Ras function by sequestering Ras effectors in inactive complexes (e.g., constitutively activate RapV12 mutant inhibited EGF-stimulated Ras-mediated MAP kinase activation in rat fibroblasts). See, e.g., Cook et al., *EMBO J*, 12: 3475–3485 (1993).

Surprisingly, however, Vossler et al. showed in PC12 cells that Rap1, activated either by mutation or by the cAMP-dependent protein kinase ("PKA"), is a selective activator of B-Raf, which activates the MAP kinase cascade and leads to sustained activation of the transcription factor Elk-1. Vossler et al., *Cell* 89: 73–82 (1997). Also, Yoshida et al. showed that the microinjection of activated Rap1 into Swiss 3T3 cells enhanced the mitogenic signaling pathways in response to insulin. Yoshida et al., *Mol Cell Biol* 12: 3407–3414 (1992). Transfection of Rap1 into Swiss 3T3 cells increased cell proliferation and oncogenically transformed the cells. See, e.g., Altschuler and Ribeiro-Neto, *Proc Natl Acad Sci USA* 95: 7475–7479 (1998). In addition, expression in 293 HEK cells of the Rap GEF C3G activated the JNK pathway. See, e.g, Tanaka and Hanafusa, *J Biol Chem*, 273: 1281–1284 (1998). Rap GTP loading has also been demonstrated upon stimulation through the T cell receptor and thrombin activation of platelets. See, e.g., Reedquist and Bos, *J Biol Chem*, 9: 4944–4949 (1998); Franke et al., *EMBO J*, 16: 252–259 (1997). Finally, Rap mainly localizes intracellularly at the endocytic and lysosomal vesicles, whereas Ras localizes to the plasma membrae. See, e.g., Pizon et al., *Exp Cell Res* 246: 56–68 (1999); Bos *EMBO J* 23: 6776–6782 (1998). These results suggest that the function of Rap signaling on the Ras pathway is likely to depend on the cell type, the type of receptors, the particular Rap proteins expressed and their localization, and the nature of effector proteins expressed (e.g., Raf vs B-raf).

Thus, a need remains in the art for the identification of tumor suppressors involved in specific carcinomas and in HPV-associated disease states. In addition, identification of cellular factors, other than p53, that are both bound by immortalization-competent HPV E6 and are targeted for enhanced degradation is key to finding a more viable control of tumor suppression and finding potential new therapeutics for treating all stages of HPV-induced disease.

SUMMARY OF THE INVENTION

Elucidation of biochemical pathways whose inactivation leads to oncogenic transformation of epithelial cells, the precursors for carcinomas, is a central goal in cancer biology. Normal epithelial cell growth is tightly controlled, and these cells live for a finite life span before they senesce and die. An essential initial step in tumorigenesis involves loss of senescence, or immortalization, which allows a cell to grow indefinitely and to go through further oncogenic steps resulting in fully malignant behavior. We have demonstrated that primary human mammary epithelial cells ("MECs") are efficiently immortalized by a single oncogene, namely HPV16 E6, providing a simple model to elucidate mechanisms of cellular transformation uncomplicated by the effects of additional oncogenes required for efficient immortalization of other epithelial cells.

We used a modified yeast two-hybrid system (see, e.g., Chien et al., *Proc Natl Acad Sci USA* 88: 9578–9582 (1991)) to identify a novel putative GAP protein, "E6TP1" (for "E6-Targeted Protein") that interacts with high-risk HPV E6 proteins and is targeted for in vitro and in vivo degradation. The ability of E6TP1 to selectively interact with immortalizing HPV16 E6 mutants, but not non-immortalizing HPV16 E6 mutants, implicates this protein in E6-mediated oncogenesis. Two isoforms of human E6TP1 were cloned, namely E6TP1α and E6TP1β. Therefore, the present invention relates to full length E6TP1α complementary DNA ("cDNA") nucleotide sequence (GenBank Accession Number AF090989) [SEQ ID NO:1]; E6TP1α predicted amino acid sequence [SEQ ID NO:2]; full length E6TP1β cDNA nucleotide sequence (GenBank Accession Number AF090990) [SEQ ID NO:3]; and E6TP1β predicted amino acid sequence [SEQ ID NO:4]; as well as fragments, derivatives, and analogues of said E6TP1α and E6TP1β nucleic acid and amino acid sequences. The invention further provides cells containing recombinant E6TP1 nucleic acid and amino acid sequences, or fragments, derivatives, and analogues thereof; recombinant animal models thereof; anti-E6TP1 specific antibodies, and derivatives, fragments, and analogues thereof; oligonucleotides hybridizable to sense or antisense E6TP1 nucleic acids, and use of any of the above in diagnostics, therapeutics, and treatments of tumors, including use of E6TP1 in tumor suppression and prevention of HPV-associated carcinomas. Methods of isolation and purification of E6TP1 protein are also provided.

The E6TP1 protein exhibits high homology to the GTPase-activating proteins ("GAPs") "SPA-1", "tuberin", and "Rap1GAP", three GAPs known to regulate the Rap protein. Rap is a Ras-like GTPase localized mainly near endocytic and lysosomal vesicles in the cell interior. See, e.g., Bos, *EMBO J* 17: 6776–6782. The mRNA for E6TP1 is widely expressed in tissues and in in vitro cultured cell lines. The gene for E6TP1 localizes to chromosome 14q23.2–14q24.3, within a locus that has been shown to undergo loss of heterozygosity in malignant meningiomas. Importantly, E6TP1 is targeted for degradation by the high-risk, but not the low-risk, HPV E6 proteins both in vitro and in vivo. Furthermore, the immortalization-competent but not the immortalization-incompetent HPV16 E6 mutants target the E6TP1 protein for degradation. This novel target for E6 oncoprotein provides a potential link between HPV E6 oncogenesis and alteration of a small G-protein signaling pathway.

Epithelial cells are the source of all forms of carcinoma. E6TP1 is likely involved in the maintenance of the untransformed state of normal epithelial cells, as we have shown that E6-induced degradation of this protein constitutes one of the lesions identified upon E6-induced cellular immortalization. Therefore, E6TP1 defines a novel biochemical pathway of inhibitory control of cell growth whose function is critical to prevent oncogenic transformation. As noted in the BACKGROUND Section, supra, transfection experiments that replaced the p53 and Rb tumor suppressors in carcinoma cells demonstrated that said replacement of the target protein of HPV oncoprotein was alone sufficient to halt HPV-induced transformation and cell proliferation. Herein we identify E6TP1 as a novel putative tumor suppressor in carcinoma cells. As such, our invention encompasses methods of use of E6TP1 in diagnosis, prevention, and treatment of carcinomas and related diseases.

Various embodiments of the invention include administrating E6TP1 nucleic acids and proteins as a therapeutic agent, regulating E6TP1-associated growth inhibition and tumor suppressor pathways, using E6TP1 in diagnosis of disease states, treating and preventing HPV-associated infections, and using E6TP1-specific antibodies and anti-sense nucleic acids for modulating E6TP1 and associated proteins and pathways. Also included are methods of administrating E6TP1 in carcinomas and HPV-associated diseases pathway. In addition, the present invention provides compositions and methods of using E6TP1 in high-risk human papilloma virus ("HPV") associated carcinomas of cervix and other anogenital tumors. Methods of identifying E6TP1-associated proteins are provided, in order to provide newer targets for future development of gene-based and other associated diagnostic and therapeutic strategies.

DETAILED DESCRIPTION OF THE INVENTION

Figure 1A:
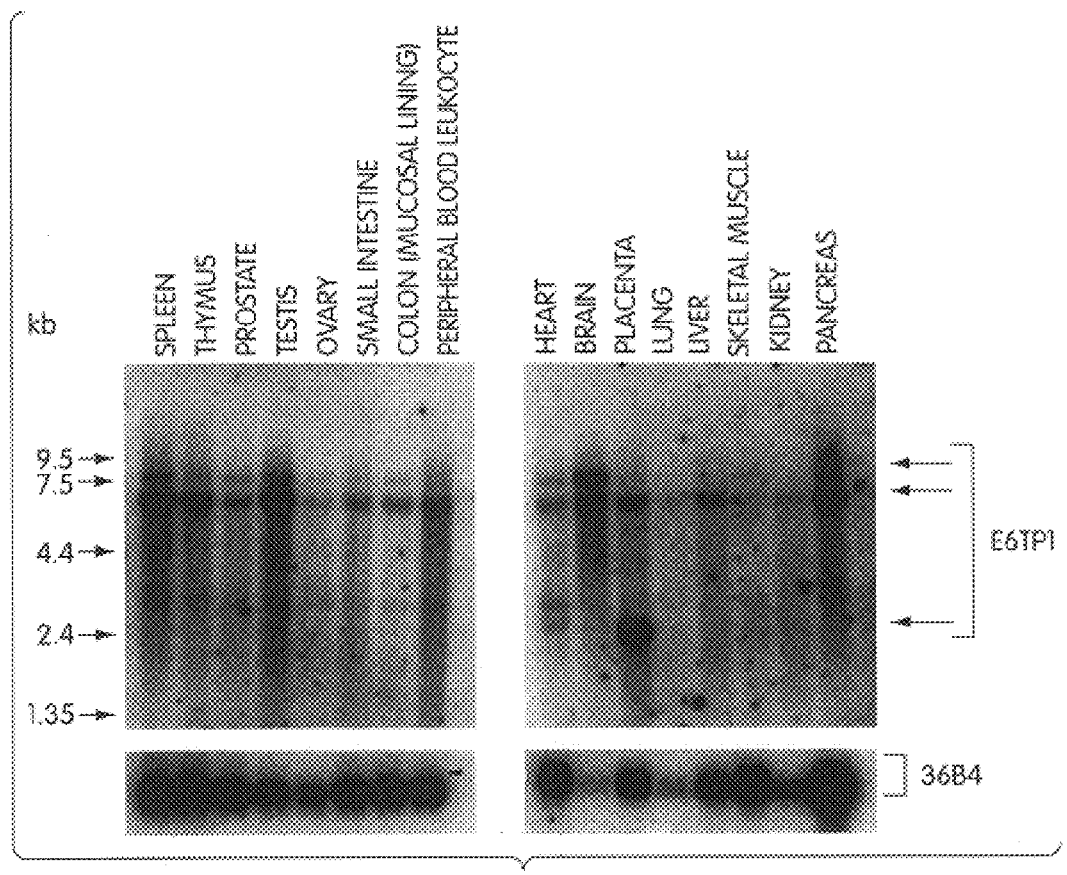
FIG. 1 illustrates E6TP1 mRNA expression in human tissues (Panel A) and cultured cell lines (Panels B and C).
Figure 1B:
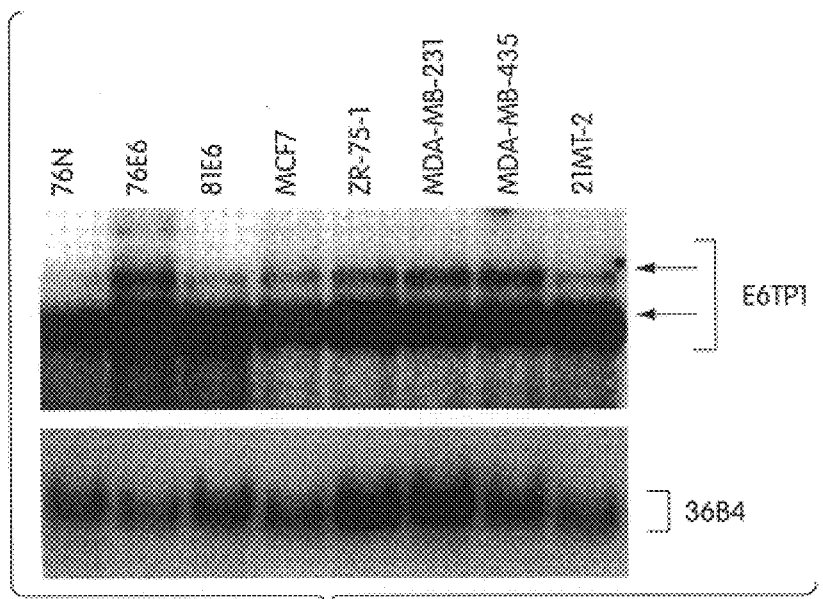

We used the yeast two-hybrid system to isolate a novel E6-binding protein designated E6TP1 (E6-targeted protein 1). E6TP1 represents a novel gene whose mRNA is widely expressed. Two major E6TP1 transcripts of 7.5 and 6.0 kb are present in all tissues and established cell lines tested (FIGS. 1A and 1B). The 6.0 kb transcript predominates in most tissues, whereas the 7.5 kb transcript is most abundant in brain tissue and a 2.2 kb transcript is abundant in placenta (FIG. 1A). Several full length cDNA clones representing the major 6.0 kb transcript were isolated [SEQ ID NOS:1 and 3]. The first cDNA predicts a 1783 aa polypeptide (E6TP1α, FIG. 2A)[SEQ ID NO:2]. The second cDNA clone contains a 63 bp in-frame insertion after nucleotide 4025 of SEQ ID NO:2, predicting a 1804 aa polypeptide (E6TP1β, FIG. 2B)[SEQ ID NO:4]. A recent rat cDNA entry in the NCBI database (GenBank accession # AF026504) had a 95.4% amino acid identity with E6TP1α (excluding a 39 aa insertion after aa 630 present only in the rat sequence), and is likely to be the rat homologue of E6TP1α. See Takeuchi et al., *J Biol Chem* 272: 11943–11951. A human cDNA fragment (GenBank accession # AB007900) that encodes the C-terminal 1138 aa of E6TP1β was also found. However, as this latter human fragment was isolated from brain, it is not yet known whether this sequence represents the 7.5 kb mRNA species predominant in brain (infra), or the 6.0 kb transcript described herein. See Ishikawa et al., *DNA Res* 4: 307–313 (1997), and infra.

The presence of multiple transcripts with tissue-specific differences in their relative abundance, together with isolation of two isoforms that differ by the presence of a 21 aa insert (SEQ ID NO:13) (present in E6TP1β and absent in E6TP1α) demonstrates that several forms of E6TP1 protein are expressed and their relative expression is regulated.

Comparison of E6TP1 polypeptide with other proteins showed that both isoforms of E6TP1 possess a region with extensive homology to the GAP domains of several previously characterized GTPase activating proteins. Those we identified as having the highest homology are either documented or likely members of the RapGAP family, with selectivity towards Rap, the Ras-related small G proteins. In particular, high homology was observed with SPA-1 (SEQ ID NOS:14&15) (see, e.g., Kurachi et al., *J Biol Chem* 272: 28081–28088 (1997)), Rap1GAP (SEQ ID NO:16) (see, e.g., Rubinfeld et al., *Mol Cell Biol* 12: 4634–4642 (1992)); tuberin (SEQ ID NO:17) (see, e.g, Kobayashi et al., *Proc Natl Acad Sci USA* 94: 3990–3993 (1997)); and Drosophila Rapgap1 (see, e.g., Chen et al., *Proc Natl Acad Sci USA* 94: 12485–12490 (1997)); as well as with two putative *C. elegans* RapGAPs (Table 1, infra). Rap1GAP1 exhibits strong GAP activity towards Rap1, but relatively weak activity towards Rap2. See, e.g., Rubinfeld et al., *Cell* 65: 1033–1042 (1991). SPA-1, on the other hand, exhibits GAP activity towards both Rap1 and Rap2. See, e.g., Kurachi et al., ibid. While it has been suggested that tuberin acts as a Rab5GAP in vivo (see, e.g., Xiao et al., *J Biol Chem* 272:6097–6100 (1997)), tuberin also exhibits in vitro GAP activity towards Rap1. See, e.g., Wienecke et al., *J Biol Chem* 270: 16409–16414 (1995). These comparisons strongly suggest that E6TP1 also functions as a GAP toward Rap and/or other small GTPases.

TABLE 1

Comparison of E6TP1 with Rap1GAP homologous proteins

| GAP protein | Species | Accession no. | aa | % Identity with E6TP1 aa 489–819 |
|---|---|---|---|---|
| SPA-1 | H. sapiens | 2389009 | 216–542 | 64 |
| T27F2.2 | C. elegans | 1403291 | 185–506 | 56 |
| Rapgap1 | D. melanogaster | 2655096 | 230–540 | 40 |
| CELF47F6 | C. elegans | 1707164 | 33–343 | 41 |
| Rap1GAP | H. sapiens | 106198 | 13–326 | 38 |
| Tuberin | H. sapiens | 450352 | 1499–1650 | 31 |

Homology analysis revealed that E6TP1 is most closely related to SPA-1 (SEQ ID NOS:14–15). In addition to high sequence identity between their GAP domains (SEQ ID NO:14), strong sequence conservation was noted in other regions (FIG. 2). A C-terminal leucine zipper previously identified in SPA-1 (SEQ ID NO:15) is conserved in E6TP1 (E6TP1α aa 1705–1779, E6TP1β 1726–1790). Another conserved region with high sequence identity is predicted to form a PDZ domain. PDZ domains are modular structures identified in a number of distinct proteins. See, e.g., Ponting et al., *Bioessays* 19: 469–479 (1997). One notable function of such domains is to promote sub-membranous protein assemblies by binding to C-termini of transmembrane proteins. See, e.g., Ponting et al., *Bioessays* 19: 469–479 (1997). These extensive sequence comparisons strongly suggest that SPA-1 and E6TP1 represent a subfamily of RapGAPs.

Interestingly, the expression of SPA-1 mRNA is upregulated quickly following mitogenic stimulation of lymphocytes, suggesting a potential role for this subfamily of proteins in cell growth regulation and/or cell cycle events. In fact, introduction of SPA-1 into the NIH 3T3 cells, followed by serum starvation, led to cell death resembling the mitotic catastrophes of the S phase. See, e.g., Hattori et al., *Mol Cell Biol* 15: 552–560 (1995). The gene that encodes tuberin ("TSC2") is frequently mutated in the autosomal dominant syndrome of tuberous sclerosis and therefore represents a clear example of a tumor suppressor protein. Furthermore, when TSC2 was introduced into a renal carcinoma cell line derived from the Eker rat, a model of hereditary renal carcinoma, tumorigenicity was suppressed. See, e.g., Jin et al., *Proc Natl Acad Sci USA* 93: 9154–9159 (1996). Similarly, expression of TSC2 as a transgene in Eker rat rescued these animals from embryonic lethality and renal carcinogenesis. See, e.g., Kobayashi et al., *Proc Natl Acad Sci USA* 94: 3990–3993 (1997). Another protein that has been recently identified as an HPV E6-binding protein, hDlg, is a homologue of a protein identified in Drosophila as a tumor suppressor protein. See, e.g., Kiyono et al., *Proc Natl Acad Sci USA* 94: 11612–11616 (1997); Lee et al., *Proc Natl Acad Sci USA* 94: 6670–6675 (1997). Thus, it is tempting to speculate that the E6 oncoprotein-binding partner E6TP1 may also be involved in cell growth regulation and carcinogenesis. This would suggest a potential link between HPV E6 oncogenesis and alteration of a small G-protein signaling pathway.

Notably, E6TP1 localizes to chromosome 14q23.2–14q24.3. This region has been previously shown to undergo loss-of-heterozygosity in malignant meningiomas (see, e.g., Menon et al., *Oncogene* 14: 611–616 (1997); Simon et al., *Cancer Res* 55: 4696–4701 (1995); Tse et al., *Hum Pathol* 28: 779–785 (1997)), suggesting that this locus harbors a tumor suppressor gene, thus further validating the assumption that E6TP1 represents a relevant tumor suppressor gene.

E6TP1 may contribute to cell growth regulation and toward HPV E6-induced cellular transformation in a variety of ways. The instant invention provides for all possible mechanisms of action, and is not limited by any one mode. The Rap family of small G-proteins (which includes Rap1 A, B, and Rap 2 A, B) are structurally closely related to Ras (Rap 1A is 53% identical to Ras). See, e.g., BACKGROUND Section; Sprang, *Annu Rev Biochem*, 66: 639–678 (1997).

Ras and Ras-related proteins act as molecular switches for controlling cellular signaling pathways by cycling between two conformations induced by the binding of either GTP or GDP. Two families of regulatory proteins control the G-protein cycle. Guanine nucleotide exchange factors (GEFs) induce the dissociation of GDP to allow loading of the more abundant GTP, forming an activated complex. In turn, GTPase-activating proteins (GAPs) stimulate the hydrolysis of GTP to GDP, returning the G-binding proteins to an inactive state. See, e.g., Feig, *Curr Opin Cell Biol,* 6: 204–211 (1994); Polakis and McCormick, *Cancer Surveys,* 12: 25–42 (1992); Polakis and McCormick, *J Biol Chem,* 268: 9157–9160 (1993).

Rap is ubiquitously expressed and is one of the major substrates of PKA in platelets. Depending on cell type and location, activation of Rap1 can be implemented by cAMP, diacylglycerol, or calcium. Regulation is apparently mediated by these second messengers directly activating Rap-specific GEFs. See, e.g., Bos *EMBO J* 23: 6776–6782 (1998). In contrast to the model of Rap1 functioning as a repressor of Ras signaling (see BACKGROUND, supra), when comparing activation of Rap1 with that of Raf, the downstream activator of Ras, Zwartkruis et al. (1998) found that most signals that activate Raf activate rather than inhibit Rap1. Furthermore, increasing the amount of GTP-bound Rap1 by TPA in Rat1 cells did not inhibit Ras-dependent activation. See, e.g., Zwartkruis et al., *EMBO J* 17: 5905–5912 (1998). Therefore, it appears that Rap1 functions in a signaling pathway distinct from Ras, while using similar or identical effectors.

Thus, if activation of Rap G-proteins mediate a growth promoting signaling pathway in epithelial cells, E6TP1 can regulate this pathway by catalyzing the conversion of Rap-GTP to Rap-GDP. Alternatively, a second plausible mechanism based on the biology of Ras-like G proteins would be that E6TP1 functions as an effector for Rap, analogous to Ras-GAP. See, e.g., Kitayama et al., *Cell,* 56: 77–84 (1989). Thus, E6TP1 may represent a downstream effector in a growth-inhibitory pathway initiated through Rap-GTP loading. Indeed, one or both of these mechanisms may be involved in the postulated growth regulatory/tumor suppressor function of E6TP1.

Sequence homology analysis strongly suggested E6TP1 to be a RapGAP. As a putative negative regulator of Rap1 GTPase, E6TP1 could negatively regulate the mitogenic signaling pathways mediated by Rap1 or related proteins. Degradation of E6TP1 by HPV 16 E6 or inactivation of E6TP1 by other mechanisms such as mutation would then be expected to promote mitogenic signaling and thus may contribute to oncogenic transformation.

Figure 4:
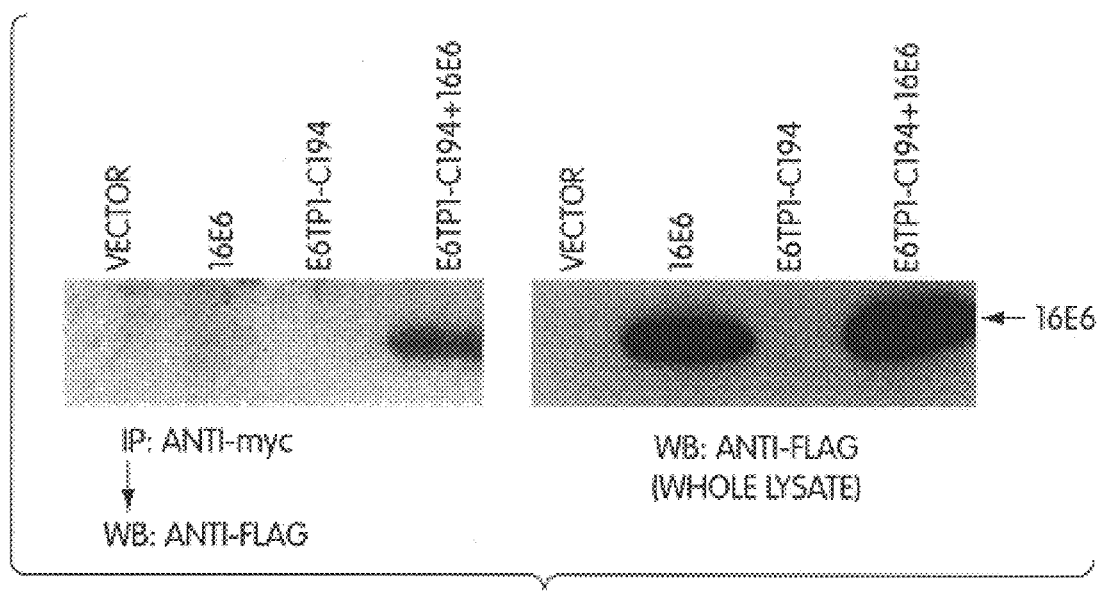
FIG. 4 illustrates in vivo binding of high-risk HPV16 E6 protein to E6TP1.
Figure 5A:
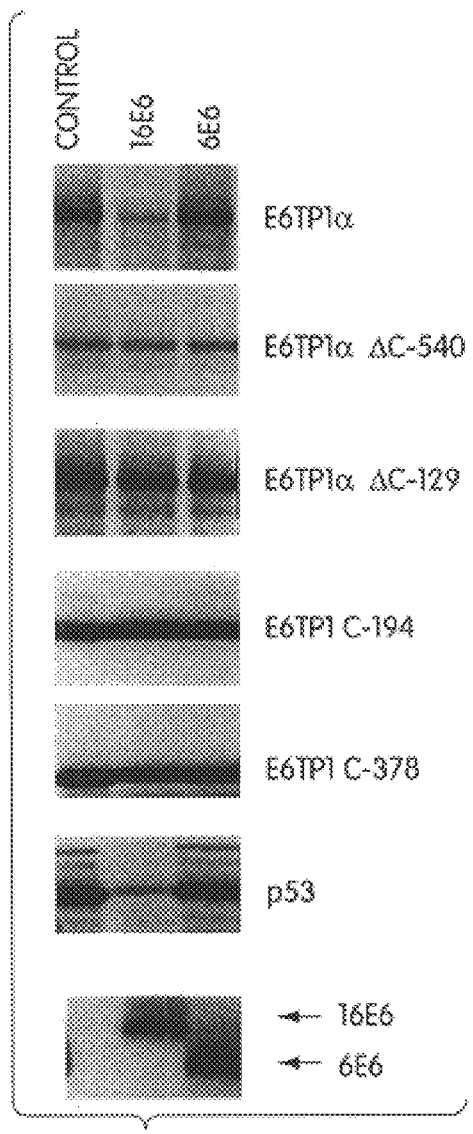
FIG. 5 illustrates HPV16 or HPV6 E6-induced: (Panel A) in vitro degradation of E6TP1α, both full length and various fragments, and p53 proteins; and (Panel B) in vivo degradation of E6TP1α.

E6TP1 is targeted for degradation by high-risk, but not low-risk, HPV E6 proteins both in vitro and in vivo (FIG. 4). Furthermore, immortalization-competent, but not immortalization-incompetent HPV-16 E6 mutants target the E6TP1 protein for in vivo degradation (FIG. 5 and Table 2). These experiments strongly suggest that E6TP1 is involved in E6-induced immortalization and imply that this protein plays an important role in regulating biochemical pathways that ensure an untransformed phenotype of normal epithelial cells. See, e.g., Gao, et al., *Mol Cell Biol* 19: 733–744 (1999), which is incorporated herein by reference in its entirety.

TABLE 2

Mutational analysis of HPV16 E6 proteins to induce in vitro and in vivo degradation of E6TP1α

| Construct | Degradation in vitro | Degradation in vivo | Immortalization[a] |
|---|---|---|---|
| HPV16 E6 | + | + | 6 (6) |
| Lys-34 Glu | + | + | 3 (3) |
| Gln-35 Arg | + | ND[b] | 3 (3) |
| Ile-101 Val | + | ND[b] | 3 (3) |
| Tyr-84 Cys | + | + | 3 (3) |
| Cys-63 Ser | − | − | 1 (3) |

TABLE 2-continued

Mutational analysis of HPV16 E6 proteins to induce in vitro and in vivo degradation of E6TP1α

| Construct | Degradation in vitro | Degradation in vivo | Immortalization[a] |
|---|---|---|---|
| Cys-63 Arg/Tyr-70 Cys/Lys-72 Arg/Thr-86 Ser | – | – | 0 (4) |
| Cys-103 Arg/Asp-120 Gly/Ile-128 Met/Arg-131 Pro | – | – | 0 (4) |
| Gln-90 Arg/Cys-111 Arg/Glu-113 Stop | – | – | 0 (4) |

[a]All HPV16 E6 mutants and immortalization experiments are described in detail in Dalal et al., J Virol 70: 683–688, which is incorporated herein by reference in its entirety. Immortalization is shown as the number of experiments that yielded immortal cells. The numbers of experiments performed are in parentheses.
[b]ND, not done.

The ability of HPV E6 protein to bind and target E6TP1 for degradation is reminiscent of similar degradation of p53 tumor suppressor protein upon its indirect E6-AP-mediated interaction with E6. Previous analyses of E6-p53 interaction have suggested that E6-binding is sufficient to target bound proteins for degradation. In contrast, recently identified E6-binding proteins ERC55, paxillin, and hDlg have not been shown to undergo E6-induced degradation, supra. This result suggests that degradation is not an obligatory consequence of E6-binding. Notably, truncated mutants of E6TP1 that efficiently bound to E6 were not degraded. Thus, distinct regions of cellular target proteins may be crucial for E6 binding and E6-dependent targeting to cellular degradation machinery. E6-induced degradation of p53 is mediated through E6-AP, a ubiquitin ligase (see, e.g., Background Section), and E6 can simultaneously bind E6TP1 and E6-AP. Indeed, we have recently shown that the dominant negative E6-AP C833A mutant can inhibit E6 induced E6TP1 degradation in vivo in 293T cells.

Defined fragments of E6TP1 have obvious clinical applications, and the use of said fragments in treatment of both non-HPV-associated and HPV-associated diseases and carcinomas are discussed, infra. See, Therapeutics of the Invention Section.

The recently identified E6-binding protein, hDlg, was shown to utilize its PDZ domain to bind to E6. In contrast, E6TP1 requires its C-terminal 194 residues for its interaction with E6. Furthermore, when C-terminal 194 residues were deleted, E6TP1 could not bind to E6. Thus, E6TP1 PDZ domain does not contribute to E6-binding and would be available for other interactions. Given the ability of PDZ domains to mediate protein-protein interactions, we speculate that E6TP1-E6 complex may also include other proteins bound to E6TP1 PDZ domain. Thus, E6TP1 PDZ domain may help in localizing E6 to other cellular targets.

Similar to E6-AP, ERC55, paxillin, and hDlg, supra, E6TP1 selectively bound to high risk HPV E6 proteins in vitro. Furthermore, only high risk HPV E6 proteins promoted E6TP1 degradation in vitro and in vivo. In addition, E6TP1 binding and degradation were observed with E6 mutants that are competent at cellular immortalization but not with those mutants that fail to immortalize cells. Altogether, these results strongly argue that E6TP1, similar to other known E6-binding proteins, is a transformation-relevant target of HPV E6. It appears likely that an oncoprotein, such as E6, concurrently targets a number of cellular metabolic pathways en route to efficient transformation. Given multiple checkpoints that cells utilize to ensure proper cellular proliferation, the strategy of oncogenic viruses to target multiple cellular pathways is likely to reflect the natural tumorigenesis which is well documented to be a multi-step process.

In conclusion, we have identified a novel putative Rap-GAP as a cellular target of the high risk HPV E6 oncoproteins. Given that previously identified targets of HPV E6 and other DNA tumor virus oncogenes are tumor suppressor proteins, and several GAP proteins (such as tuberin and Neurofibromatosis type 1 (NF1) gene product) are known to function as tumor suppressors (see, e.g., Basu et al., Nature 356: 713–715 (1992); The European Chromosome 16 Tuberous Sclerosis Consortium, Cell 75: 1305–1315 (1993)), E6TP1 may represent a novel tumor suppressor protein whose inactivation contributes to oncogenesis. Localization of E6TP1 to chromosome 14q23.2–14q24.3, a site for loss of heterozygosity in malignant meningiomas further point to this possibility. See, e.g., Menon et al., Oncogene 14: 611–616 (1997); Simon et al., Cancer Res 55: 4696–4701 (1995); Tse et al, Hum Pathol 28: 779–785 (1997).

Definitions of Derivatives, Fragments, and Analogs

Derivatives, fragments, and analogs provided herein are defined as sequences of at least 6 (contiguous) nucleic acids or at least 4 (contiguous) amino acids, lengths sufficient to allow for specific hybridization in the case of nucleic acids or for specific recognition of an epitope in the case of amino acids, respectively. Fragments are, at most, one nucleic acid-less or one amino acid-less than the wild type full length sequence. Derivatives and analogs may be of any desired length, including full length, if said derivative or analog contains a modified nucleic acid or amino acid, as described infra. Derivatives and analogs of desired proteins may be those expressed in non-mammalian expression systems, such as in vitro translation in a cell free system (such as a wheat germ lysate, a rabbit reticulocyte lysate, and an E. coli extract) and baculovirus expression vectors transfected into insect cell lines. Homologs are proteins or protein fragments obtained from other species that have a substantial percent identity over conserved regions or domains, respectively, to the nucleic acid or protein sequence being compared. Homologues are presumed to have diverged from the same gene in a common ancestor of the species being compared. Homologs may have at least about 30%, 50%, 70%, 80%, or 95% identity in various embodiments. Percent identity can be determined through comparison or alignment of two protein or nucleic acid sequences using computer programs well known in the art, for e.g., Wisconsin GCG (Genetics Computer Group) software package using default parameter settings.

Derivatives or analogs of E6TP1 include, but are not limited to, molecules comprising regions that are substantially homologous to E6TP1 in various embodiments by at least about 30%, 50%, 70%, 80%, or 95% identity (with a preferred identity of 90–95%) over an amino acid sequence of identical size or when compared to an aligned sequence in which the alignment is done by, for e.g., a computer homology program well known in the art and using its default parameter settings, or whose encoding nucleic acid is capable of hybridizing to the complement (e.g., the inverse complement) of a sequence encoding E6TP1 under stringent (the preferred embodiment), moderately stringent, or low stringent conditions. See e.g., Ausubel, et al., Current Protocols in Molecular Biology, John Wiley & Sons, New York, N.Y., 1998, and infra. In a preferred embodiment of the present invention, the aforementioned fragments possess nucleotide or amino acid sequences which are comprised of at least 80% of the wild type, full length E6TP1 proteins or at least 80% of the nucleic acid sequences encoding these proteins, or with an overall 90% nucleic acid or amino acid sequence identity.

Identification and Isolation Novel E6TP1-IP genes

The present invention discloses methodologies for assaying and screening derivatives, fragments, analogs and homologs of E6TP1-interacting proteins ("E6TP1-IP") for binding to E6TP1. The derivatives, fragments, analogs and homologs of the E6TP1-IP that interact with E6TP1 may be identified by means of a yeast two hybrid assay system. See e.g., Chien et al., *Proc Natl Acad Sci USA* 88: 9578–9582 (1991); Fields & Song, *Nature* 340: 245–246 (1989).

The identification of interacting proteins by the improved yeast two hybrid system is based upon the detection of the expression of a reporter gene (hereinafter "Reporter Gene"), the transcription of which is dependent upon the reconstitution of a transcriptional regulator by the interaction of two proteins, each fused to one half of the transcriptional regulator. The bait E6TP1 (or derivative, fragment, analog or homolog) and prey protein (proteins to be tested for ability to interact with the bait protein) are expressed as fusion proteins to a DNA-binding domain, and to a transcriptional regulatory domain, respectively, or vice versa. In a specific embodiment of the present invention, the prey population may be one or more nucleic acids encoding mutants of E6TP1-IP (e.g., as generated by site-directed mutagenesis or another method of producing mutations in a nucleotide sequence). The prey populations are proteins encoded by DNA (e.g., cDNA, genomic DNA or synthetically generated DNA), said DNAs derived either from a specific gene of choice, or from cDNA libraries obtain from a cell type of interest. For example, the populations may be expressed from chimeric genes comprising cDNA sequences derived from a non-characterized sample of a population of cDNA from mammalian RNA. In another specific embodiment, recombinant biological libraries expressing random peptides may be used as the source of prey nucleic acids.

The present invention discloses methods for the screening for inhibitors of E6TP1-IP. In brief, the protein-protein interaction assay may be performed as previously described herein, with the exception that it is performed in the presence of one or more candidate molecules. A resulting increase or decrease in Reporter Gene activity, in relation to that which was present when the one or more candidate molecules are absent, indicates that the candidate molecule exerts an effect on the interacting pair. In a preferred embodiment, inhibition of the protein interaction is necessary for the yeast cells to survive, for example, where a non-attenuated protein interaction causes the activation of the URA3 gene, causing yeast to die in medium containing the chemical 5-fluoroorotic acid. See e.g., Rothstein, 1983. *Meth. Enzymol.* 101: 167–180.

In general, the proteins comprising the bait and prey populations are provided as fusion (chimeric) proteins, preferably by recombinant expression of a chimeric coding sequence containing each protein contiguous to a pre-selected sequence. For one population, the pre-selected sequence is a DNA-binding domain that may be any DNA-binding domain, so long as it specifically recognizes a DNA sequence within a promoter (e.g., a transcriptional activator or inhibitor). For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably, do not detectably interact, so as to avoid false-positives in the assay. The assay system further includes a reporter gene operably linked to a promoter that contains a binding site for the DNA-binding domain of the transcriptional activator (or inhibitor). Accordingly, in the practice of the present invention, the binding of E6TP1 fusion protein to a prey fusion protein leads to reconstitution of a transcriptional activator (or inhibitor), which concomitantly activates (or inhibits) expression of the Reporter Gene.

In a specific embodiment, the present invention discloses a methodology for detecting one or more protein-protein interactions comprising the following steps: (i) recombinantly-expressing E6TP1 (or a derivative, fragment, analog or homolog thereof) in a first population of yeast cells of a first mating type and possessing a first fusion protein containing E6TP1 sequence and a DNA-binding domain; wherein said first population of yeast cells contains a first nucleotide sequence operably-linked to a promoter that is "driven" by one or more DNA-binding sites recognized by said DNA-binding domain such that an interaction of said first fusion protein with a second fusion protein (comprising a transcriptional activation domain) results in increased transcription of said first nucleotide sequence; (ii) negatively selecting to eliminate those yeast cells in said first population in which said increased transcription of said first nucleotide sequence occurs in the absence of said second fusion protein; (iii) recombinantly expressing in a second population of yeast cells of a second mating type different from said first mating type, a plurality of said second fusion proteins; wherein said second fusion protein is comprised of a sequence of a derivative, fragment, analog or homolog of a E6TP1-IP and an activation domain of a transcriptional activator, in which the activation domain is the same in each said second fusion protein; (iv) mating said first population of yeast cells with said second population of yeast cells to form a third population of diploid yeast cells, wherein said third population of diploid yeast cells contains a second nucleotide sequence operably linked to a promoter "driven" by a DNA-binding site recognized by said DNA-binding domain such that an interaction of a first fusion protein with a second fusion protein results in increased transcription of said second nucleotide sequence, in which the first and second nucleotide sequences can be the same or different and (v) detecting said increased transcription of said first and/or second nucleotide sequence, thereby detecting an interaction between a first fusion protein and a second fusion protein.

In a preferred embodiment, the bait (an E6TP1 sequence) and the prey (a library of chimeric genes) are combined by mating the two yeast strains on solid media for a period of approximately 6–8 hours. In a less preferred embodiment, the mating is performed in liquid media. In an alternative embodiment, the bait comprises a library of chimeric genes and the prey comprises an E6TP1 sequence. The resulting diploids contain both types of chimeric genes (i.e., the DNA-binding domain fusion and the activation domain fusion). After an interactive population is obtained, the DNA sequences encoding the pairs of interactive proteins are isolated by a method wherein either the DNA-binding domain hybrids or the activation domain hybrids are amplified, in separate reactions. Preferably, the amplification is carried out by polymerase chain reaction (PCR; see e.g., Innis, et al., 1990. PCR Protocols, Academic Press, Inc., San Diego, Calif.) utilizing pairs of oligonucleotide primers specific for either the DNA-binding domain hybrids or the activation domain hybrids. The PCR amplification reaction may also be performed on pooled cells expressing interacting protein pairs, preferably pooled arrays of interactants. Other amplification methods known within the art may also be used. See e.g., Kricka, et al., 1995. Molecular Probing, Blotting, and Sequencing, Academic Press, New York, N.Y.

In an additional embodiment of the present invention, the plasmids encoding the DNA-binding domain hybrid and the activation domain hybrid proteins may also be isolated and cloned by any of the methods well-known within the art. For example, but not by way of limitation, if a shuttle (yeast to E. coli) vector is used to express the fusion proteins, the genes may be subsequently recovered by transforming the yeast DNA into E. coli and recovering the plasmids from the bacteria. See e.g., Hoffman, et al., 1987. *Gene* 57: 267–272.

E6TP1 and Novel E6TP1-IP Genes

The present invention relates to the nucleotide sequences encoding a human E6TP1 protein. See, e.g., supra. The present invention also relates to the nucleotide sequences encoding an E6TP1 interacting protein ("E6TP1-IP"). In specific embodiments, the E6TP1 nucleic acid sequence comprises the sequence of SEQ ID NOS: 1 or 3, or a portion thereof, or a nucleotide sequence encoding, in whole or in part, an E6TP1 protein (e.g., a protein comprising the amino acid sequence of SEQ ID NOS: 2 and 4, or a portion thereof). The invention provides purified nucleic acids consisting of at least 6 nucleotides (i.e., a hybridizable portion) of an E6TP1 sequence. In other embodiments, the nucleic acids consist of at least about 25, 50, 100, 500, 1000, 3000 or 6000 (continuous) nucleotides of an E6TP1 gene sequence, or a full-length E6TP1 gene sequence. In another embodiment, the nucleic acids are smaller than about 35, 200, 500, 1000 or 6000 nucleotides in length. Nucleic acids can be single or double stranded.

Nucleic acid molecules encoding derivatives and analogs of E6TP1 and E6TP1-IP proteins, or antisense nucleic acids to the same (see, e.g, infra), are additionally provided. As is readily apparent, as used herein, a "nucleic acid encoding a fragment or portion of E6TP1 and E6TP1-IP proteins" shall be construed as referring to a nucleic acid encoding only the recited fragment or portion of the E6TP1 and E6TP1-IP proteins, and not the other contiguous portions of the E6TP1 as a continuous sequence.

The invention also relates to nucleic acids hybridizable to or complementary to the foregoing sequences, in particular the invention provides the inverse complement to nucleic acids hybridizable to the foregoing sequences (i.e., the inverse complement of a nucleic acid strand has the complementary sequence running in reverse orientation to the strand so that the inverse complement would hybridize with little or no mismatches to the nucleic acid strand). In specific aspects, nucleic acid molecules are provided which comprise a sequence complementary to (specifically are the inverse complement of) at least about 10, 25, 50, 100, or 200 nucleotides or the entire coding region of an E6TP1 gene or an E6TP1-IP gene.

In a specific embodiment, a nucleic acid sequence which is hybridizable to an E6TP1-IP nucleic acid sequence (or a complement of the foregoing), or to a nucleic acid sequence encoding a derivative of the same, under conditions of high stringency is provided. It should be noted that the most preferred embodiment of the present invention utilizes high stringency hybridization conditions. By way of example and not limitation, procedures using such conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5–20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which may be used are well known in the art. See, e.g., Ausubel et al. (eds.), 1998, Current Protocols in Molecular Biology, John Wiley & Sons, NY; and Kriegler, 1990, Gene Transfer and Expression, a Laboratory Manual, Stockton Press, NY.

In another specific embodiment, a nucleic acid sequence which is hybridizable to an E6TP1-IP nucleic acid sequence or to a nucleic acid sequence encoding an E6TP1-IP derivative (or a complement of the foregoing) under conditions of moderate stringency is provided. For example, but not limited to, procedures using such conditions of moderate stringency are as follows: Filters containing DNA are pretreated for 6 hours at 55° C. in a solution containing 6×SSC, 5×Denhardt's solution, 0.5% SDS and 100 µg/ml denatured salmon sperm DNA. Hybridizations are carried out in the same solution with 5–20×10$^6$ cpm $^{32}$P-labeled probe. Filters are incubated in hybridization mixture for 18–20 hours at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 hour in a solution containing 2×SSC, 0.1% SDS. Other conditions of moderate stringency which may be used are well known in the art. See, e.g., Ausubel et al. (eds.), 1998, Current Protocols in Molecular Biology, John Wiley & Sons, NY; and Kriegler, 1990, Gene Transfer and Expression a Laboratory Manual, Stockton Press, NY.

In another specific embodiment, a nucleic acid that is hybridizable to an E6TP1-IP nucleic acid sequence (e.g., having sequence SEQ ID NOS: 1 and 3), or to a nucleic acid sequence encoding an E6TP 1-IP protein derivative (or a complement of the foregoing), under conditions of low stringency, is provided. By way of example and not limitation, procedures using such conditions of low stringency are as follows (see also Shilo and Weinberg, 1981, *Proc Natl Acad Sci USA* 78: 6789–6792): Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe. Filters are incubated in hybridization mixture for 18–20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations). See, e.g., Ausubel et al. (eds.), 1998, Current Protocols in Molecular Biology, John Wiley & Sons, NY; and Kriegler, 1990, Gene Transfer and Expression, a Laboratory Manual, Stockton Press, NY.

Within nucleotide sequences, potential open reading frames can be identified using the NCBI BLAST program ORF Finder available to the public. Because all known protein translation products are at least 60 amino acids or longer (Creighton, 1992, Proteins, 2nd Ed., W.H. Freeman and Co., New York), only those ORFs potentially encoding a protein of 60 amino acids or more are considered. If an initiation methionine codon (ATG) and a translational stop codon (TGA, TAA, or TAG) are identified, then the boundaries of the protein are defined. Other potential proteins include any open reading frames that extend to the 5' end of the nucleotide sequence, in which case the open reading frame predicts the C-terminal or core portion of a longer protein. Similarly, any open reading frame that extends to the 3' end of the nucleotide sequence predicts the N-terminal portion of a longer protein.

Any method available in the art can be used to obtain a full length (i.e., encompassing the entire coding region) cDNA clone encoding an E6TP1 protein. In particular, the polymerase chain reaction (PCR) can be used to amplify sequences from a cDNA library. Oligonucleotide primers that hybridize to sequences at the 3' and 5' termini of the identified sequences can be used as primers to amplify by PCR sequences from a nucleic acid sample (cDNA or genomic DNA), preferably a cDNA library, from an appropriate source (e.g., the sample from which the initial cDNA library for the modified yeast two hybrid assay fusion population was derived, or, e.g. the genomic DNA of the same). PCR can be carried out, e.g., by use of a thermal cycler and Taq polymerase.

The DNA being amplified can include genomic DNA or cDNA sequences from any eukaryotic species. One can choose to synthesize several different degenerate primers for use in the PCR reactions. It is also possible to vary the stringency of hybridization conditions used in priming the PCR reactions to amplify nucleic acid homologs (e.g., to obtain E6TP1-IP sequences from species other than humans, or to obtain human sequences with homology to E6TP1-IP) by allowing for greater or lesser degrees of nucleotide sequence similarity between the known nucleotide sequence and the nucleic acid homolog being isolated.

After successful amplification of a nucleic acid containing all or a portion of an E6TP1-IP sequence, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, the nucleotide sequence of the entire E6TP1-IP gene, as well as additional genes encoding an E6TP1-IP protein or analog, may be identified.

Any eukaryotic cell potentially can serve as the nucleic acid source for the molecular cloning of an E6TP1-IP gene. The nucleic acids can be isolated from vertebrates, including human and other primate sources, porcine, bovine, feline, avian, equine, canine, as well as additional mammalian sources, and insects, plants, etc. The DNA may be obtained by standard procedures known in the art from cloned DNA (e.g, a DNA "library"), by chemical synthesis, by cDNA cloning, or by the cloning of genomic DNA, or fragments thereof, purified from the desired cell. See, e.g, Sambrook et al., 1989, Molecular Cloning, a Laboratory Manual, 2d Ed., Cold Spring Harbor Laboratory Press, Cold Spring Harbor, N.Y.; and Glover (ed.), 1985, DNA Cloning: a Practical Approach, MRL Press, Ltd., Oxford, U.K. Vol. I, II). Clones derived from genomic DNA may contain regulatory and intronic DNA regions in addition to coding regions; clones derived from cDNA will contain only exon sequences. In the production of a gene encoding a derivative or analog of E6TP1, care should be taken to ensure that the modified gene retains the original translational reading frame, uninterrupted by translational stop signals. Other methods are possible and within the scope of the invention. Whatever the source, the identified and isolated nucleic acids can then be molecularly cloned into a suitable cloning vector for propagation of the gene.

Cloned E6TP1 gene sequence can be modified by any of numerous strategies known in the art. See, e.g., Ausubel et al. (eds.), Current Protocols in Molecular Biology, Wiley & Sons, NY (1998). The sequences can be cleaved at appropriate sites with restriction endonuclease(s), modified further by enzymatic manipulation if desired, isolated, and ligated in vitro.

Identification of the specific DNA fragment containing the desired gene may be accomplished in a number of ways. For example, a portion of the E6TP1-IP gene (of any species) (e.g., a PCR amplification product or an oligonucleotide encoding a portion of the known nucleotide sequence) or its specific RNA, or a fragment thereof, may be purified and labeled, then used as a probe to screen a desired DNA population. See, e.g, Benton and Davis, 1977, Science 196: 180–182; Grunstein and Hogness, 1975, Proc. Natl. Acad. Sci. U.S.A. 72: 3961–3964. Those DNA fragments with substantial homology to the probe will hybridize. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties or ability to bind E6TP1, as is known for E6TP1. If an anti-E6TP1 antibody is available, the protein may be identified by binding of labeled antibody to the putative E6TP1 synthesizing clones, in an ELISA (enzyme-linked immunosorbent assay)-type procedure.

In specific embodiments, transformation of host cells with recombinant DNA molecules that incorporate the isolated E6TP1-IP gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

Expression and Purification: Recombinant Methodologies

E6TP1 or E6TP1-IP nucleic acids can be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the pBlueScript vector (Stratagene, La Jolla, Calif.). Insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically "polished" to ensure compatibility. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and the E6TP1 gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

Additionally, the E6TP1 encoding nucleotide sequence can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Any technique for mutagenesis known in the art can be used, including but not limited to, chemical mutagenesis and in vitro site-directed mutagenesis (see, e.g., Hutchinson et al., 1978, *J Biol Chem* 253: 6551–6558), and the like.

For recombinant expression of one or more of the proteins, the nucleic acid containing all or a portion of the nucleotide sequence encoding the protein can be inserted into an appropriate expression vector, i.e., a vector that contains the necessary elements operably linked for the transcription and translation of the inserted protein coding sequence. The necessary transcriptional and translational signals can also be supplied by the native promoter for E6TP1 or E6TP1-IP genes, and/or their flanking regions.

In a specific embodiment, a vector is used that comprises a promoter operably linked to nucleotide sequences encoding E6TP 1, or a fragment, derivative or homolog thereof, one or more origins of replication, and optionally, one or more selectable markers (e.g., an antibiotic resistance gene).

Promoters which may be used include but are not limited to: (a) strong promoters able to direct high levels of transcription initiation, including but not limited to viral promoters such as SV40 early promoter (Bemoist and Chambon, 1981, *Nature* 290: 304–310) or the Rous sarcoma virus 3' long terminal repeat promoter (Yamamoto et al., 1980, *Cell* 22: 787–797); (b) promoters that direct ubiquitous expression in all tissues, including but not limited to the Herpes thymidine kinase promoter (Wagner et al, 1981, *Proc Natl Acad Sci USA* 78: 1441–1445), the prokaryotic β-lactamase promoter (Villa-Kamaroff et al., 1978, *Proc Natl Acad Sci USA* 75: 3727–3731) or the tac promoter (DeBoer et al, 1983, *Proc Natl Acad Sci USA* 80: 21–25); (c) plant expression vectors, including but not limited to the nopaline synthetase promoter (Herrar-Estrella et al., 1984, *Nature* 303: 209–213) or the cauliflower mosaic virus 35S RNA promoter (Garder et al. 1981, *Nucleic Acids Res.* 9: 2871); (d) promoter elements from yeast and other fungi, including but not limited to the Gal4 promoter, the alcohol dehydrogenase promoter, the phosphoglycero kinase promoter, the alkaline phosphatase promoter; and (e) animal transcriptional control regions that exhibit tissue specificity, including but not limited to the elastase I gene (see, e.g., *Cold Spring Harbor Symp Quant Biol* 50: 399–409; MacDonald 1987, *Hepatology* 7: 425–515), insulin gene (see, e.g., Hanahan et al., 1985, *Nature* 315: 115–122), immunoglobulin gene (see, e.g., Alexander et al., 1987, *Mol Cell Biol* 7: 1436–1444), albumin gene (see, e.g., Pinckert et al., 1987, *Genes Dev.* 1: 268–276), beta globin gene (see, e.g., Kollias et al., 1986, *Cell* 46: 89–94), myelin basic protein gene (see, e.g., Readhead et al., 1987, *Cell* 48: 703–712), and gonadotrophic releasing hormone gene (see, e.g., Mason et al., 1986, *Science* 234: 1372–1378).

Expression vectors containing the sequences of interest can be identified by three general approaches: (a) nucleic acid hybridization, (b) presence or absence of marker gene function, (c) expression of the inserted sequences, and (d) by restriction enzyme digestion(s) or by direct DNA sequence analysis. In the first approach, E6TP1 sequences can be detected by nucleic acid hybridization to probes comprising sequences homologous and complementary to the inserted sequences. In the second approach, the recombinant vector/host system can be identified and selected based upon the presence or absence of certain marker functions (e.g., binding to an anti-E6TP1, or anti-E6TP1-IP complex antibody, resistance to antibiotics, occlusion body formation in baculovirus, etc.) caused by insertion of the sequences of interest in the vector. For example, if an E6TP1 gene, or portion thereof, is inserted within the marker gene sequence of the vector, recombinants containing the E6TP1 fragment will be identified by the absence of the marker gene function. In the third approach, recombinant expression vectors can be identified by assaying for E6TP1 products expressed by the recombinant vector. Such assays can be based, for example, on the physical or functional properties of the interacting species in in vitro assay systems, e.g., formation of an E6TP1 complex or immunoreactivity to antibodies specific for the protein. In a fourth approach, recombinant expression vectors can be identified by digesting the appropriate fragment with restriction enzyme(s) and comparing the fragment sizes with those expected according to a known restriction map if such is available, or by DNA sequence analysis and comparison to the known nucleotide sequence of an E6TP1-IP.

Once recombinant E6TP1 molecules is identified and the complexes or individual proteins are isolated, several methods known in the art can be used to propagate them. To wit, expression vectors or derivatives that can be used include, but are not limited to, human or animal viruses such as vaccinia virus or adenovirus; insect viruses such as baculovirus; yeast vectors; bacteriophage vectors such as lambda phage; plasmids such as pBR322, pUC plasmid derivatives, or the pBlueScript vector (Stratagene, La Jolla, Calif.); and cosmid vectors. Methods used may include in vitro recombinant DNA and synthetic techniques and in vivo recombinants (genetic recombination). Any suitable transcription and translation elements may be used, and expression may be regulated by any promoter and or enhancer known in the art. Promoters sources which may be used include, but are not limited to, viral, mammalian, prokaryotic, and plant promoters, and promoter element from yeast and other fungi. Transcriptional control regions may exhibits tissue specificity or ubiquitous expression. Positive clones may be identified by any method known in art. See e.g. Ausubel, et al., Current Protocols in Molecular Biology, John Wiley & Sons, New York, N.Y., (1998).

A variety of host-vector systems may be utilized to express the protein coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of vectors vary in their strengths and specificities. Depending on the host-vector system utilized, any one of a number of suitable transcription and translation elements may be used.

Different host cells have characteristic and specific mechanisms for the translational and post-translational processing and modification (e.g., glycosylation, prenylation, acetylation, phosphorylation) of proteins. Appropriate cell lines or host systems can be chosen to ensure the desired modification and processing of the introduced protein is achieved. Depending on the host-vector system utilized, any one of a number of suitable transcription and translation elements may be used, See, e.g., supra.

In addition, a host cell strain may be chosen that modulates the expression of the inserted sequence, or modifies or processes the expressed protein in the specific fashion desired. Expression from certain promoters can be elevated in the presence of certain inducers; thus, expression of the genetically-engineered E6TP1 may be controlled. Furthermore, different host cells have characteristic and specific mechanisms for the translational and post-translational processing and modification (e.g., glycosylation, phosphorylation, etc.) of proteins. Appropriate cell lines or host systems can be chosen to ensure the desired modification and processing of the foreign protein is achieved. For example, expression in a bacterial system can be used to produce an unglycosylated core protein, while expression in mammalian cells can ensure native glycosylation of a heterologous mammalian protein. Furthermore, different vector/host expression systems may effect processing reactions to different extents.

Once a recombinant cell expressing E6TP1 protein, or fragment or derivative thereof, is identified, the individual gene product or complex can be isolated and analyzed. This is achieved by assays based upon the physical and/or functional properties of the protein or complex, including, but not limited to, radioactive labeling of the product followed by analysis by gel electrophoresis, immunoassay, cross-linking to marker-labeled products, and the like. The E6TP1 protein may be isolated and purified by standard methods known in the art (either from natural sources or recombinant host cells expressing the proteins/protein complexes) including, but not limited to, column chromatography (e.g., ion exchange, affinity, gel exclusion, reverse-phase, high pressure, fast protein liquid, etc.), differential centrifugation, differential solubility, or similar methodologies used for the purification of proteins. Alternatively, once E6TP1 protein or its derivative is identified, the amino acid sequence of the protein can be deduced from the nucleic acid sequence of the chimeric gene from which it was encoded. Hence, the protein or its derivative can be synthesized by standard chemical methodologies known in the art. See, e.g., Hunkapiller, et al., *Nature* 310: 105–111 (1984).

Identification and Isolation of E6TP1 and Novel E6TP1-IP Proteins

The present invention relates to E6TP1 and E6TP1-IP proteins as well as derivatives, fragments, homologs and analogs thereof, wherein the native proteins, fragments, derivatives or analogs of said novel proteins are from humans. In other specific embodiments, the fragment, derivative or analog is functionally active, i.e., capable of exhibiting one or more functional activity associated with wild type E6TP1 protein, e.g., antigenicity, immunogenicity, or ability to bind E6 protein. The E6TP1 and E6TP1-IP nuclear acid sequences provided by the present invention includes those nucleotide sequences encoding substantially the same amino acid sequence as found in the respective native protein, those encoded amino acid sequences with functionally equivalent amino acids, and those sequences encoding other E6TP 1 and E6TP1-IP derivatives or analogs, as described herein.

The E6TP1 proteins, either alone or in a complex, can be isolated and purified by standard methods known in the art, including but not restricted to column chromatography (e.g., ion exchange, affinity, gel exclusion, reversed-phase high pressure, fast protein liquid, etc.), differential centrifugation, differential solubility, or by any other standard technique used for the purification of proteins. Starting material may be either from natural sources or recombinant host cells expressing the complexes or proteins. Compositions comprising an E6TP1 protein, or an E6TP1-IP complex may be purified to as little as 5% homogeneity, from about 5%, 20%, 50%, 80%, to 90% homogeneity, or from about 70%, 80%, 90%, to 100% homogeneity. Alternatively, a protein or its derivative can be synthesized by standard chemical methods known in the art. See, e.g., Hunkapiller et al., *Nature* 310: 105–111 (1984). Functional properties may be evaluated using any suitable assay known in the art. See, e.g., Methods in Enzymology, Abelson, (Ed.), Academic Press (1993).

In a preferred embodiment, a complex of an E6TP1 protein and an E6TP1-IP protein (herefouth designated "E6TP1:E6TP1-IP") is obtained by expressing the entire E6TP1 coding sequence and an E6TP1-IP coding sequence in the same cell, either under the control of the same promoter or under two separate promoters. In yet another embodiment, a derivative, fragment or homolog of E6TP1 and/or a derivative, fragment or homolog of an E6TP1-IP are recombinantly expressed. Preferably the derivative, fragment or homolog of E6TP1 and/or of the E6TP1-IP protein forms a complex with a binding partner identified by a binding assay, such as the modified yeast two hybrid system (see e.g. Chien, et al., 1991, *Proc Natl Acad Sci USA*. 88: 9578–9581), and more preferably forms a complex that binds to an anti-E6TP1 antibody.

The E6TP1 derivatives and analogs of the invention can be produced by various methods known in the art. The manipulations that result in their production can occur at the gene or protein level. Alternately, on the protein level, E6TP1 fragments, derivatives, or analogs may be made by a protein synthesis technique, e.g., by use of a peptide synthesizer. Manipulations of E6TP1 sequences may be made at the protein level (e.g. post-translational).

Included within the scope of the invention are derivatives of complexes of E6TP1 fragments, derivatives or analogs thereof that are differentially modified during or after translation, e.g., by glycosylation, acetylation, phosphorylation, amidation, prenylation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH4, acetylation, formylation, oxidation, reduction, metabolic synthesis in the presence of tunicamycin, etc.; acetylation; formylation; oxidation; reduction; or modification by metabolic processes.

E6TP1 derivatives can be made by altering their respective sequence by substitutions, additions or deletions that provide for functionally equivalent molecules. Due to the degeneracy of nucleotide coding sequences, other DNA sequences that encode substantially the same amino acid sequence as an E6TP1 gene can be used in the practice of the present invention. Said nucleotide sequences may be altered by the substitution of different codons that encode the same amino acid residue within the sequence, thus producing a silent change. Substitute codons for an amino acid within the sequence may be selected from other members of the class to which the amino acid belongs. For example, E6TP1 variants in the present invention may have conservative amino acid substitutions selected from nonpolar (hydrophobic), polar neutral, positively charged (basic), and negatively charged (acidic) amino acids.

Likewise, E6TP1 derivatives of the invention include, but are not limited to, those containing, as a primary amino acid sequence, all or part of the amino acid sequence of E6TP1, including altered sequences in which functionally equivalent amino acid residues are substituted for residues within the sequence resulting in a silent change. Variants comprising conservative amino acid substitutions within the polypeptide sequence are also representative of the invention. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In specific embodiments, the E6TP1 protein sequences are modified to include a fluorescent label or to have a heterofunctional reagent; such heterofunctional reagents may be used to crosslink the protein to other members of the complex or to other E6TP1-IPs, or if desired, contain non-classical amino acids or chemical amino acid analogs introduced as a substitution or addition into the E6TP1 and/or an E6TP1-IP. Non-classical amino acids include but are not limited to amino isobutyric acid, 3-amino propionoic acid, ornithine, norleucine, norvaline, hydroxyproline, sarcosine, citrulline, cysteic acid, t-butylglycine, t-butylalanine, phenylglycine, cyclohexylalanine, fluoro-amino acids, C-methyl amino acids, N-methyl amino acids, designer amino acids and amino acid analogs in general. Furthermore, classical or non-classical amino acids can be D (dextrorotary) or L (levorotary).

In addition, analogs and derivatives of E6TP1, or analogs and derivatives of E6TP1-IP protein, can be chemically synthesized. For example, a peptide corresponding to a portion of E6TP1 that comprises the desired domain or mediates the desired activity in vitro (e.g., E6TP1:E6TP1-IP complex formation) can be synthesized by use of a peptide synthesizer. Furthermore, if desired, non-classical amino acids or chemical amino acid analogs can be introduced as a substitution or addition into E6TP1. In addition, non-classical amino acids include but are not limited to the D-isomers of the common amino acids, amino isobutyric acid, 4-aminobutyric acid (4-Abu), 2-aminobutyric acid (2-Abu), 6-amino hexanoic acid (e-Ahx), 2-amino isobutyric acid (Aib), 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, C-methyl amino acids, N-methyl amino acids, and amino acid analogs in general.

Any of the methods described herein for the insertion of DNA fragments into a vector may be used to construct expression vectors containing a chimeric gene consisting of appropriate transcriptional and/or translational control signals and protein coding sequences. These methods may include in vitro recombinant DNA and synthetic techniques and in vivo recombinants (genetic recombination). Expression of nucleotide sequences encoding E6TP1, or a derivative, fragment or homolog thereof, may be regulated by a second nucleotide sequence so that the gene or gene fragment thereof is expressed in a host transformed with the recombinant DNA molecule(s). For example, expression of the proteins may be controlled by any promoter/enhancer known in the art. In a specific embodiment, the promoter is not native to the gene for E6TP1.

Chimeric genes comprising portions of E6TP1 fused to any heterologous protein-encoding sequences may be constructed. DNA fragments may be used to construct a chimeric gene in an expression vector using recombinant methodologies well known in the art.

In a specific embodiment, chimeric or fusion proteins are provided that contain the interacting domains of the E6TP1 protein and HPV E6 or any other protein known in the art (for e.g., Gal4 used in the yeast two hybrid system, or a β-galactosidase protein domain used for expression markers). In another specific embodiment, the E6TP1, or fragment, homolog or derivative thereof, may be expressed as a fusion or chimeric protein product comprising the E6TP1 protein, fragment, homolog, or derivative joined via a peptide bond to a protein sequence of an E6TP1-IP. In an optional embodiment, the fusion protein comprises the interacting domains of the E6TP1 and the E6TP1-IP proteins. In addition, a heterofunctional reagent, such as a peptide linker between the two domains, where such a reagent promotes the interaction of the E6TP1 and E6TP1-IP binding domains. E6TP1 fusion proteins may be particularly useful where the stability of the interaction is desirable (due to the formation of the complex as an intra-molecular reaction), for example in production of antibodies specific to E6TP1 or the E6TP1-E6 complex. In another specific embodiment, fusion proteins are provided that contain the interacting domains of both the E6TP1 protein and a known heterofunctional protein, such as a protein known to bind specific tissues or tissue-specific cell surface markers.

Said chimeric products can be made by ligating the appropriate nucleic acids encoding the desired amino acids to each other in the proper coding frame by methods known in the art, and expressing the chimeric products in a suitable host by methods commonly known in the art. Alternatively, such a chimeric product can be made by protein synthesis techniques, e.g., by use of a peptide synthesizer.

E6TP1 and E6TP1-IP derivatives can be made by altering their respective sequence by substitutions, additions or deletions that provide for functionally equivalent molecules. Due to the degeneracy of nucleotide coding sequences, other DNA sequences that encode substantially the same amino acid sequence as an E6TP1 or E6TP1-IP gene can be used in the practice of the present invention.

In a specific embodiment of the invention, proteins consisting of or comprising a fragment of E6TP1 or E6TP1-IP comprising at least 6 (continuous) amino acids of E6TP1 or E6TP1-IP are provided. In other embodiments, the fragment consists of at least about 10, 20, 30, 40, or 50 amino acids of E6TP1 or E6TP1-IP. In specific embodiments, such fragments are not larger than about 35, 100 or 200 amino acids. Derivatives or analogs of E6TP1 or E6TP1-IP include, but are not limited to, molecules comprising regions that are substantially homologous to E6TP1 or E6TP1-IP, in various embodiments, by at least about 30%, and ranging up to 50%, 70%, 80% or 99% identity (with a preferred identity of 90–95% ) over an amino acid sequence of identical size or when compared to an aligned sequence in which the alignment is done by a computer homology program known in the art. In another embodiment, derivatives or analogs of E6TP1 or E6TP1-IP may differ by as little as one chemical moiety or side group. Derivatives or analogs of E6TP1-IP whose encoding nucleic acid is capable of hybridizing to the complement (e.g., the inverse complement) of a sequence encoding E6TP1-IP under stringent, moderately stringent, or nonstringent conditions, as described supra, are also provided.

In a specific embodiment of the present invention, an E6TP1 or E6TP1-IP protein, whether produced by recombinant DNA techniques, chemical synthesis methods, or by purification from native sources, include but are not limited to those containing as a primary amino acid sequence all or part of the amino acid sequences substantially as shown in FIG. 2 [SEQ ID NOS:2 and 4], as well as fragments and other analogs and derivatives thereof, including proteins homologous thereto.

In cases where natural products are suspected of being mutant or are isolated from new species, the amino acid sequence of E6TP1 or E6TP1-IP isolated from the natural source, as well as those expressed in vitro, or from synthesized expression vectors in vivo or in vitro, can be determined from analysis of the DNA sequence, or alternatively, by direct sequencing of the isolated protein. Such analysis may be performed by manual sequencing or through use of an automated amino acid sequencer.

Alternatively, once an E6TP1-IP or its derivative is identified, the amino acid sequence of the protein can be deduced from the nucleotide sequence of the chimeric gene from which it was encoded. As a result, the protein or its derivative can be synthesized by standard chemical methods known in the art. See, e.g, Hunkapiller et al., *Nature* 310: 105–111 (1984).

Figure 7:
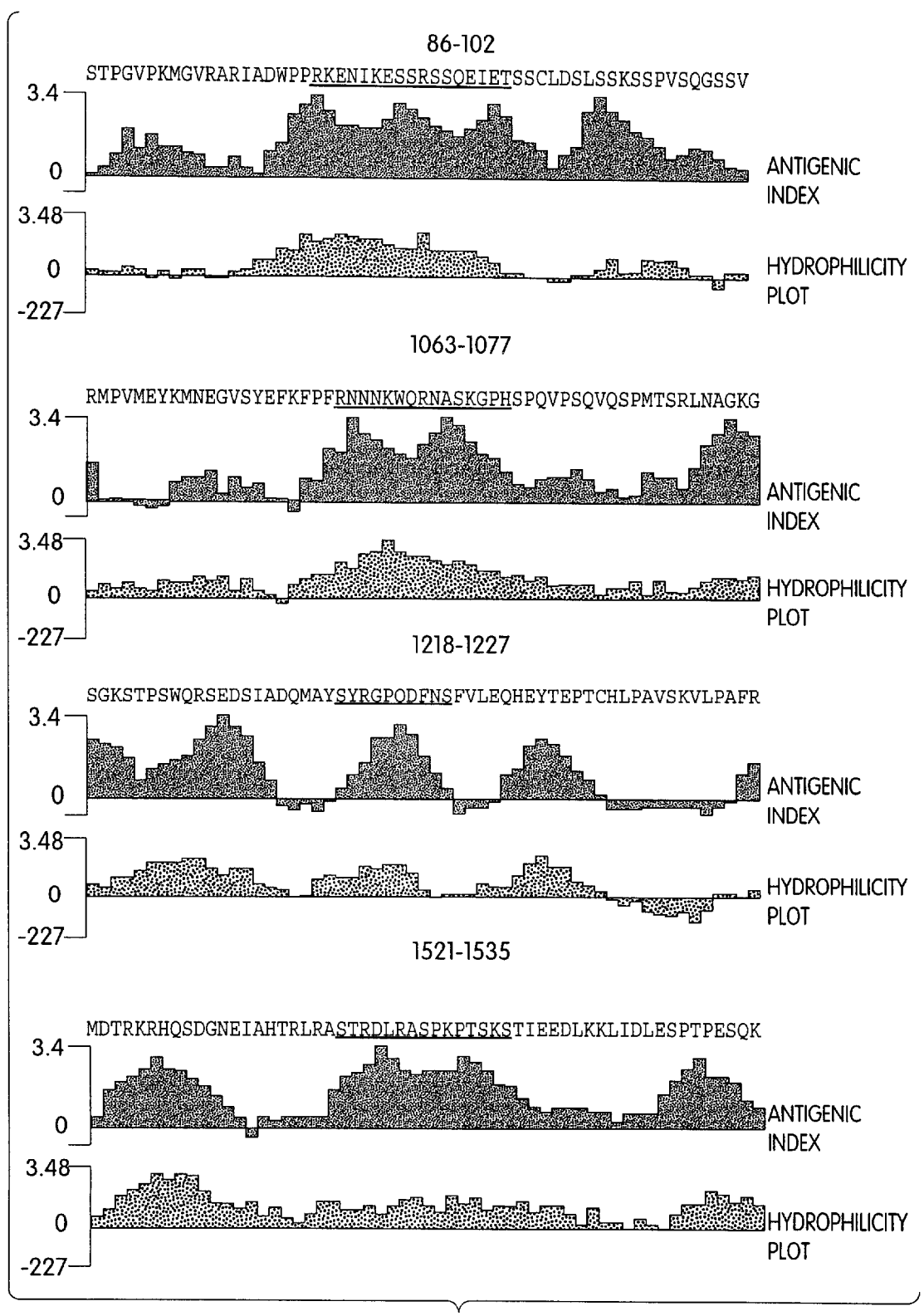
FIG. 7 illustrates a hydrophilicity and antigenicity plot of the E6TP1 polypeptide, wherein the underlined residues represent four peptides that will be used in the further production of polyclonal and monoclonal antibodies.

The E6TP1 or E6TP1-IP protein may also be analyzed by hydrophilicity analysis (FIG. 7). See, e.g., Hopp and Woods, *Proc Natl Acad Sci USA* 78: 3824–3828 (1981). A hydrophilicity profile can be used to identify the hydrophobic and hydrophilic regions of the proteins, and help predict their orientation to aid in the design of substrates for experimental manipulation, such as in binding experiments, antibody synthesis, etc. Secondary structural analysis can also be done to identify regions of the or E6TP1-IP protein that assume specific structures. See, e.g., Chou and Fasman, *Biochemistry* 13: 222–223 (1974). Manipulation, translation, secondary structure prediction, hydrophilicity and hydrophobicity profiles, open reading frame prediction and plotting, and determination of sequence homologies, can be accomplished using computer software programs available in the art.

Other methods of structural analysis including but not limited to X-ray crystallography (see, e.g., Engstrom, *Biochem. Exp. Biol.* 11: 7–13 (1974)), mass spectroscopy and gas chromatography (see, e.g., Methods in Protein Science, J. Wiley and Sons, New York, (1997)), and computer modeling (see, e.g., Fletterick and Zoller, eds., "Computer Graphics and Molecular Modeling", In: Current Communications in Molecular Biology, Cold Spring Harbor Laboratory, Cold Spring Harbor Press, New York (1986)) can also be employed.

Methodologies for Screening

The present invention provides methodologies for screening E6TP1, E6TP1-IP, and/or E6TP1:E6TP1-IP complexes, as well as derivatives, fragments and analogs thereof, for the ability to alter and/or modulate cellular functions, particularly those functions in which E6TP1 and/or E6TP1-IP have been implicated. For purposes of describing the present invention, a HPV E6 protein shall herein be deemed one possible E6TP1-IP protein, and be one possible participant in an E6TP1:E6TP1-IP complex. These functions include, but are not limited to, control of cell-cycle progression; regulation of transcription; control of intracellular signal transduction; and pathological processes, as well as various other biological activities (e.g., binding to an anti-E6TP1, anti-E6TP1-IP, and/or anti-E6TP1:E6TP1-IP complex antibody, and the like). The derivatives, fragments or analogs that possess the desired immunogenicity and/or antigenicity may be utilized in immunoassays, for immunization, for inhibition of E6TP1, E6TP1-IP, and/or E6TP1:E6TP1-IP complex activity, etc. For example, derivatives, fragments or analogs that retain, or alternatively lack or inhibit, a given property of interest (e.g., participation in a E6TP1:E6TP1-IP complex) may be utilized as inducers, or inhibitors, respectively, of such a property and its physiological correlates. In a specific embodiment, a E6TP1:E6TP1-IP complex of a fragment of the E6TP1 and/or a fragment of E6TP1-IP that can be bound by an anti-E6TP1 and/or anti-E6TP1-IP antibody or antibody specific for a E6TP1:E6TP1-IP complex when such a fragment is included within a given E6TP1:E6TP1-IP complex. Derivatives, fragments and analogs of E6TP1:E6TP1-IP complex may be analyzed for the desired activity or activities by procedures known within the art.

Production of Antibodies to the E6TP1:E6TP1-IP Complex

As disclosed by the present invention herein, E6TP1 protein, E6TP1-IP protein, or E6TP1:E6TP1-IP complex, or derivatives, fragments, analogs or homologs thereof, may be utilized as immunogens in the generation of antibodies that immunospecifically-bind these protein components. Such antibodies include, but are not limited to, polyclonal, monoclonal, chimeric, single chain, $F_{ab}$ fragments and an $F_{ab}$ expression library. In a specific embodiment, antibodies to a complex of human E6TP1 and human E6TP1-IP are disclosed. In another specific embodiment, complex formed from fragments of E6TP1 and E6TP1-IP; wherein these fragments contain the protein domain that interacts with the other member of the complex and are used as immunogens for antibody production. Various procedures known within the art may be used for the production of polyclonal or monoclonal antibodies to a E6TP1:E6TP1-IP complex, or derivative, fragment, analog or homolog thereof.

For the production of polyclonal antibodies, various host animals may be immunized by injection with the native E6TP1, E6TP1-IP, or an E6TP1:E6TP1-IP complex thereof, or a synthetic variant thereof, or a derivative of the foregoing (e.g., a cross-linked E6TP1:E6TP1-IP). Various adjuvants may be used to increase the immunological response and include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.) and human adjuvants such as *Bacille Calmette-Guerin* and *Corynebacterium parvum*.

For preparation of monoclonal antibodies directed towards a E6TP1, E6TP1-IP, or complex thereof, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975. *Nature* 256: 495–497); the trioma technique; the human B-cell hybridoma technique (see Kozbor, et al., 1983. *Immunol. Today* 4: 72) and the Epstein Barr Virus ("EBV") hybridoma technique to produce human monoclonal antibodies (see Cole, et al., 1985. In: Monoclonal Antibodies and Cancer Therapy, Alan R. Liss, Inc., pp. 77–96). Human monoclonal antibodies may be utilized in the practice of the present invention and may be produced by the use of human hybridomas (see Cote, et al., 1983. *Proc. Natl. Acad. Sci. USA* 80: 2026–2030) or by transforming human B-cells with EBV in vitro (see Cole, et al., 1985. In: Monoclonal Antibodies and Cancer Therapy, Alan R. Liss, Inc., pp. 77–96).

According to the invention, techniques can be adapted for the production of single-chain antibodies specific to E6TP1, E6TP1-IP, or complex thereof (see e.g., U.S. Pat. No. 4,946,778). In addition, methodologies can be adapted for the construction of $F_{ab}$ expression libraries (see e.g., Huse, et al., 1989. Science 246: 1275–1281) to allow rapid and effective identification of monoclonal $F_{ab}$ fragments with the desired specificity for E6TP1, E6TP1-IP, or complex thereof, or derivatives, fragments, analogs or homologs thereof. Non-human antibodies can be "humanized" by techniques well known in the art. See e.g., U.S. Pat. No. 5,225,539. Antibody fragments that contain the idiotypes to E6TP1, E6TP1-IP, or E6TP1:E6TP1-IP complex thereof, may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of E6TP1, E6TP1-IP, or complex thereof, is facilitated by generation of hybridomas that bind to the fragment of E6TP1, E6TP1-IP, or complex thereof, possessing such a domain. In another specific embodiment, methodologies for the selection of an antibody that specifically binds a E6TP1:E6TP1-IP complex but that does not specifically bind to the individual proteins of E6TP1:E6TP1-IP complex (identified by selecting the antibody on the basis of positive-binding to E6TP1:E6TP1-IP complex with a concomitant lack of binding to the individual E6TP1 and E6TP1-IP protein) are within the scope of the invention. Accordingly, antibodies that are specific for a domain within E6TP1, E6TP1-IP, or complex thereof, or derivative, fragments, analogs or homologs thereof, are also provided herein.

It should be noted that the aforementioned antibodies may be used in methods known within the art relating to the localization and/or quantitation of E6TP1, E6TP1-IP, or complex thereof (e.g., for use in measuring levels of the protein within appropriate physiological samples, for use in diagnostic methods, for use in imaging the protein, and the like). In a given embodiment, anti-E6TP1, anti-E6TP1-IP, and/or anti-E6TP1:E6TP1-IP complex antibodies, or derivatives, fragments, analogs or homologs thereof that contain the antibody derived binding domain, are utilized as pharmacologically-active compounds [hereinafter "Therapeutics"].

Use of E6TP1:E6TP1-IP Complex in Diagnosis, Prognosis and Screening

E6TP1, E6TP1-IP, or E6TP1:E6TP1-IP complex thereof, may serve as a "marker" for specific disease states that involve the disruption of physiological processes in which E6TP1 and E6TP1-IP are known to be involved. See, e.g., Background of the Invention. These physiological processes include, but are not limited to, (i) control of cell cycle progression, cellular differentiation and apoptosis, (ii) intracellular signal transduction, (iii) neurogenesis, (iv) response to viral infection; and (v) pathophysiological processes including, but not limited to, hyperproliferative disorders such as tumorigenesis and tumor spread; degenerative disorders such as neurodegenerative diseases, autoimmune diseases; disorders associated with organ transplantation, inflammatory and allergic diseases, atherosclerosis, nephropathy and cardiac muscle diseases; and the like. Thus E6TP1, E6TP1-IP, or E6TP1:E6TP1-IP complex thereof, are predicted to have diagnostic utility. As such, the differentiation and classification of particular groups of patients possessing elevations or deficiencies of a E6TP1, E6TP1-IP, or complex thereof, may lead to new nosological classifications of diseases, thereby markedly advancing diagnostic ability.

The detection of levels of E6TP1:E6TP1-IP complex or levels of E6TP1 and/or E6TP1-IP protein, or detection of levels of mRNAs that encode the components of a E6TP1:E6TP1-IP complex, may be utilized in the analysis of various diseases, and may provide critical information in various medical processes, including: diagnosis, prognosis, identifying disease states, following a disease course, following the efficacy of an administered therapeutics, following therapeutic response, and the like. Similarly, both the nucleic acid sequences (and sequences complementary thereto) and antibodies specific to E6TP1:E6TP1-IP complex and/or the individual components that can form E6TP1:E6TP1-IP complexes, can be used in diagnostics.

Said molecules may be utilized in assays (e.g., immunoassays) to detect, prognose, diagnose, or monitor various conditions, diseases, and disorders characterized by aberrant levels of E6TP1, E6TP1-IP, or complex thereof, or monitor the treatment thereof. An "aberrant level" means an increased or decreased level in a sample relative to that present in an analogous sample from an unaffected part of the body, or from a subject not having the disorder. The aforementioned immunoassay may be performed by a methodology comprising contacting a sample derived from a patient with an anti-E6TP1, anti-E6TP1-IP, and/or anti-E6TP1:E6TP1-IP complex antibody under conditions such that immunospecific-binding may occur, and subsequently detecting or measuring the amount of any immunospecific-binding by the antibody. In a specific embodiment, an antibody specific for E6TP1, E6TP1-IP, and/or a E6TP1:E6TP1-IP complex may be used to analyze a tissue or serum sample from a patient for the presence of uncomplexed or complexed E6TP1:E6TP1-IP; wherein an aberrant level of E6TP1, E6TP1-IP, and/or E6TP1:E6TP1-IP complex is indicative of a diseased condition. The immunoassays that may be utilized include, but are not limited to, competitive and non-competitive assay systems using techniques such as Western Blots, radioimmunoassays (RIA), enzyme linked immunosorbent assay (ELISA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein-A immunoassays, etc.

The nucleic acid species of the present invention encoding the associated protein components of E6TP1:E6TP1-IP complex, and related nucleotide sequences and subsequences, may also be used in hybridization assays. E6TP1 and E6TP1-IP nucleotide sequences, or subsequences thereof comprising at least 6 nucleotides, may be used as hybridization probes. Hybridization assays can be used to detect, prognose, diagnose, or monitor conditions, disorders, or disease states associated with aberrant levels of the mRNAs encoding the components of a E6TP1:E6TP1-IP complex, as described supra. In specific embodiments of the present invention, diseases and disorders involving or characterized by aberrant levels of E6TP1, E6TP1-IP, or complex thereof, or a predisposition to develop such disorders may be diagnosed by detecting aberrant levels of E6TP1:E6TP1-IP complex, or non-complexed E6TP1 and/or E6TP1-IP proteins or nucleic acids for functional activity. This aforementioned functional activity may include, but is not restricted to, (i) binding to an interacting partner (e.g., E6TP1, E6TP1-IP) or (ii) detecting mutations in E6TP1 and/or a E6TP1-IP RNA, DNA or protein (e.g., translocations, truncations, changes in nucleotide or amino acid sequence relative to wild-type E6TP1 and/or the E6TP1-IP) that can cause increased or decreased expression or activity of a E6TP1, a E6TP1-IP or a E6TP1:E6TP1-IP complex.

Methodologies that are well-known within the art (e.g., immunoassays, nucleic acid hybridization assays, biological activity assays, and the like) may be used to determine whether one or more particular E6TP1, E6TP1-IP, or complex thereof, are present at either increased or decreased levels, or are absent, within samples derived from patients suffering from a particular disease or disorder, or possessing a predisposition to develop such a disease or disorder, as compared to the levels in samples from subjects not having such disease or disorder or predisposition thereto. Additionally, these assays may be utilized to determine whether the ratio of E6TP1:E6TP1-IP complex to the non-complexed components (i.e. E6TP1 and/or E6TP1-IP) in the complex of interest is increased or decreased in samples from patients suffering from a particular disease or disorder or having a predisposition to develop such a disease or disorder as compared to the ratio in samples from subjects not having such a disease or disorder or predisposition thereto.

Accordingly, in specific embodiments of the present invention, diseases and disorders that involve increased/decreased levels of one or more E6TP1, E6TP1-IP, or complex thereof, may be diagnosed, or their suspected presence may be screened for, or a predisposition to develop such diseases and disorders may be detected, by quantitatively ascertaining increased/decreased levels of: (i) the one or more E6TP1, E6TP1-IP, or complex thereof; (ii) the mRNA encoding both protein members of said complex; (iii) the complex functional activity or (iv) mutations in E6TP1 or the E6TP1-IP (e.g., translocations in nucleic acids, truncations in the gene or protein, changes in nucleotide or amino acid sequence relative to wild-type E6TP1 or the E6TP1-IP) that enhance/inhibit or stabilize/destabilize E6TP1:E6TP1-IP complex formation.

In the practice of the present invention, the use of detection techniques, especially those involving antibodies directed against E6TP1, E6TP1-IP, or complex thereof, provide methods for the detection of specific cells that express the uncomplexed or complexed protein of interest, e.g., E6TP1 and/or E6TP1-IP. Using such assays, specific cell types may be quantitatively characterized in which one or more particular components of an E6TP1:E6TP1-IP complex are expressed, and the presence of the uncomplexed or complexed protein may be correlated with cell viability by techniques well-known within the art (e.g., fluorescence-activated cell sorting). Also embodied herein are methodologies directed to the detection of a E6TP1, E6TP1-IP, or complex thereof, within in vitro cell culture models that express a particular E6TP1, E6TP1-IP, or complex thereof, or derivatives thereof, for the purpose of characterizing and/or isolating E6TP1:E6TP1-IP complex. These detection techniques include, but are not limited to, cell-sorting of prokaryotes (see e.g., Davey & Kell, 1996. Microbiol. Rev. 60: 641–696); primary cultures and tissue specimens from eukaryotes, including mammalian species such as human (see e.g., Steele, et al., 1996. Clin. Obstet. Gynecol 39: 801–813) and continuous cell cultures (see e.g., Orfao & Ruiz-Arguelles, 1996. Clin. Biochem. 29: 5–9.

The present invention additionally provides kits for diagnostic use that are comprised of one or more containers containing an anti-E6TP1, anti-E6TP1-IP, and/or anti-E6TP1:E6TP1-IP complex antibody and, optionally, a labeled binding partner to said antibody. The label incorporated into the anti-E6TP1, anti-E6TP1-IP, and/or anti-E6TP1:E6TP1-IP complex antibody may include, but is not limited to, a chemiluminescent, enzymatic, fluorescent, colorimetric or radioactive moiety. In another specific embodiment, kits for diagnostic use that are comprised of one or more containers containing modified or unmodified nucleic acids that encode, or alternatively, that are the complement to, E6TP1, E6TP1-IP, and/or E6TP1:E6TP1-IP complex and, optionally, a labeled binding partner to said nucleic acids, are also provided. In an alternative specific embodiment, the kit may comprise, in one or more containers, a pair of oligonucleotide primers (e.g., each 6–30 nucleotides in length) that are capable of acting as amplification primers for polymerase chain reaction (PCR; see e.g., Innis, et al., 1990. PCR Protocols, Academic Press, Inc., San Diego, Calif.), ligase chain reaction, cyclic probe reaction, and the like, or other methods known within the art. The kit may, optionally, further comprise a predetermined amount of a purified E6TP1, E6TP1-IP or E6TP1:E6TP1-IP complex, or nucleic acids thereof, for use as a diagnostic, standard, or control in the aforementioned assays.

Therapeutic Uses of E6TP1 and E6TP1-IP Proteins and E6TP1:E6TP1-IP Complexes

The present invention provides a method for treatment or prevention of various diseases and disorders by administration of a biologically-active therapeutic compound (hereinafter "Therapeutic"). Such "Therapeutics" include but are not limited to: (i) E6TP1, E6TP1-IP, and E6TP1:E6TP1-IP complex, and derivative, fragments, analogs and homologs thereof; (ii) antibodies directed against the aforementioned proteins and protein complex thereof; (iii) nucleic acids encoding E6TP1 and/or E6TP1-IP, and derivatives, fragments, analogs and homologs thereof; (iv) antisense nucleic acids to sequences encoding E6TP1 and E6TP1-IP proteins, and (v) E6TP1:E6TP1-IP complex and modulators thereof ( i.e., inhibitors, agonists and antagonists).

Figure 3A:
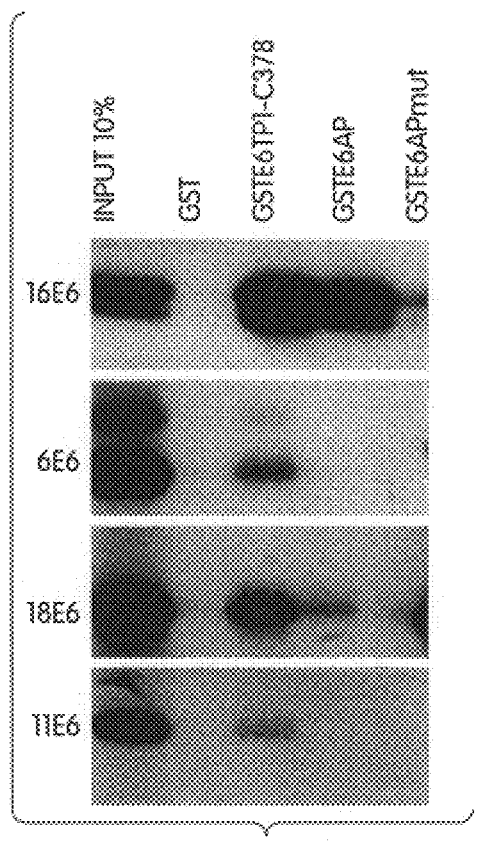
FIG. 3 illustrates in vitro binding of various low risk (HPV6 or -11) and high risk (HPV16 or -18) E6 proteins to: (Panel A) a GST-fused C-terminal 378 aa fragment of E6TP1 or various control GST-fused proteins; (Panel B) native full length E6TP1 protein and fragments thereof; and (Panel C) various GST fusion proteins incorporating different regions of E6TP1.
Figure 3C:
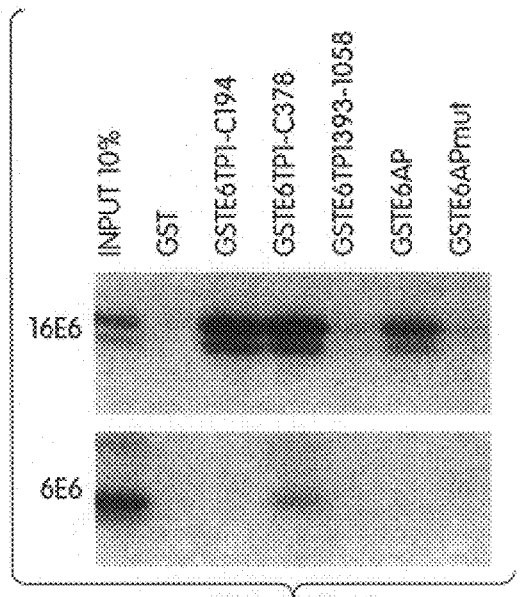
Figure 3B:
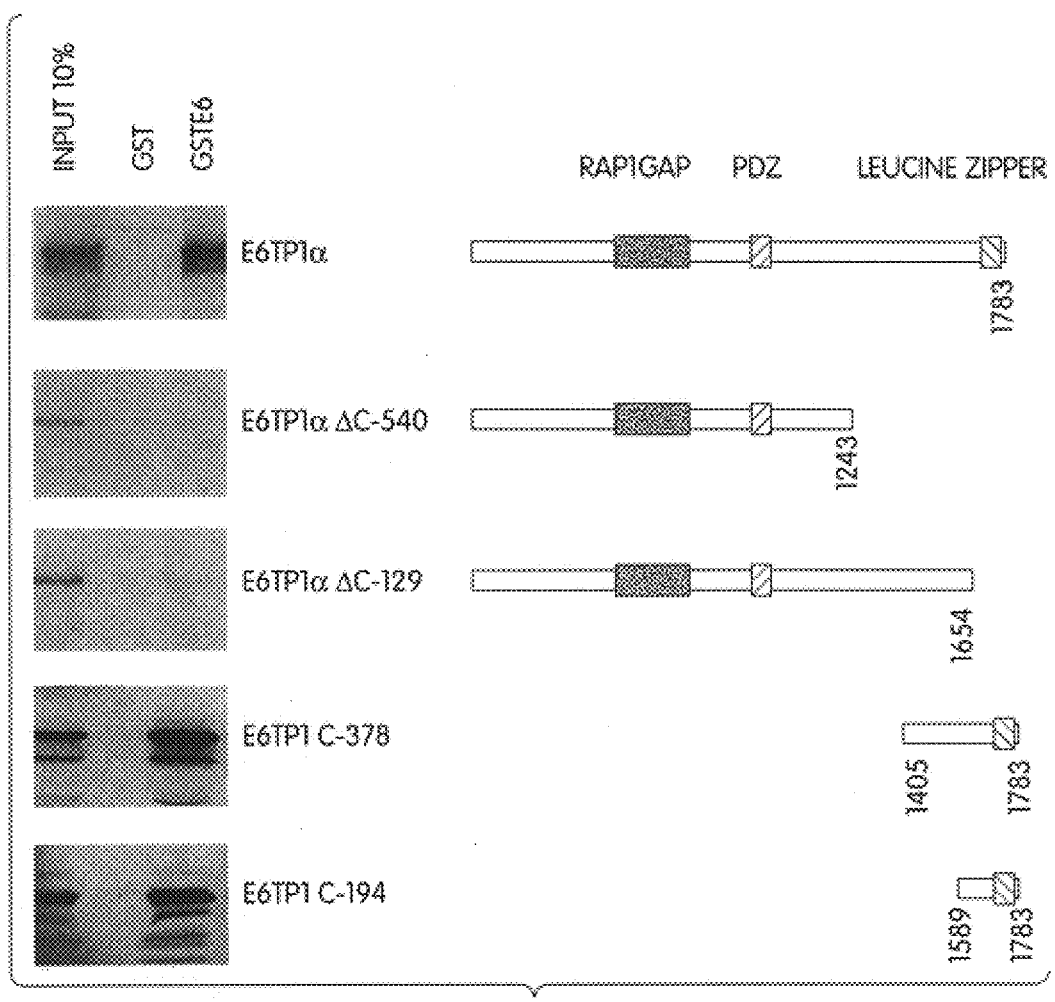

Distinct regions of E6TP1 are required for E6 binding and E6-dependent targeting to cellular degradation machinery. Binding of E6 to E6TP1 by itself is not sufficient for degradation, in that all four partial fragments of E6TP1 ($\Delta$C-540, $\Delta$C-129, C-194, C-378) were deficient in degradation even though E6TP1-C-194, and E6TP1-C-378 efficiently bind to E6 (as shown in FIG. 3B). Therefore, polypeptides or nucleic acids that encode polypeptides that contain said N-ter and C-ter regions of E6TP1 that are required for E6-targeted degradation, and derivatives, fragments, analogs and homologs thereof, are provided. In addition, E6TP1 polypeptide fragments lacking either the N-ter or the C-ter regions, or nucleic acids that encode said polypeptide fragments, which are therefore deficient in E6 targeted degradation, may be used as a Therapeutic of the invention in the prevention and treatment of diseases and disorders, including but not limited to HPV associated carcinomas and diseases. By means of illustration, but not of limitation, upon its use as a Therapeutic, said E6TP1 polypeptide fragments may bind E6, wherein said E6TP1 fragments would sequester E6 in an inactive complex. Said sequestration may thereby decrease the availability of E6 to target E6TP1 degradation, and may, in addition, decrease the ability of E6 to interact with other cellular component and/or inhibit E6-targeted degradation of other vital proteins.

As E6-induced degradation of p53 is mediated through E6-AP, a ubiquitin ligase (see, e.g., Background Section), E6-AP may turn out to be critical for E6-induced degradation of E6TP1. E6 can simultaneously bind E6TP1 and E6-AP, even though it is not required for E6:E6TP1 binding (in contrast E6:p53 binding requires E6-AP, see Background). Therefore, it is contemplated that administration of E6TP1 as a Therapeutic in HPV associated carcinomas and diseases would additionally sequester E6-AP in an inactive complex with E6TP1 and E6, further inhibiting E6-targeted degradation of p53.

E6TP1 is a likely tumor suppressor involved in cell growth and proliferation. Loss of the E6TP1 gene locus on chromosome 14q23.2–14q24.3 is associated with malignant meningiomas, supra. Therefore, E6TP1 may be administered as a Therapeutic in non-HPV-associated diseases, disorders, and carcinomas. In a specific embodiment of the invention, the carcinoma would be a meningioma. In a more specific embodiment of the invention, the carcinoma would be a malignant meningioma.

Therapeutics of the Invention

As discussed supra, E6TP1 and its binding partner E6TP1-IP, in which group HPV E6 and E6-AP proteins are included hereforth, are implicated significantly in disorders of cell cycle progression and cell differentiation, including cancer and tumorigenesis and tumor progression. Disorders of neurodegeneration resulting from altered cellular apoptosis, differentiation, and DNA repair likewise involves these same proteins. A wide range of cell diseases affected by physiological processes such as control of cell cycle progression, cellular differentiation and apoptosis, intracellular signal transduction, neurogenesis, response to viral infection; and pathophysiological processes including but not limited to hyperproliferative disorders such as tumorigenesis and tumor spread, degenerative disorders such as neurodegenerative diseases, disorders associated with organ transplantation, inflammatory and allergic diseases, autoimmune diseases, atherosclerosis, nephropathy, and cardiac and muscle diseases are treated or prevented by administration of a Therapeutic that modulates, i. e., antagonizes or promotes, E6TP1:E6TP1-IP complex activity or formation.

Diseases or disorders associated with aberrant levels of a E6TP1:E6TP1-IP complex or levels of activity or aberrant levels of E6TP1 may be treated by administration of a Therapeutic that modulates E6TP1:E6TP1-IP complex formation or activity. In a specific embodiment, the activity or levels of E6TP1 are modulated by administration of E6TP1-IP. In another specific embodiment, the activity or levels of E6TP1-IP are modulated by administration of E6TP1.

Disorders with Increased E6TP1 and E6TP1:E6TP1-IP Complex Levels

Diseases and disorders that are characterized by increased (relative to a subject not suffering from said disease or disorder) levels or biological activity of E6TP1, E6TP1-IP, or complex thereof, may be treated with Therapeutics that antagonize (i.e., reduce or inhibit) E6TP1 or E6TP1-IP activity, or E6TP1:E6TP1-IP complex formation or activity. Therapeutics that antagonize E6TP1 or E6TP1-IP activity, or E6TP1:E6TP1-IP complex formation or activity may be administered in a therapeutic or prophylactic manner. Therapeutics that may be utilized include, but are not limited to, E6TP1 or E6TP1-IP, or analogs, derivatives, fragments or homologs thereof; (ii) anti-E6TP1, anti-E6TP1-IP, and/or anti-E6TP1:E6TP1-IP complex antibodies; (iii) nucleic acids encoding E6TP1 or E6TP1-IP; (iv) concurrent administration of a E6TP1 and a E6TP1-IP antisense nucleic acid and E6TP1 and/or E6TP1-IP nucleic acids that are "dysfunctional" (i.e., due to a heterologous [non-E6TP1 and/or non-E6TP1-IP) insertion within the coding sequences of E6TP1 and E6TP1-IP coding sequences) are utilized to "knockout" endogenous E6TP1 and/or E6TP1-IP function by homologous recombination (see e.g., Capecchi, 1989. Science 244: 1288–1292). In an additionally embodiment of the present invention, mutants or derivatives of a first E6TP1-IP that possess greater affinity for E6TP1 than the wild-type first E6TP1-IP may be administered to compete with a second E6TP1-IP for binding to E6TP1, thereby reducing the levels of complex between E6TP1 and the second E6TP1-IP.

Increased levels of E6TP1 protein, E6TP1-IP protein, and/or E6TP1:E6TP1-IP complex can be readily detected by quantifying protein and/or RNA, by obtaining a patient tissue sample (e.g., from biopsy tissue) and assaying it in vitro for RNA or protein levels, structure and/or activity of the expressed E6TP1 protein, E6TP1-IP protein, and/or E6TP1:E6TP1-IP complex (or E6TP1 and E6TP1-IP mRNAs). Methods that are well-known within the art include, but are not limited to, immunoassays to detect E6TP1 protein, E6TP1-IP protein, and/or E6TP1:E6TP1-IP complex (e.g., by Western blot analysis, immunoprecipitation followed by sodium dodecyl sulfate (SDS) polyacrylamide gel electrophoresis, immunocytochemistry, etc.) and/or hybridization assays to detect concurrent expression of E6TP1 and E6TP1-IP mRNAs (e.g., Northern assays, dot blots, in situ hybridization, etc.).

Disorders with Reduced E6TP1 and E6TP1:E6TP1-IP Complex Expression

A specific embodiment of the present invention discloses methods for the reduction of E6TP1 protein, E6TP1-IP protein, and/or E6TP1:E6TP1-IP complex expression (i.e., the expression of the two protein components of the complex and/or formation of the complex) by targeting mRNAs that express the protein moieties. RNA Therapeutics are differentiated into three classes: (i) antisense species; (ii) ribozymes or (iii) RNA aptamers. See e.g., Good, et al., 1997. Gene Therapy 4: 45–54. Antisense oligonucleotides have been the most widely utilized and are discussed infra. Ribozyme therapy involves the administration (i.e., induced expression) of small RNA molecules with enzymatic ability to cleave, bind, or otherwise inactivate specific RNAs, thus reducing or eliminating the expression of particular proteins. See e.g., Grassi & Marini, 1996. Ann. Med. 28: 499–510. At present, the design of "hairpin" and/or "hammerhead" RNA ribozymes are necessary to specifically-target a particular mRNA (e.g., E6TP1 mRNA). RNA aptamers are specific RNA ligands for proteins, such as for Tat and Rev RNA, which can specifically inhibit their translation. See e.g., Good, et al., Gene Therapy 4: 45–54 (1997).

In a preferred embodiment of the present invention, the activity or level of E6TP1 may be reduced by administration of E6TP1-IP, a nucleic acid that encodes E6TP1-IP or an antibody (or a derivative or fragment of the antibody possessing the binding domain thereof) that immunospecifically-binds to E6TP1-IP. Similarly, the levels or activity of E6TP1-IP may be reduced by administration of E6TP1, a nucleic acid encoding E6TP1 or an antibody (or a derivative or fragment of the antibody possessing the binding domain thereof) that immunospecifically-binds E6TP1. In another embodiment of the present invention, diseases or disorders that are associated with increased levels of E6TP1 or E6TP1-IP, may be treated or prevented by administration of a Therapeutic that increases E6TP1:E6TP1-IP complex formation, if said complex formation acts to reduce or inactivate E6TP1 or the particular E6TP1-IP via E6TP1:E6TP1-IP complex formation. Such diseases or disorders may be treated or prevented by: (i) the administration of one member of E6TP1:E6TP1-IP complex, including mutants of one or both of the proteins that possess increased affinity for the other member of E6TP1:E6TP1-IP complex (so as to cause increased complex formation) or (ii) the administration of antibodies or other molecules that serve to stabilize E6TP1:E6TP1-IP complex, or the like.

Determination of the Biological Effect of the Therapeutic

In preferred embodiments of the present invention, suitable in vitro or in vivo assays are utilized to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon said cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Malignancies

Tumor suppressors, such as E6TP1, are involved in the regulation of cell proliferation. Accordingly, Therapeutics of the present invention, supra, may be useful in the therapeutic or prophylactic treatment of diseases or disorders that are associated with cell hyperproliferation and/or loss of control of cell proliferation (e.g., cancers, malignancies, and tumors). For a review of such hyperproliferation disorders, see e.g., Fishman, et al., 1985. Medicine, 2nd ed., J. B. Lippincott Co., Philadelphia, Pa.

Therapeutics of the present invention may be assayed by any method known within the art for efficacy in treating or preventing malignancies and related disorders. Such assays include, but are not limited to, in vitro assays utilizing transformed cells or cells derived from the patient's tumor, as well as in vivo assays using animal models of cancer or malignancies. Potentially effective Therapeutics are those that, for example, inhibit the proliferation of tumor-derived or transformed cells in culture or cause a regression of tumors in animal models, in comparison to the controls.

In the practice of the present invention, once a malignancy or cancer has been shown to be amenable to treatment by modulating (i.e., inhibiting, antagonizing or agonizing) E6TP1, E6TP1-IP, and/or E6TP1:E6TP1-IP complex activity, that cancer or malignancy may subsequently be treated or prevented by the administration of a Therapeutic that serves to modulate E6TP1:E6TP1-IP complex formation and function, including supplying E6TP1:E6TP1-IP complex and/or the individual binding partners of said protein complex (i.e., E6TP1 and/or E6TP1-IP). In a specific embodiment of the invention, said cancer or malignancy would be a malignant meningioma.

Premalignant Conditions

The Therapeutics of the present invention that are effective in the therapeutic or prophylactic treatment of cancer or malignancies may also be administered for the treatment of pre-malignant conditions and/or to prevent the progression of a pre-malignancy to a neoplastic or malignant state. Such prophylactic or therapeutic use is indicated in conditions known or suspected of preceding progression to neoplasia or cancer, in particular, where non-neoplastic cell growth consisting of hyperplasia, metaplasia or, most particularly, dysplasia has occurred. For a review of such abnormal cell growth see e.g., Robbins & Angell, 1976. Basic Pathology, 2nd ed., W.B. Saunders Co., Philadelphia, Pa.

Hyperplasia is a form of controlled cell proliferation involving an increase in cell number in a tissue or organ, without significant alteration in its structure or function. For example, it has been demonstrated that endometrial hyperplasia often precedes endometrial cancer. Metaplasia is a form of controlled cell growth in which one type of mature or fully differentiated cell substitutes for another type of mature cell. Metaplasia may occur in epithelial or connective tissue cells. Dysplasia is generally considered a precursor of cancer, and is found mainly in the epithelia. Dysplasia is the most disorderly form of non-neoplastic cell growth, and involves a loss in individual cell uniformity and in the architectural orientation of cells. Dysplasia characteristically occurs where there exists chronic irritation or inflammation, and is often found in the cervix, respiratory passages, oral cavity, and gall bladder.

Alternatively, or in addition to the presence of abnormal cell growth characterized as hyperplasia, metaplasia, or dysplasia, the presence of one or more characteristics of a transformed or malignant phenotype displayed either in vivo or in vitro within a cell sample derived from a patient, is indicative of the desirability of prophylactic/therapeutic administration of a Therapeutic that possesses the ability to modulate E6TP1, E6TP1-IP, and/or E6TP1:E6TP1-IP complex activity. Characteristics of a transformed phenotype include, but are not limited to: (i) morphological changes; (ii) looser substratum attachment; (iii) loss of cell-to-cell contact inhibition; (iv) loss of anchorage dependence; (v) protease release; (vi) increased sugar transport; (vii) decreased serum requirement; (viii) expression of fetal antigens, (ix) disappearance of the 250 kDal cell-surface protein, and the like. See e.g., Richards, et al., 1986. Molecular Pathology, W.B. Saunders Co., Philadelphia, Pa.

In a specific embodiment of the present invention, a patient that exhibits one or more of the following predisposing factors for malignancy is treated by administration of an effective amount of a Therapeutic: (i) a chromosomal translocation or rearrangement associated with a malignancy (e.g., the Philadelphia chromosome (bcr/abl) for chronic myelogenous leukemia and t(14; 18) for follicular lymphoma, deletion of 14q23.2–14q24.3 associated with malignant meningiomas, etc.); (ii) familial polyposis or Gardner's syndrome (possible forerunners of colon cancer); (iii) monoclonal gammopathy of undetermined significance (a possible precursor of multiple myeloma), (iv) a first degree kinship with persons having a cancer or pre-cancerous disease showing a Mendelian (genetic) inheritance pattern (e.g., familial polyposis of the colon, Gardner's syndrome, hereditary exostosis, polyendocrine adenomatosis, Peutz-Jeghers syndrome, neurofibromatosis of Von Recklinghausen, medullary thyroid carcinoma with amyloid production and pheochromocytoma, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia and Bloom's syndrome), and (v) infection with virus including, for example, the human papilloma virus (a predisposing factor for cervical carcinoma and anogenital neoplasms).

In another preferred embodiment, a Therapeutic of the present invention is administered to a human patient to prevent the progression to cervical, ovary, prostate, breast, colon, lung, pancreatic, kidney, esophagus, sebaceous gland, squamous cells, oral epithelium, keratinocyte or uterine cancer, or meningioma, melanoma, sarcoma, or carcinoma.

Hyperproliferative and Dysproliferative Disorders

In a preferred embodiment of the present invention, a Therapeutic is administered in the therapeutic or prophylactic treatment of hyperproliferative or benign dysproliferative disorders. The efficacy in treating or preventing hyperproliferative diseases or disorders of a Therapeutic of the present invention may be assayed by any method known within the art. Such assays include in vitro cell proliferation assays, in vitro or in vivo assays using animal models of hyperproliferative diseases or disorders, or the like. Potentially effective Therapeutics may, for example, promote cell proliferation in culture or cause growth or cell proliferation in animal models in comparison to controls.

In accord, once a hyperproliferative disorder has been shown to be amenable to treatment by modulation of E6TP1 protein, E6TP1-IP protein, or E6TP1:E6TP1-IP complex activity, the hyperproliferative disease or disorder may be treated or prevented by the administration of a Therapeutic that modulates E6TP1 or E6TP1-IP protein activity, or E6TP1:E6TP1-IP complex formation or activity (including supplying E6TP1:E6TP1-IP complex and/or the individual binding partners of a E6TP1:E6TP1-IP complex).

Specific embodiments of the present invention are directed to the treatment or prevention of cirrhosis of the liver (a condition in which scarring has overtaken normal liver regeneration processes); treatment of keloid (hypertrophic scar) formation causing disfiguring of the skin in which the scarring process interferes with normal renewal; psoriasis (a common skin condition characterized by excessive proliferation of the skin and delay in proper cell fate determination); benign tumors; fibrocystic conditions and tissue hypertrophy (e.g., benign prostatic hypertrophy).

Neurodegenerative Disorders

Tumor suppressors such as E6TP1, and possibly a binding partner E6TP1-IP, are implicated in the deregulation of cellular maturation and apoptosis, which are both characteristic of neurodegenerative disease. Accordingly, Therapeutics of the invention, particularly but not limited to those that modulate (or supply) E6TP1 protein, E6TP1-IP protein, E6TP1:E6TP1-IP complex activity may be effective in treating or preventing neurodegenerative disease. Therapeutics of the present invention that modulate E6TP1 protein, E6TP1-IP protein, E6TP1:E6TP1-IP complex activity involved in neurodegenerative disorders can be assayed by any method known in the art for efficacy in treating or preventing such neurodegenerative diseases and disorders. Such assays include in vitro assays for regulated cell maturation or inhibition of apoptosis or in vivo assays using animal models of neurodegenerative diseases or disorders, or any of the assays described infra. Potentially effective Therapeutics, for example but not by way of limitation, promote regulated cell maturation and prevent cell apoptosis in culture, or reduce neurodegeneration in animal models in comparison to controls.

Once a neurodegenerative disease or disorder has been shown to be amenable to treatment by modulation of E6TP1 protein, E6TP1-IP protein, E6TP1:E6TP1-IP complex activity, that neurodegenerative disease or disorder can be treated or prevented by administration of a Therapeutic that modulates E6TP1 or E6TP1-IP protein activity, and/or E6TP1:E6TP1-IP complex formation or activity, including supplying a E6TP1:E6TP1-IP complex or an uncomplexed binding partner, e.g., E6TP1 and/or E6TP1-IP. Such diseases include all degenerative disorders involved with aging, especially osteoarthritis and neurodegenerative disorders.

Gene Therapy

In a specific embodiment of the present invention, nucleic acids comprising a sequence that encodes E6TP1 and/or E6TP1-IP, or functional derivatives thereof, are administered to modulate E6TP1, E6TP1-IP, and/or E6TP1:E6TP1-IP complex function, by way of gene therapy. In more specific embodiments, a nucleic acid or nucleic acids encoding both E6TP1 and E6TP1-IP, or functional derivatives thereof, are administered by way of gene therapy. Gene therapy refers to therapy that is performed by the administration of a specific nucleic acid to a subject. In this embodiment of the present invention, the nucleic acid produces its encoded protein(s), which then serve to exert a therapeutic effect by modulating E6TP1, E6TP1-IP, and/or E6TP1:E6TP1-IP complex function. Any of the methodologies relating to gene therapy available within the art may be used in the practice of the present invention. See e.g., Goldspiel, et al., 1993. Clin. Pharm. 12: 488–505.

In a preferred embodiment, the Therapeutic comprises a E6TP1 and/or E6TP1-IP nucleic acid that is part of an expression vector expressing both of the aforementioned proteins, or fragments or chimeric proteins thereof, within a suitable host. In a specific embodiment, such a nucleic acid possesses a promoter that is operably-linked to E6TP1 and E6TP1-IP coding region(s), or, less preferably, two separate promoters linked to separate E6TP1 and E6TP1-IP coding regions. Said promoter may be inducible or constitutive, and, optionally, tissue-specific. In another specific embodiment, a nucleic acid molecule is used in which E6TP1 and E6TP1-IP coding sequences (and any other desired sequences) are flanked by regions that promote homologous recombination at a desired site within the genome, thus providing for intra-chromosomal expression of E6TP1 and E6TP1-IP nucleic acids. See e.g., Koller & Smithies, 1989. Proc. Natl. Acad. Sci. USA 86: 8932–8935.

Delivery of the Therapeutic nucleic acid into a patient may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, but not limited to, constructing said nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun®; Biolistic, DuPont); coating said nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see e.g., Wu & Wu, 1987. J Biol. Chem. 262: 4429–4432), which can be used to "target" cell types that specifically express the receptors of interest, etc.

In another specific embodiment of the present invention, a nucleic acid-ligand complex may be produced in which the ligand comprises a fusogenic viral peptide designed so as to disrupt endosomes, thus allowing the nucleic acid to avoid subsequent lysosomal degradation. In yet another specific embodiment, the nucleic acid may be targeted in vivo for cell-specific endocytosis and expression, by targeting a specific receptor. See e.g., PCT Publications WO 92/06180; WO 93/14188 and WO 93/20221. Alternatively, the nucleic acid may be introduced intracellularly and incorporated within a host cell genome for expression by homologous recombination. See e.g., Zijlstra, et al., 1989. *Nature* 342: 435–438.

In yet another specific embodiment, a viral vector that contains E6TP1 and/or E6TP1-IP nucleic acids is utilized. For example, retroviral vectors may be employed that have been modified to delete those retroviral-specific sequences that are not required for packaging of the viral genome, with its subsequent integration into host cell DNA. See e.g., Miller, et al., *Meth. Enzymol.* 217: 581–599 (1993). E6TP1 and/or E6TP1-IP (preferably both) nucleic acids may be cloned into a vector that facilitates delivery of the genes into a patient. See e.g., Boesen, et al., 1994. *Biotherapy* 6: 291–302; Kiem, et al., *Blood* 83: 1467–1473 (1994). Additionally, adenovirus may be used as an especially efficacious "vehicle" for the delivery of genes to the respiratory epithelia. Other targets for adenovirus-based delivery systems are liver, central nervous system, endothelial cells, and muscle. Adenoviruses also possess advantageous abilities to infect non-dividing cells. For a review see e.g., Kozarsky & Wilson, 1993. *Curr. Opin. Gen. Develop.* 3: 499–503. Adenovirus-associated virus (AAV) has also been proposed for use in gene therapy. See e.g., Walsh, et al., 1993. *Proc. Soc. Exp. Biol. Med* 204: 289–300.

An additional approach to gene therapy in the practice of the present invention involves transferring a gene into cells in in vitro tissue culture by such methods as electroporation, lipofection, calcium phosphate-mediated transfection, viral infection, or the like. Generally, the methodology of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including, but not limited to: transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. *Meth. Enzymol.* 217: 599–618. The chosen technique should provide for the stable transfer of the nucleic acid to the cell, such that the nucleic acid is expressible by the cell. Preferably, said transferred nucleic acid is heritable and expressible by the cell progeny.

In preferred embodiments of the present invention, the resulting recombinant cells may be delivered to a patient by various methods known within the art including, but not limited to, injection of epithelial cells (e.g., subcutaneously), application of recombinant skin cells as a skin graft onto the patient, and intravenous injection of recombinant blood cells (e.g., hematopoietic stem or progenitor cells). The total amount of cells that are envisioned for use depend upon the desired effect, patient state, and the like, and may be determined by one skilled within the art.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, *Cell* 71: 973–985), hematopoietic stem or progenitor cells, e.g., as obtained from bone marrow, umbilical cord blood, peripheral blood, fetal liver, and the like. In a preferred embodiment, the cells utilized for gene therapy are autologous to the patient.

In a specific embodiment in which recombinant cells are used in gene therapy, stem or progenitor cells that can be isolated and maintained in vitro may be utilized. Such stem cells include, but are not limited to, hematopoietic stem cells (HSC), stem cells of epithelial tissues, and neural stem cells (see e.g., Stemple & Anderson, 1992. *Cell* 71: 973–985). With respect to HSCs, any technique that provides for the isolation, propagation, and maintenance in vitro of HSC may be used in this specific embodiment of the invention. As previously discussed, the HSCs utilized for gene therapy may, preferably, be autologous to the patient. When used, non-autologous HSCs are, preferably, utilized in conjunction with a method of suppressing transplantation immune reactions of the future host/patient. See e.g., Kodo, et al., 1984. *J Clin. Invest.* 73: 1377–1384. In another preferred embodiment of the present invention, HSCs may be highly enriched (or produced in a substantially-pure form), by any techniques known within the art, prior to administration to the patient. See e.g., Witlock & Witte, 1982. *Proc. Natl Acad. Sci. USA* 79: 3608–3612.

Utilization of Anti-sense Oligonucleotides

In a specific embodiment of the present invention, E6TP1, E6TP1-IP, and/or E6TP1:E6TP1-IP complex formation and function may be inhibited by the use of anti-sense nucleic acids for E6TP1 or E6TP1-IP, or most preferably, E6TP1 and E6TP1-IP. In addition, the present invention discloses the therapeutic or prophylactic use of nucleic acids (of at least six nucleotides in length) that are anti-sense to a genomic sequence (gene) or cDNA encoding E6TP1 and/or E6TP1-IP, or portions thereof. Such anti-sense nucleic acids have utility as Therapeutics that inhibit E6TP1 and/or E6TP1-IP activity, and/or E6TP1:E6TP1-IP complex formation or activity, and may be utilized in a therapeutic or prophylactic manner.

Another specific embodiment of the present invention discloses methodologies for inhibition of expression of E6TP1 and E6TP1-IP nucleic acid sequences within a prokaryotic or eukaryotic cell, such as providing a cell with an therapeutically-effective amount of an anti-sense nucleic acid of E6TP1 and/or E6TP1-IP, or derivatives thereof.

The anti-sense nucleic acids of the present invention may be oligonucleotides that may either be directly administered to a cell or that may be produced in vivo by transcription of the exogenous, introduced sequences. In addition, the anti-sense nucleic acid may be complementary to either a coding (i.e., exonic) and/or non-coding (i.e., intronic) region of E6TP1 or E6TP1-IP mRNAs. E6TP1 and E6TP1-IP anti-sense nucleic acids are, at least, six nucleotides in length and are, preferably, oligonucleotides ranging from 6–200 nucleotides in length. In specific embodiments, the anti-sense oligonucleotide is at least 10 nucleotides, at least 15, 35, 50, 100, or 200 nucleotides. The anti-sense oligonucleotides may be DNA or RNA (or chimeric mixtures, derivatives or modified versions thereof), may be either single-stranded or double-stranded and may be modified at a base, sugar or phosphate backbone moiety.

In addition, said anti-sense oligonucleotide may include other associated functional groups, such as peptides, moieties that facilitate the transport of the oligonucleotide across the cell membrane, hybridization-triggered cross-linking agents, hybridization-triggered cleavage-agents, and the like. See e.g., Letsinger, et al., 1989. *Proc. Natl. Acad. Sci. U.S.A.* 86: 6553–6556; PCT Publication No. WO 88/09810. In a specific embodiment, E6TP1 and E6TP1-IP antisense oligonucleotides comprise catalytic RNAs or ribozymes. See, e.g., Sarver, et al., 1990. *Science* 247: 1222–1225.

The anti-sense oligonucleotides of the present invention may be synthesized by standard methodologies known within the art including, but not limited to: (i) automated phosphorothioate-mediated oligonucleotide synthesis (see e.g., Stein, et al., 1988. *Nuc. Acids Res.* 16: 3209) or (ii) methylphosphonate oligonucleotides prepared by use of controlled pore glass polymer supports (see e.g., Sarin, et al., 1988. *Proc. Natl. Acad. Sci. U.S.A.* 85: 7448–7451).

In an alternative embodiment, E6TP1 and E6TP1-IP antisense nucleic acids are produced intracellularly by transcription of an exogenous sequence. For example, a vector comprising a promoter functionally linked to the reverse complement of a desired gene, and the like, may be produced that (upon being taken up by the cell) is transcribed in vivo, thus producing an antisense nucleic acid (RNA) species. The aforementioned vector may either remain episomal or become chromosomally-integrated, so long as it can be transcribed to produce the desired antisense RNA. An origin of the vectors utilized may be derived from bacterial, viral, yeast or other sources known within the art that are utilized for replication and expression in mammalian cells. Expression of the sequences encoding E6TP1 and E6TP1-IP antisense RNAs may be facilitated by any promoter known within the art to function in mammalian, preferably, human cells. Such promoters may be inducible or constitutive and include, but are not limited to: (i) the SV40 early promoter region; (ii) the promoter contained in the 3'-terminus long terminal repeat of Rous sarcoma virus (RSV); (iii) the Herpesvirus thymidine kinase promoter and (iv) the regulatory sequences of the metallothionein gene.

E6TP1 and E6TP1-IP antisense nucleic acids may be utilized prophylactically or therapeutically in the treatment or prevention of disorders of a cell type that expresses (or preferably over-expresses) E6TP1, E6TP1-IP, and/or E6TP1:E6TP1-IP complex. Cell types that express or over-express E6TP1 and E6TP1-IP RNA may be identified by various methods known within the art including, but not limited to, hybridization with E6TP1 and E6TP1-IP-specific nucleic acids (e.g., by Northern hybridization, dot blot hybridization, in situ hybridization) or by observing the ability of RNA from the specific cell type to be translated in vitro into E6TP1 and/or E6TP1-IP by immunohistochemistry. In a preferred aspect, primary tissue from a patient may be assayed for E6TP1 and/or E6TP1-IP expression by, for example, immunocytochemistry or in situ hybridization, prior to actual treatment.

Pharmaceutical compositions of the present invention, comprising an effective amount of a E6TP1 and E6TP1-IP antisense nucleic acid contained within a pharmaceutically-acceptable carrier, may be administered to a patient having a disease or disorder of a type that involves modified expression of E6TP1:E6TP1-IP complex, or of RNA or protein of the individual components of said complex. The amount of E6TP1 and/or E6TP1-IP antisense nucleic acid that is effective in the treatment of a particular disorder or condition will be dependant upon the nature of the disorder or condition, and may be determined by standard clinical techniques. Where possible, it is desirable to determine the antisense cytotoxicity in in vitro systems and in useful animal model prior to testing and use in humans. In a specific embodiment, pharmaceutical compositions comprising E6TP1 and E6TP1-IP antisense nucleic acids may be administered via liposomes, microparticles, or microcapsules or the like. See, e.g., supra, and Leonetti, et al., 1990. *Proc. Natl. Acad Sci. USA.* 87: 2448–2451.

E6TP1, E6TP1-IP, and E6TP1:E6TP1-IP Complex Assays

The functional activity of E6TP1, E6TP1-IP, and E6TP1:E6TP1-IP complex (and derivatives, fragments, analogs and homologs thereof) may be assayed by a number of methods known in the art. For example, putative modulators (e.g., inhibitors, agonists and antagonists) of E6TP1, E6TP1-IP, and E6TP1:E6TP1 complex activity (e.g., anti-E6TP1, anti-E6TP1-IP, and anti-E6TP1:E6TP1-IP complex antibodies, as well as E6TP1 or E6TP1-IP antisense nucleic acids) may be assayed for their ability to modulate E6TP1, E6TP1-IP, and E6TP1:E6TP1-IP complex formation and/or activity.

Immunoassays

In a specific embodiment, immunoassay-based methodologies are provided wherein one is assaying for: (i) the ability to bind to, or compete with, wild-type E6TP1:E6TP1-IP complex or E6TP1 or E6TP1-IP, or (ii) the ability to bind to an anti-E6TP1, anti-E6TP1-IP, or anti-E6TP1:E6TP1-IP complex antibody. These immunoassays include, but are not limited to, competitive and non-competitive assay systems utilizing techniques such as radioimmunoassays, enzyme linked immunosorbent assay (ELISA), "sandwich" immunoassays, immunoradiometric assays, gel diffusion precipitin reactions, immunodiffusion assays, in situ immunoassays (e.g., using colloidal gold, enzyme or radioisotope labels), complement fixation assays, Western blots, Northwestern blots, precipitation reactions, agglutination assays (e.g., gel agglutination assays, hemagglutination assays), immunofluorescence assays, protein-A assays and immunoelectrophoresis assays, and the like. In one specific embodiment, antibody binding is detected directly by assaying for a label on a primary antibody. In another specific embodiment, binding of the primary antibody is ascertained by detection of a secondary antibody (or reagent) that is specific for the primary antibody. In a further embodiment, the secondary antibody is labeled.

Gene Expression Assays

Expression of E6TP1 or E6TP1-IP genes (from both endogenous genes and from incorporated recombinant DNA) may be detected using techniques known within the art including, but not limited to, Southern hybridization, Northern hybridization, restriction endonuclease mapping, DNA sequence analysis, and polymerase chain reaction amplification (PCR) followed by Southern hybridization or RNase protection (see e.g., Current Protocols In Molecular Biology 1997, John Wiley and Sons, New York, N.Y.) with probes specific for E6TP1 and E6TP1-IP genes in various cell types.

In one specific embodiment of the present invention, Southern hybridization may be used to detect genetic linkage of E6TP1 and/or E6TP1-IP gene mutations to physiological or pathological states. Numerous cell types, at various stages of development, may be characterized for their expression of E6TP1 and E6TP1-IP (particularly the concomitant expression of E6TP1 and E6TP1-IP within the same cells). The stringency of the hybridization conditions for Northern or Southern blot analysis may be manipulated to ensure detection of nucleic acids with the desired degree of relatedness to the specific probes used. See, e.g., supra.

Modification of these aforementioned methods, as well as other methods well-known within the art, may be utilized in the practice of the present invention.

Binding Assays

Derivatives, fragments, analogs and homologs of E6TP1-IP may be assayed for binding to E6TP1 by any method known within the art including, but not limited to: (i) the modified yeast two hybrid assay system; (ii) immunoprecipitation with an antibody that binds to E6TP1 within a complex, followed by analysis by size fractionation of the immunoprecipitated proteins (e.g., by denaturing or non-denaturing polyacrylamide gel electrophoresis); (iii) Western analysis; (v) non-denaturing gel electrophoresis, and the like. Alternatively, the aforementioned techniques may be modified to allow for the reverse analysis, whereby E6TP1 components bind to E6TP1-IP.

Assays for Biological Activity

A specific embodiment of the present invention provides a methodology for screening a derivative, fragment, analog or homolog of E6TP1 for biological activity, which is comprised of contacting said derivative, fragment, analog or homolog of E6TP1 with E6TP1-IP and detecting complex formation between said derivative, fragment, analog or homolog of E6TP1 and E6TP1-IP; wherein the detection of the formation of said complex indicates that said E6TP1 derivative, fragment, analog or homolog, possesses biological (e.g., binding) activity. Similarly, an additional embodiment discloses a methodology for the screening a derivative, fragment, analog or homolog of E6TP1-IP for biological activity comprising contacting said derivative, fragment, analog or homolog of said protein with E6TP1; and detecting complex formation between said derivative, fragment, analog or homolog of E6TP1-IP and E6TP1; wherein detecting the formation of said complex indicates that said E6TP1-IP derivative, fragment, analog, or homolog possesses biological activity.

Modulation of E6TP1:E6TP1-IP Complex Activity

The present invention provides methodologies relating to modulating the level or activity of a protein moiety that possesses the ability to participate in a E6TP1:E6TP1-IP complex, via the administration of a binding partner of that protein (or derivative, fragment, analog or homolog thereof). E6TP1 (and derivatives, fragments, analogs and homologs thereof) may be assayed for its ability to modulate the activity or levels of E6TP1-IP by contacting a cell, or administering to an animal expressing the E6TP1-IP gene, with E6TP1 protein, or, alternatively, with a nucleic acid encoding E6TP1 or an antibody that immunospecifically-binds E6TP1, or derivative, fragment, analog, or homolog thereof that contains the antibody binding domain, and measuring a change in E6TP1-IP levels or activity, wherein said change in E6TP1-IP levels or activity indicates that said E6TP1 possesses the ability to modulate E6TP1-IP levels or activity. In another embodiment, E6TP1-IP (and derivatives, fragments, analogs and homologs thereof) may be assayed for their ability to modulate the activity or levels of E6TP1 in an analogous manner.

E6TP1-Related Treatment Assays

Tumorigenesis

Tumor suppressors such as E6TP1 plays a role in the control of cell proliferation and, therefore, of cell-transformation and tumorigenesis. The present invention discloses methodologies for screening E6TP1, E6TP1-IP, and E6TP1:E6TP1-IP complex (and derivatives, fragments, analogs and homologs, thereof) for the ability to alter cell proliferation, cell transformation and/or tumorigenesis in vitro and in vivo. For example, but not by way of limitation, cell proliferation may be assayed by measuring $^3$H-thymidine incorporation, by direct cell count, by detecting changes in transcriptional activity of known genes such as proto-oncogenes (e.g, c-fos, c-myc) cell-cycle markers, and the like.

E6TP1, E6TP1-IP, and/or E6TP1:E6TP1-IP complex (and derivatives, fragments, analogs and homologs, thereof) may also be screened for activity in inducing or inhibiting cell transformation (or the progression to malignant phenotype) in vitro. The proteins and protein complexes of the present invention may be screened by contacting either cells with a normal phenotype (for assaying for cell transformation) or cells with a transformed phenotype (for assaying for inhibition of cell transformation) with the uncomplexed or complexed proteins of the present invention and examining said cells for acquisition or loss of characteristics associated with a transformed phenotype (e.g., a set of in vitro characteristics associated with a tumorigenic ability in vivo) including, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250 kDal cell-surface protein, and the like. See e.g., Luria, et al., 1978. General Virology, 3rd ed. (Wiley & Sons, New York, N.Y.).

E6TP1, E6TP1-IP, and/or E6TP1:E6TP1-IP complex (and derivatives, fragments, analogs and homologs, thereof) may also be screened for activity to promote or inhibit tumor formation in vivo in non-human test animal. A vast number of animal models of hyperproliferative disorders (e.g., tumorigenesis and metastatic spread) are known within the art. See e.g., Lovejoy, et al., 1997. *J. Pathol.* 181: 130–135. In a specific embodiment of the present invention, the uncomplexed or complexed proteins of the present invention may be administered to a non-human test animal (preferably a test animal predisposed to develop a type of tumor), wherein the non-human test animal is subsequently examined for increased incidence of tumor formation in comparison with controls animals that were not administered the individual proteins or the protein complex of the present invention. Alternatively, the individual proteins and/or the protein complex may be administered to non-human test animals possessing tumors (e.g., animals in which tumors have been induced by introduction of malignant, neoplastic, or trans-formed cells or by administration of a carcinogen) and subsequently examining the tumors within the test animals for tumor regression in comparison to controls. Accordingly, once a hyperproliferative disease or disorder has been shown to be amenable to treatment by modulation of E6TP1, E6TP1-IP, and/or E6TP1:E6TP1-IP complex activity, that disease or disorder may be treated or prevented by administration of a Therapeutic that modulates E6TP1, E6TP1-IP, and/or formation of complexes thereof Neurodegeneration Similarly, once a neurodegeneration disease or disorder has been shown to be amenable to treatment by modulation of E6TP1, E6TP1-IP, and/or E6TP1 :E6TP1-IP complex activity or formation, that disease or disorder can be treated or prevented by administration of a Therapeutic that modulates E6TP1, E6TP1-IP, and/or E6TP1:E6TP1-IP complex activity or formation, including supplying E6TP1, E6TP1-IP, and/or E6TP1 :E6TP1-IP complex. In a specific embodiment, E6TP1, E6TP1-IP, and/or E6TP1:E6TP1-IP complex is administered to treat or prevent a neurodegenerative disease, disorder, or malignancy. E6TP1 has been implicated malignant meningiomas. See, e.g., Menon et al., *Oncogene* 14: 611–616 (1997); Simon et al., *Cancer Res* 55: 4696–4701 (1995); Tse et al., *Hum Pathol* 28: 779–785 (1997). Accordingly, an E6TP1 protein, E6TP1-IP protein, and/or E6TP1:E6TP1-IP complex, or derivative, homolog, analog or fragment thereof; a nucleic acid molecule encoding E6TP1 or E6TP1-IP; an anti-E6TP1, anti-E6TP1-IP, and/or anti-E6TP1:E6TP1-IP complex antibodies; and other modulators of E6TP1, E6TP1-IP, and/or E6TP1:E6TP1-IP complex activity or formation can be tested for activity in treating or preventing neurodegenerative disease or malignant meningiomas in in vitro and in vivo assays.

In one embodiment, a Therapeutic of the invention can be assayed for activity in treating or preventing neurodegenerative disease by contacting a cultured cell that exhibits an indicator of a neurodegenerative disease in vitro with the Therapeutic and comparing the level of said indicator in the cell so contacted with the Therapeutic, with said level of said indicator in a cell not so contacted, wherein a lower level in said contacted cell indicates that the Therapeutic has activity in treating or preventing neurodegenerative disease. Specific examples of such cultured models for neurodegenerative disease include, but are not limited to, cultured rat endothelial cells from affected and nonaffected individuals (Maneiro el al., 1997, Methods Find. Exp. Clin. Pharmacol. 19: 5–12); P19 murine embryonal carcinoma cells (Hung et al., 1992, Proc. Natl. Acad. Sci. USA 89: 9439–9443); and dissociated cell cultures of cholinergic neurons from nucleus basalis of Meynert (Nakajima et al., 1985, Proc. Natl. Acad. Sci. USA 82: 6325–6329).

In another embodiment, a Therapeutic of the invention can be assayed for activity in treating or preventing neurodegenerative disease by administering the Therapeutic to a test animal that is predisposed to develop symptoms of a neurodegenerative disease, and measuring the change in said symptoms after administration of said Therapeutic, wherein a reduction in the severity of the symptoms of the neurodegenerative disease, or the prevention of the symptoms of the neurodegenerative disease, indicates that the Therapeutic has activity in treating or preventing said disease states. Such a test animal can be any one of a number of animal models known in the art for neurodegenerative disease. These models, including those for Alzheimer's Disease and mental retardation of trisomy 21, accurately mimic natural human neurodegenerative diseases. Farine, 1997, *Toxicol* 119: 29–35. Examples of specific models include, but are not limited to, the partial trisomy 16 mouse (Holtzman et al., 1996, *Proc. Natl Acad Sci USA* 93: 13333–13338); bilateral nucleus basalis magnocellularis-lesioned rats (Popovic et al., 1996, *Int J Neurosci* 86: 281–299); the aged rat (Muir, 1997, *Pharmacol Biochem Behav* 56: 687–696); the PDAPP transgenic mouse model of Alzheimer's disease (Johnson-Wood et al., 1997, *Proc Natl Acad Sci USA* 94: 1550–1555); and experimental autoimmune dementia (Oron et al., 1997, *J Neural Transm Suppl* 49: 77–84).

Pharmaceutical Compositions

The invention provides methods of treatment and prophylaxis by the administration to a subject of an pharmaceutically-effective amount of a Therapeutic of the invention. In a preferred embodiment, the Therapeutic is substantially purified and the subject is a mammal, and most preferably, human.

Formulations and methods of administration that can be employed when the Therapeutic comprises a nucleic acid are described supra. Various delivery systems are known and can be used to administer a Therapeutic of the present invention including, but not limited to: (i) encapsulation in liposomes, microparticles, microcapsules; (ii) recombinant cells capable of expressing the Therapeutic; (iii) receptor-mediated endocytosis (see, e.g., Wu & Wu, 1987. *J. Biol. Chem.* 262: 4429–4432); (iv) construction of a Therapeutic nucleic acid as part of a retroviral or other vector, and the like.

Methods of administration include, but are not limited to, intradermal, intramuscular, intraperitoneal, intravenous, subcutaneous, intranasal, epidural, and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment. This may be achieved by, for example, and not by way of limitation, by local infusion during surgery, by topical application, by injection, by means of a catheter, by means of a suppository, or by means of an implant. In a specific embodiment, administration may be by direct injection at the site (or former site) of a malignant tumor or neoplastic or pre-neoplastic tissue.

In another embodiment of the present invention, the Therapeutic may be delivered in a vesicle, in particular a liposome. See e.g., Langer, 1990. *Science* 249: 1527–1533. In yet another embodiment, the Therapeutic can be delivered in a controlled release system including, but not limited to, a delivery pump (see e.g., Saudek, et al., 1989. *New Engl. J. Med* 321: 574) and a semi-permeable polymeric material (see e.g., Howard, et al., 1989. *J. Neurosurg.* 71: 105). Additionally, the controlled release system can be placed in proximity of the therapeutic target (e.g., the brain), thus requiring only a fraction of the systemic dose. See, e.g., Goodson, In: Medical Applications of Controlled Release, CRC Press, Bocca Raton, Fla. (1984).

In a specific embodiment, where the Therapeutic is a nucleic acid encoding a protein, the Therapeutic nucleic acid may be administered in vivo to promote expression of its encoded protein by constructing it as part of an appropriate nucleic acid expression vector and administering it so that it becomes intracellular (e.g., via a retroviral vector, direct injection, use of microparticle bombardment, coating with lipids or cell-surface receptors or transfecting agents, or administering it in linkage to a homeobox-like peptide that is known to enter the nucleus (see e.g., Joliot, et al., 1991. *Proc. Natl. Acad Sci. USA* 88: 1864–1868), and the like. Alternatively, a nucleic acid Therapeutic can be introduced intracellularly and incorporated into host cell DNA for expression, e.g., by homologous recombination.

The present invention also provides pharmaceutical compositions. Such compositions comprise a therapeutically-effective amount of Therapeutic, and a pharmaceutically acceptable carrier. As utilized herein, the term "pharmaceutically acceptable" means approved by a regulatory agency of the Federal or a state government, or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited, to such sterile liquids as water and oils. The amount of the Therapeutic of the invention that will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration and the overall seriousness of the disease or disorder, and should be decided according to the judgment of the practitioner and of each patient's circumstances. However, suitable dosage ranges for intravenous administration of a Therapeutics herein are generally about 20–500 micrograms (μg) of active compound per kilogram (kg) body weight. Suitable dosage ranges for intranasal administration are generally about 0.01 picograms (pg)/kg body weight to 1 milligram (mg)/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

The present invention also provides a pharmaceutical pack or kit, comprising one or more containers filled with one or more of the ingredients of the pharmaceutical compositions and Therapeutics of the present invention. Optionally associated with such container(s) may be a notice in the form prescribed by a governmental agency regulating the manufacture, use, or sale of pharmaceutical or biological products, which notice reflects approval by the agency of manufacture, use, or sale for human administration.

EXAMPLES

Example 1

Identification of HPV16 E6 Interacting Protein Using the Yeast Two-hybrid System Yeast two-hybrid constructs and screening To identify novel HPV E6targets, HPV16 E6 open reading frame was cloned in the bait vector pGBT9 and used to screen for interacting proteins encoded by normal mammary epithelial cell (strain 76N) cDNAs cloned in the yeast two-hybrid vector pGAD10 (custom-made through Clontech, CA). See, e.g., Chien et al., *Proc Natl Acad Sci USA* 88: 9578–9582 (1991). Briefly, mRNA purified from normal MEC strain 76N was used to synthesize cDNA in the presence of a mixture of oligo(dT) and random hexanucleotide primers. The cDNA was cloned into the EcoRI site of pGAD10, and a library of $1.5 \times 10^6$ primary recombinants with an average insert size of 1.5 kb was obtained. The bait plasmid pGBT9-E6 was constructed by cloning the PCR-derived HPV16 E6 residues 2–158 as a SalI-SmaI fragment into pGBT9. The two-hybrid library screen was performed according to the Matchmaker two-hybrid system protocol (Clontech, CA.) to identify E6-interacting proteins. The *Saccharomyces cerevisiae* yeast strain CG-1945 (five transformations) or HF7c (one transformation) were simultaneously transformed with pGBT9-E6 and the pGAD10 library DNA. HPV16 E6 interacting proteins were identified by growth on Trp⁻, Leu⁻, and His⁻ selection medium and positive β-gal activity.

Out of a total of $3.96 \times 10^6$ transformant clones screened in 6 transformations, 221 colonies grew on selection medium and 91 of these were positive in a subsequent β-gal assay. To identify E6-interacting proteins among these 91 clones, an interaction assay was performed with pGB9-E6 versus two control baits that included human lamin or murine p53 fused to Gal4 in pGBT9. Twenty-eight clones were found to interact with HPV16 E6 specifically, and were subsequently sequenced. Of these twenty-eight clones, one weakly positive clone encoded the 476 carboxyl-terminal amino acids of E6-AP, a known E6-binding protein, including its 18 aa E6-binding motif. See, e.g., Huibregtse et al., *Mol Cell Biol* 13. 4918–4927 (1993). This result confirmed that the cDNA library and the method of screening were suitable for isolating E6-binding proteins. Interestingly, a set of eleven identical and one distinct strongly positive clones that identified a single overlapping region (the 194 and 378 carboxyl terminal amino acid residues, respectively) of a single cDNA of a novel polypeptide were obtained. We have designated this novel protein E6TP1 ("E6-targeted protein1"). In addition, the remaining 15 clones encoded 1 known and 4 novel proteins.

Clones that remained positive in both assays were retested for E6-specific interaction by assessing their interaction with pGB9-E6 versus two control baits, pLam 5' (which encodes a human lamin/GAL4 DNA binding domain fusion protein in pGBT9) and pVA3 (which encodes a murine p53/GAL4 DNA binding domain fusion protein in pGBT9) (Clontech, CA.).

Molecular Cloning and Sequencing of Full-length E6TP1, and Plasmid Constructs

In order to obtain a full-length cDNA for E6TP1, we utilized a combination of DNA-hybridization screening of the 76N pGAD10 library and Marathon PCR cloning from normal mammary gland cDNA. See, e.g., supra. A 5965 bp cDNA predicting a 1783 aa polypeptide (E6TP1α) was obtained using these strategies [SEQ ID NOS:1 and 2]. The size of this cDNA and the presence of several in-frame stop codons 5' to the initiation methionine indicate that this cDNA represents the major 6.0 kb transcript expressed in 76N MEC cell strain (FIG. 2A). One cDNA library-derived clone revealed a 63 bp in-frame insertion after nucleotide 3993, predicting a 1804 aa polypeptide (E6TP1β, FIG. 2B) [SEQ ID NOS:3 and 4].

The 1403 bp E6TP1 DNA fragment isolated through two-hybrid screen was $^{32}$P-labeled and used as a probe for colony hybridization of the pGAD10 library. Two longer clones (2419 and 2262 bp, respectively) obtained through this approach were sequenced. Based on this sequence, two rounds of Marathon PCR (Clontech, CA.) were performed using normal mammary gland cDNA as templates to clone the additional 5' sequences (first round Marathon PCR primers: 5'-ccggcggccg cGAAAGCTGG CAGTACCTTT GATACTGC-3' [SEQ ID NO:5] and 5'-ccggcggccg cAG-GTCCTCT ATAACTGTAA GCCATCTG-3' (for re-PCR) [SEQ ID NO:6], second round Marathon PCR primers: 5'-ccggcggccg cTCACTCTAT CTAGGTGCAA CACCAAGTTC-3' [SEQ ID NO:7] and 5'-ccggcggccg cAATGGGAACT AAGGGTAGAC TCAAAGGAG-3' (for re-PCR) [SEQ ID NO:8]. See, e.g., Chenchik et al., "A new method for full-length CDNA cloning by PCR" In: A Laboratory Guide to RNA: Isolation, Analysis, and Synthesis, Krieg (ed.), pp 273–321 (1996). PCR products were cloned into pBlueScript, and complete sequence was determined based on multiple independent clones. The full-length E6TP1α cDNA used for expression studies was obtained by PCR from mammary gland cDNA using primers that included a NotI restriction site (sense primer: 5'-ccggcggccg cGGTGTGGAC GTTGTCTAA ATTTCGG-TAG CC-3' [SEQ ID NO:9]; and antisense primer:

5'-ccggcggccg cAGGTGCTCT GAGGATGCTT TCTATGG-3' [SEQ ID NO: 10]). This PCR product was cloned into pBlueScript and sequenced. The PCR-generated mutations were corrected by restriction fragment swap with a separate clone. The corrected full-length sequence was cloned through blunt end ligation into BamHI sites of pSG5 to yield PSG5-E6TP1, which was used for in vitro transcription/translation and in vivo expression in mammalian cells. PSG5-E6TP1α-lacking the C-terminal 540 (PSG5-E6TP1-ΔC-540) and 129 aa (PSG5-E6TP1-ΔC-129) were constructed by deleting the BamHI or PstI fragments, respectively, from the full-length E6TP1α (see schematic, FIG. 3B). PSG5-E6TP1-C-378, and PSG5E6TP1-C-194 were derived from two independent pGAD10 clones obtained from the two-hybrid screen, supra. An N-terminal myc tag, together with an initiation codon and a consensus Kozak sequence designed for optimized translation, was appended to the 5' of E6TP1-C-378 and -C-194. GST-E6TP1-C-378 and GST-E6TP1-C-194 were constructed by subcloning the respective cDNA inserts from pGAD10 clones into pGEX2TK. GST-E6TP1-393-1058 was constructed by cloning nucleotides 1524–3517 of E6TP1 as an EcoRI fragment into pGEX4T-3. HPV16 E6 open reading frame was cloned into pGEX2T-K to produce GST-E6. A GST-fusion protein of E6-AP (aa 37 to 865), (GSTE6AP), and its mutant lacking aa 391–408 (GSTE6APmut) were available in the art. See, e.g., Huibregtse et al., *Mol Cell Biol* 13: 4918–4927 (1993). The HPV16, -18, -11 and -6 E6 constructs used for in vitro translation have been described (Chen et al., *Science* 269: 529–531 (1995). The expression vector pSG5-HPV16 E6 was available in the art. For the remaining expression constructs, HPV18 and -11 E6 open reading frames were cloned into pSG5 as EcoRI-HindIII fragments, and HPV6 E6 open reading frame was cloned into pSG5 as a EcoRI-PstI fragment for in vivo expression.

PSG5-HPV16 E6-FLAG was constructed by amplifying HPV16 E6 using PCR with the following primers: sense primer-5'-gcggaattcA TGGACTACAA GGACGACGAT GACAAGTTTC AGGACCCACA GGAGCGACCC AG-3' [SEQ ID NO:11] and antisense primer-5'-gccggatccT TACAGCTGGG TTTCTCTAC GTGTTCTTGA TGA-3' [SEQ ID NO:12]. The sense PCR primer introduced a FLAG tag between the first and second amino acids of the HPV16 E6. The PCR product was digested with the EcoRI and BamHI enzymes and ligated to the EcoRI-BamHI digested pSG5.

Northern Hybridization and Expression Pattern of E6TP1

To verify that E6TP1 corresponded to an expressed human gene and to assess its expression, we performed Northern blot analysis of various tissues and cell lines. As shown in FIGS. 1A, B, and C, E6TP1 mRNA was expressed in all the tissues and in vitro established cell lines tested, although the levels varied. The cell lines included the 76N MEC strain from which the two-hybrid library was constructed, human primary foreskin keratinocytes, immortal and tumor mammary epithelial cell lines, and HPV-positive and HPV-negative cervical cancer cell lines (FIGS. 1B and C).

Figure 1C:
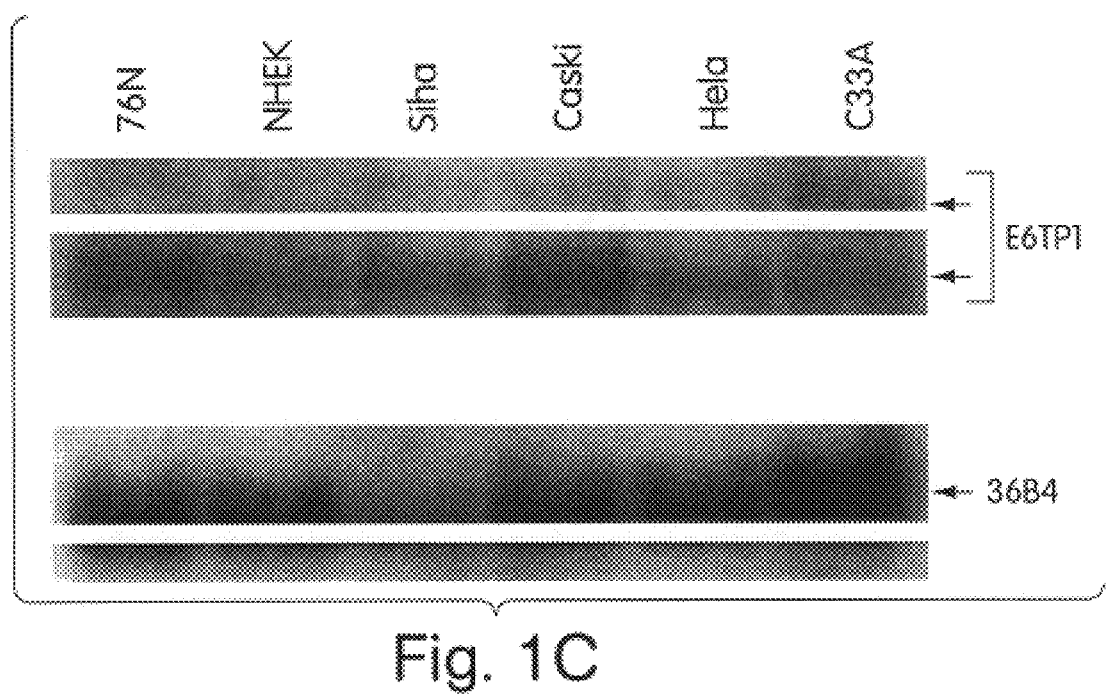

A tissue blot with 2 μg polyA+ mRNA per lane (FIG. 1A) (Clontech) or blot with 20 μg total mRNA from mammary epithelial cell strain 76N, HPV16 E6-immortalized MECs 76E6 and 81E6 or indicated breast cancer cell lines (FIG. 1B), and from normal human epithelial keratinocytes (NHEK), HPV-positive cervical carcinoma cell lines (HeLa, Siha, Caski) and a HPV-negative cervical carcinoma cell line (C33A) (FIG. 1C), were probed with a $^{32}$P-labeled full-length E6TP1 probe and visualized by autoradiography. See, e.g., Band et al., *Proc Natl Acad Sci USA* 87: 463–467 (1990). Hybridization with 36B4 probe was used as a loading control. See, e.g., Laborda, *Nucl Acids Res* 19: 3998 (1991). As shown in FIG. 1, the major E6TP1 mRNA species are indicated by arrows and the size markers in kb are shown on the left.

Two major transcripts of 7.5 and 6.0 kb are evident in essentially all tissues and cell lines, with the 6.0 kb transcript predominating in most cases. The larger 7.5 kb transcript is more abundant in brain tissue. A 2.2 kb transcript is abundant in placenta (FIG. 1A). These analyses show that the E6TP1 cDNA fragments isolated by yeast two-hybrid screening represent an authentic mRNA that is widely expressed in human tissues and in vitro grown cell lines.

Homology Analysis of E6TP1 Polypeptide Sequence

Figure 2D:
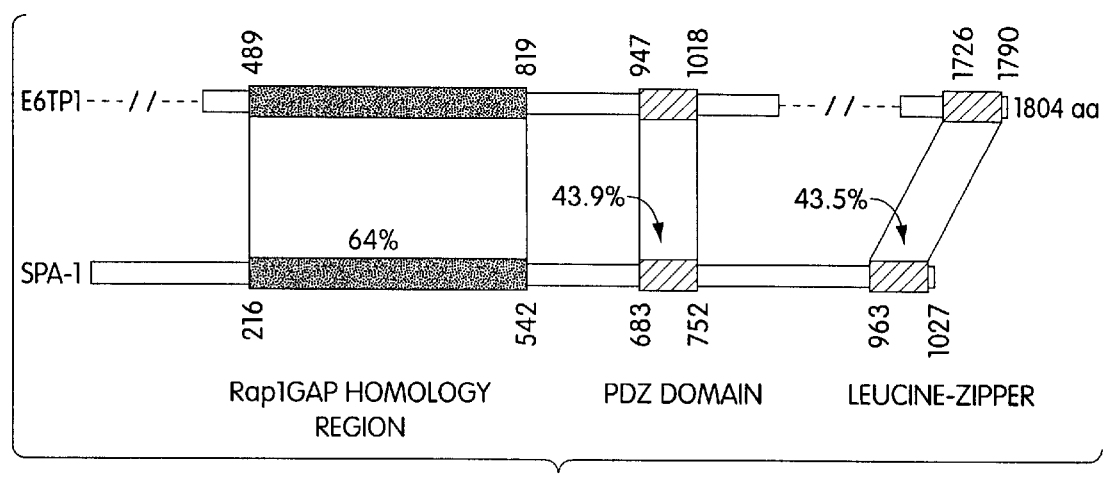
FIG. 2 illustrates: (Panel A) the predicted amino acid sequence of human E6TP1α isoform [SEQ ID NO:2] determined from E6TP1α full length complementary DNA ("cDNA") nucleotide sequence (GeriBank Accession Number AF090989) [SEQ ID NO:1]; (Panel B) the E6TP1β isoform-specific 21 amino acids (SEQ ID NO:13), located immediately after amino acid residue 1215 of Panel A, determined from full length E6TP1β cDNA nucleotide sequence [SEQ ID NO:3] and predicted amino acid sequence [SEQ ID NO:4] (GenBank Accession Number AF090990); (Panel C) an amino acid sequence alignment of E6TP1α to known GAP proteins; and (Panel D) a schematic alignment of E6TP1 with human SPA-1.

Although the E6TP1 sequence represent a novel cDNA sequence, a Gapped BLASTP search of the NCBI database showed that E6TP1 residues 489–819 share high sequence identity with GAP domains of known and putative RapGTPase-activating proteins (GAPs). The proteins with highest homology to E6TP1 include the mammalian GAPs Rap1GAP, tuberin (the tuberous sclerosis complex 2 product, TSC2), and SPA-1 (FIGS. 2C and D), as well as Drosophila Rapgap1 and two putative RapGAPs in *C. elegans*, predicted by the open reading frames identified in genomic sequences (Table 1). FIG. 2C represents an amino acid sequence alignment of E6TP1α to known GAP proteins (e.g., human tuberin, human SPA-1, and human Rap1GAP), wherein homology comparisons were made using the Clustral algorithm with a gap penalty of 3 and refined by manual adjustment. The schematic in FIG. 2D illustrates our alignment of E6TP1 with human SPA-1. Numbers indicate the beginning and ending amino acid positions of homologous regions. Percent homology is indicated with each region. Homology with SPA-1 extends beyond the GAP domain and includes the putative leucine zipper region (47% identity between E6TP1α aa 1705–1779 or E6TP1β aa 1726–1790 versus SPA-1 residues 963 to 1027), as well as other regions, with an overall 42% amino acid identity between E6TP1 residues 319–1205 and SPA-1 residues 104–930. See, e.g., Kurachi et al., *J Biol Chem* 272: 28081–28088 (1997).

Profilescan analysis at ISREC profilescan Server (http://www.ch.embnet.org/software/PFSCAN_form.html) detected a PDZ domain at aa 947–1018 in E6TP1. PDZ domains, named after proteins in which they were originally identified including the post-density synaptic protein PSD-95, the Drosophila discs large gene product (Dlg), and the tight junction protein ZO1, have been found in over 50 different proteins. One known function of these modular domains is to promote sub-membranous protein complexes by binding to C-termini of target proteins. See, e.g., Ponting et al., *Bioessays* 19: 469–479 (1997). The E6TP1 PDZ domain showed 43% sequence identity with residues 683–752 of SPA-1, indicating that SPA-1 also contains a PDZ domain and that this domain is conserved between E6TP1 and SPA-1. The E6TP1 PDZ domain also showed a 36% identity with the second PDZ domain of the neuronal protein X11 (aa 613–683). See, e.g., Borg et al., *Mol Cell Biol* 16: 6229–6241 (1996); Duclos et al., *Proc Natl Acad Sci USA* 90: 109–113 (1993). Overall, the comparison of the amino acid sequences of E6TP1 with known proteins suggests that E6TP1 functions as a GAP towards Rap and/or other small GTPase.

A search of the NCBI Sequence Tagged Site (STS) database (http://www.ncbi.nlm.nih.gov/cgi-bin/SCIENCE96/ssrch), containing 20,043 gene-based STSs and 5,264 polymorphic STSs in the Genethon genetic map (see, e.g., Dib et al., Nature 380: 152–154 (1996); Schuler et al., Science 274: 540–546 (1996), revealed a DNA sequence match between E6TP1 and STS A006F03 (accession #G20753), SHGC-2959 (accession #T17112) and WI-9040 (accession #G06003). These STSs have been localized to human chromosome 14 regions 14q23.2–q24.3. Interestingly, this region is known to undergo loss of heterozygosity in malignant meningiomas. See, e.g., Menon et al., Oncogene 14: 611–616 (1997); Simon et al., Cancer Res 55: 4696–4701 (1995); Tse et al., Hum Pathol 28: 779–785 (1997).

In Vitro Binding Between E6TP1 and HPV E6 Proteins

The indicated proteins were translated in vitro in the presence of $^{35}$S-cysteine (HPV E6 proteins, E6TP1α, E6TP1α-ΔC-540 or E6TP1-ΔC-129) or $^{35}$S-methionine (E6TP1-C-378 and -C-194) (NEN, MA) using a wheat germ lysate-based coupled transcription/translation system (TNT wheat germ lysate system; Promega, WI.) according to supplier's recommendations. The $^{35}$S-labeled in vitro-translated proteins were incubated with 1 μg of appropriate GST fusion proteins non-covalently bound to glutathione beads in 300 μl lysis buffer (100 mM Tris, pH 8.0, 100 mM NaCl, 0.5% NP-40) for 2 hours at 4° C., and bound $^{35}$S-labeled proteins were resolved by sodium dodecyl sulfate-polyacrylamide gel electrophoresis (SDS-PAGE) and visualized by fluorography. See, e.g., Chen et al., Science 269: 529–531 (1995).

To further confirm the interaction between HPV E6 proteins and E6TP1, we assessed the binding of GST-E6TP1-C-378 (a GST fusion protein of the C-terminal 378 residues of E6TP1 encoded by the longer yeast two-hybrid cDNA clone to in vitro-translated $^{35}$S-labeled E6 polypeptides. GST-E6AP (aa 37–865; a positive control, but not its mutant lacking the 18 aa E6-binding motif, or GST alone, showed substantial binding to HPV16 and -18 E6 proteins but little binding to HPV6 or -11 E6 proteins. See, e.g., Huibregtse et al., Mol Cell Biol, 13: 4918–4927 (1993). Importantly, the GST-E6TP1-C378 showed a substantially higher level of binding to the high-risk HPV (-16 and -18) E6 proteins, with little binding to the low-risk HPV (-6 and -11) E6 proteins (FIG. 3A). Thus, similar to E6-AP, E6TP1 selectively binds to high risk HPV E6 proteins.

In contrast to HPV E6 binding to hDlg, which binds to E6 through a PDZ domain, E6TP1 mutants that contained the PDZ domain but lacked the C-terminal sequences failed to bind to E6 (FIGS. 3A and 3B). Furthermore, C-terminal 194 aa of E6TP1 were sufficient to bind to E6. See, e.g., Kiyono et al., Proc Natl Acad Sci USA, 94: 11612–11616 (1997).

In vitro and in vivo Degradation of E6TP1 Induced by High-risk HPV E6 Proteins

Cos-7 cells were transfected with pSG5E6TP1-C-194 encoding the myc-tagged E6TP1-C194 fragment and pSG5-HPV16E6 encoding the FLAG-tagged HPV16E6 using the Lipofectamine reagent according to the manufacturer's method (Life Technologies, MD.). Forty-eight hours after transfection, cells were harvested in lysis buffer (100 mM Tris pH 8.0, 100 mM NaCl, 0.5% nonidet P-40 and 1 mM phenylmethylsulfonyl fluoride), precleared twice with protein G-agarose, and incubated with anti-myc antibody ("9E10", available in the art) for 4 hours at 4° C. The samples were washed 6 times with lysis buffer, resuspended in sample buffer, resolved on 17% SDS-PAGE, transferred to a PVDF membrane, blotted with anti-FLAG monoclonal antibody M2 (Sigma, MO.), and detected using the enhanced chemiluminescence (ECL) detection system (Amersham, CA.).

Among the previously identified E6-binding proteins, only p53 (but not ERC55, paxillin, and hDlg) is known to be targeted by E6 for ubiquitin-proteasome-mediated degradation. See, e.g, Huibregtse et al., Mol Cell Biol, 13: 4918–4927 (1993). To examine if E6TP1 was a target of E6-induced degradation, in vitro translated HPV E6 proteins were incubated with full-length E6TP1 or its fragments in a rabbit reticulocyte lysate and E6TP1 degradation was assayed. The high risk (HPV-16) but not the low-risk (HPV-6) E6 protein induced the degradation of E6TP1 as well as of the positive control polypeptide p53 (FIG. 4A). Similarly, the HPV18 E6 was able to degrade E6TP1, whereas the HPV11 E6 was unable to do so (data not shown). Interestingly, all four partial fragments of E6TP1 (ΔC-540, ΔC-129, C-194, C-378) were deficient in degradation even though E6TP1-C-194, and E6TP1-C-378 efficiently bind to E6 (as shown in FIG. 3B), indicating that binding of E6 by itself is not sufficient for E6TP1 degradation.

In order to assess the E6TP1 degradation in vivo, the E6TP1 and E6 cDNAs were transiently co-transfected in 293T cells. The lysates of these cells were subjected to immunoblotting with a rabbit polyclonal antibody raised against GST-E6TP1-C378 and specific to E6TP1. This antibody did not detect the endogenous E6TP1 in 293T cells (probably reflecting its low titer) but did efficiently detect the exogenously introduced E6TP1 (FIG. 4). Co-expression of high risk (-16 and -18) but not the low-risk (-6 and -11) HPV E6 proteins drastically reduced the level of E6TP1 protein (FIG. 4B). Thus, similar to p53, the E6TP1 protein is targeted for in vitro and in vivo degradation by high-risk but not the low-risk HPV E6 oncoproteins.

E6-induced in vitro Degradation Assay

For degradation assay, the various proteins were translated in vitro in the presence of $^{35}$S-cysteine (HPV E6 proteins or their mutants, and E6TP1α, E6TP1α ΔC-540, E6TP11α ΔC-129 or p53) or $^{35}$S-methionine (E6TP1-C-378 and E6TP1-C-194using a rabbit reticulocyte lysate-based coupled transcription/translation system (TNT rabbit reticulocyte lysate system; Promega, WI.). Five μl of each in vitro-translated $^{35}$S-labeled protein were incubated together with 5 μl of HPV E6 or water-primed (control) lysate. After 5 hours at 30° C., the degradation reaction was stopped by adding 100 μl sample buffer. Proteins were resolved by SDS-PAGE and visualized by fluorography.

E6-induced in vivo Degradation of E6TP1

5×10$^5$ 293T cells in a 100-mm diameter dish were transfected with 10 μg DNA of pSG5 vector or pSG5 constructs encoding the indicated proteins using the polyamine reagent (Panvera, CA.), according to the manufacturer's protocol. The total amount of DNA was held constant at 20 μg per dish by adding vector DNA. Cells were harvested after 48 hrs, and 400 μg of total protein was resolved on 6% SDS-PAGE and transferred to a PVDF membrane. Membranes were blotted with a rabbit anti-E6TP1 antiserum (raised against GST-E6TP1-C-378), and detected using enhanced chemiluminescence ("ECL") (Amersham, CA.).

Immunoprecipitation of Transfected HPV E6

293T cells transfected as above were labeled with 300 μCi/ml of $^{35}$S-cysteine (ICN) for 4 hours, and lysates were prepared in RIPA buffer (0.15M NaCl, 50 mM Tris, pH 7.4, 1 mM EDTA, 1% Triton X-100, 1% DOC, 0.1% SDS). See, e.g, Androphy et al., EMBO J 6: 989–992 (1987). HPV16 E6 protein or its mutants were immunoprecipitated using a rabbit anti-HPV16 E6 antiserum. See, e.g, Wazer et al., Proc Natl Acad Sci USA 92: 3687–3691 (1995). The immunoprecipitated E6 proteins were resolved on 12% SDS-PAGE, and visualized by fluorography.

Example 2

Binding of E6TP1 and HPV E6 Proteins
Binding of E6TP1 and HPV E6 proteins in vitro To further confirm the interaction between HPV E6 proteins and E6TP1, we prepared a GST fusion protein encoding the C-terminal 378 residues of E6TP1 representing the sequences present in the longer cDNA clone isolated in the yeast two-hybrid screening. Various E6 proteins were translated in vitro in wheat germ lysate in the presence of $^{35}$S-methionine or cysteine. These $^{35}$S-labeled E6 proteins were allowed to bind to GST, GSTE6TP1 (C-terminal 378 aa of E6TP1 fused to GST), GSTE6AP or GSTE6APmut (E6-AP lacking aa 391–408) (FIG. 3A). Input represent an aliquot of 10% labeled E6 proteins used in the binding reactions. In a second experiment, full length E6TP1α or its truncated versions (FIG. 3B, with amino acid designations in the adjacent schematics) were translated in vitro in wheat germ lysate, and the $^{35}$S-labeled proteins were allowed to bind to GST or GST-HPV16 E6. In a third experiment, binding between GST fusion proteins incorporating different regions of E6TP1 (FIG. 3C, as indicated) and $^{35}$S-labeled HPV16 or -6 E6 generated by in vitro translation in wheat germ lysate were analyzed. In FIGS. 3A–3C, bound HPV E6 proteins were analyzed by SDS-PAGE and visualized by fluorography.

As shown in FIG. 3A, GST-E6AP (aa 37–865), herein used as a positive control (see, e.g., Huibregtse et al., *Mol Cell Biol* 13: 4918–4927 (1993), showed substantial binding to HPV16 and -18 E6 proteins but little binding to HPV6 or -11 E6 proteins, as expected. Neither GST nor GST-E6AP mutant (D391–408, which lacks the 18 aa E6 binding motif (see, e.g., Huibregtse et al., *Mol Cell Biol* 13: 4918–4927 (1993)), bound to the HPV E6 proteins above background level, demonstrating the specificity of binding. Importantly, the GST-E6TP1 protein showed substantially higher level of binding to the high-risk HPV E6 proteins (-16E6 and -18E6), with relatively low binding to the low-risk HPV E6 proteins (-6E6 and -11E6). Thus, similar to E6-AP, E6TP1 appears to selectively bind to E6 proteins of high risk HPVs.

A recent study showed that the human homologue of the Drosophila discs large (Dlg) tumor suppressor protein binds to E6 oncoprotein of the high risk HPVs through a PDZ domain, and mutation of this domain abolished the hDlg interaction with E6 protein. See, e.g., Kiyono et al., *Proc Natl Acad Sci USA* 94: 11612–11616 (1997). Therefore, it became important to determine if E6TP1 also uses its PDZ domain for interaction with the HPV E6 oncoprotein. Although the above binding experiments demonstrated that the C-terminal 378 residues of E6TP1, which lack the PDZ domain, were sufficient for E6 binding, it remained possible that the PDZ domain of E6TP1 could also bind to E6, either independently or cooperatively with the C-terminal region. To further define the binding domain(s) of E6TP1, we utilized two series of reciprocal binding experiments. In one approach, a set of E6TP1 mutants were in vitro translated in wheat germ lysate and incubated with either GST or GST-HPV16 E6 fusion proteins. As shown in FIG. 3B, the full-length E6TP1, as well as E6TP1-C-194 or E6TP1-C-378 prominently bound to E6, whereas relatively poor binding was observed with E6TP1-ΔC-540 and E6TP1-ΔC-1 29 proteins. In a reciprocal experiment, different regions of E6TP1 were expressed as C-terminal fusions with GST and used for binding assays with in vitro translated HPV16 E6 (FIG. 3C). These analyses confirmed the results obtained in FIG. 3B. Together, these analyses localize the E6 binding site in E6TP1 within the C-terminal 194 residues, and show that the PDZ domain contributes little if any toward E6 binding. Thus, E6TP1 utilizes a mechanism distinct from that of the hDlg protein to interact with E6.

Binding of E6TP1 and HPV16 E6 Protein in vivo

In order to demonstrate that E6 binds to E6TP1 in vivo, Cos-7 cells were transfected with 10 μg each of pSG5, myc-tagged E6TP1-C-194, FLAG-tagged-HPV16 E6 or myc-tagged E6TP1-C-194 plus FLAG-tagged HPV16 E6, as indicated in FIG. 4. 48 hours after transfection, cells were lysed in lysis buffer and E6TP1-E6 complex was immunoprecipitated using the "9E 10" anti-myc monoclonal antibody, followed by Western blotting for E6 using the anti-FLAG antibody (FIG. 4, left panel). Direct anti-FLAG Western blotting of whole cell lysate (FIG. 4, right panel) indicates the expression of HPV16 E6 in the transfected cells.

These Cos-7 cell transfections were designed to express myc-tagged E6TP1-C194 fragment and FLAG-tagged E6 protein either alone or together. As expected, no E6 protein was detected in immunoprecipitates of cells transfected with either vector alone or with the two constructs transfected individually (FIG. 4, lanes 1, 2, 3). In contrast, E6 protein was clearly detected in anti-myc immunoprecipitates of cells co-transfected with both constructs (FIG. 4, lane 4, left panel). Western blotting of whole cell lysates (FIG. 4, right panel) indicated that HPV-16 E6 was similarly expressed when transfected both with and without E6TP1. These results clearly demonstrate that E6 is able to bind E6TP1 in vivo. We observed similar results upon transfection of these constructs in 293T cells.

In vitro and in vivo Degradation of E6TP1 Induced by High-risk HPV E6 Proteins

The high risk HPV E6 proteins are known to target p53 for degradation via the E6-AP-mediated ubiquitination pathway. See, e.g., Huibregtse et al., *Mol Cell Biol* 13: 775–784 (1993); Huibregtse et al., *Mol Cell Biol* 13: 4918–4927 (1993); Scheffner et al., *Cell* 75: 495–505 (1993). Since E6TP1 showed a selective interaction with high-risk HPV E6 proteins, we tested whether E6TP1 was also a target of E6-induced degradation. For this purpose, HPV16 E6, HPV6 E6, p53, full-length E6TP1, and various fragments of E6TP1 were translated in vitro in a rabbit reticulocyte lysate system in the presence of $^{35}$S-methionine or cysteine, and subjected to degradation assays such that the $^{35}$S-labeled E6TP1α (5 μl) was incubated with water-primed lysate (control) or various E6 proteins (5 μl each) for 5 hr. The E6TP1 remaining at the end of degradation assay was analyzed by SDS-PAGE and visualized by fluorography. The results are shown in the individual panels of FIG. 5A, wherein the upper five panels show E6TP1 and various fragments of E6TP1, and the bottom panel shows the HPV16 or -6 E6 proteins used in the degradation assay. The p53 panel is shown as the control.

The high risk HPV16 E6 induced the degradation of E6TP1 as well as that of p53 (FIG. 5A), but the low-risk HPV6 E6 did not induce degradation of either the E6TP1 or p53. The water-primed control lysate (FIG. 5A, lanes 1 of each panel) did not show any effect, as expected. The bottom panel shows that similar amounts of HPV16 and HPV-6 E6 proteins were present in the degradation assays. Additional experiments showed that the E6 protein of a second high risk HPV (HPV18) was also able to degrade E6TP1, whereas that of the low risk virus HPV11 was unable to do so. Interestingly, all four partial fragments of E6TP1 (ΔC-540, ΔC-129, C-1 94, C-378) were. deficient in degradation even though E6TP1-C-194, and E6TP1-C-378 efficiently bind to E6 (as shown in FIG. 3B). These results indicate that binding of E6 to E6TP1 by itself is not sufficient for degradation.

Figure 5B:
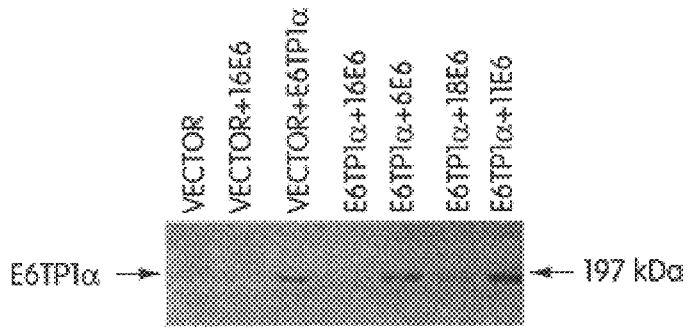

In order to assess the in vivo degradation of E6TP1 protein, we co-expressed the E6TP1 and E6 proteins of HPV-16, -18, -11, and -6, in 293T cells. See, e.g., Duclos et al., Proc Natl Acad Sci USA 90: 109–113 (1993); Dyson et al., Science 243: 934–937 (1989). $5 \times 10^5$ 293T cells in dishes were transfected with 10 μg each of indicated HPV E6 constructs together with E6TP1α in pSG5 vector using the polyamine reagent. Total amount of DNA per dish was kept constant at 20 μg. Cells were harvested after 48 hr and 400 μg aliquots of lysates were resolved by 6% SDS-PAGE. The lysates of these cells were subjected to immunoblotting with a rabbit polyclonal antibody specific to E6TP1 followed by ECL detection. This antibody did not detect endogenous E6TP1 in 293T cells allowing an assessment of the effect of E6 co-expression on the levels of introduced E6TP1. Co-expression of E6 proteins of high risk HPVs drastically reduced the level of E6TP1, whereas the levels of E6TP1 were similar to controls upon co-expression of E6TP1 with low-risk HPV6 and -11 E6 proteins (FIG. 5B). Immunoprecipitation with antibodies specific to HPV16 E6, -6 E6, and -18 E6 showed that these proteins were expressed in these experiments at comparable levels, whereas the levels of HPV11 E6 could not be assessed due to lack of an antibody. We conclude from these experiments that E6 proteins from high-risk but not low-risk HPVs can induce in vitro as well as in vivo degradation of E6TP1.

In addition, our most recent experiments show that the dominant negative E6-AP C833A mutant can inhibit E6 induced E6TP1 degradation in vivo in 293T cells.

Example 3

E6TP1 Degradation by Immortalizing but not Non-immortalizing E6 Mutants

Figure 6A:
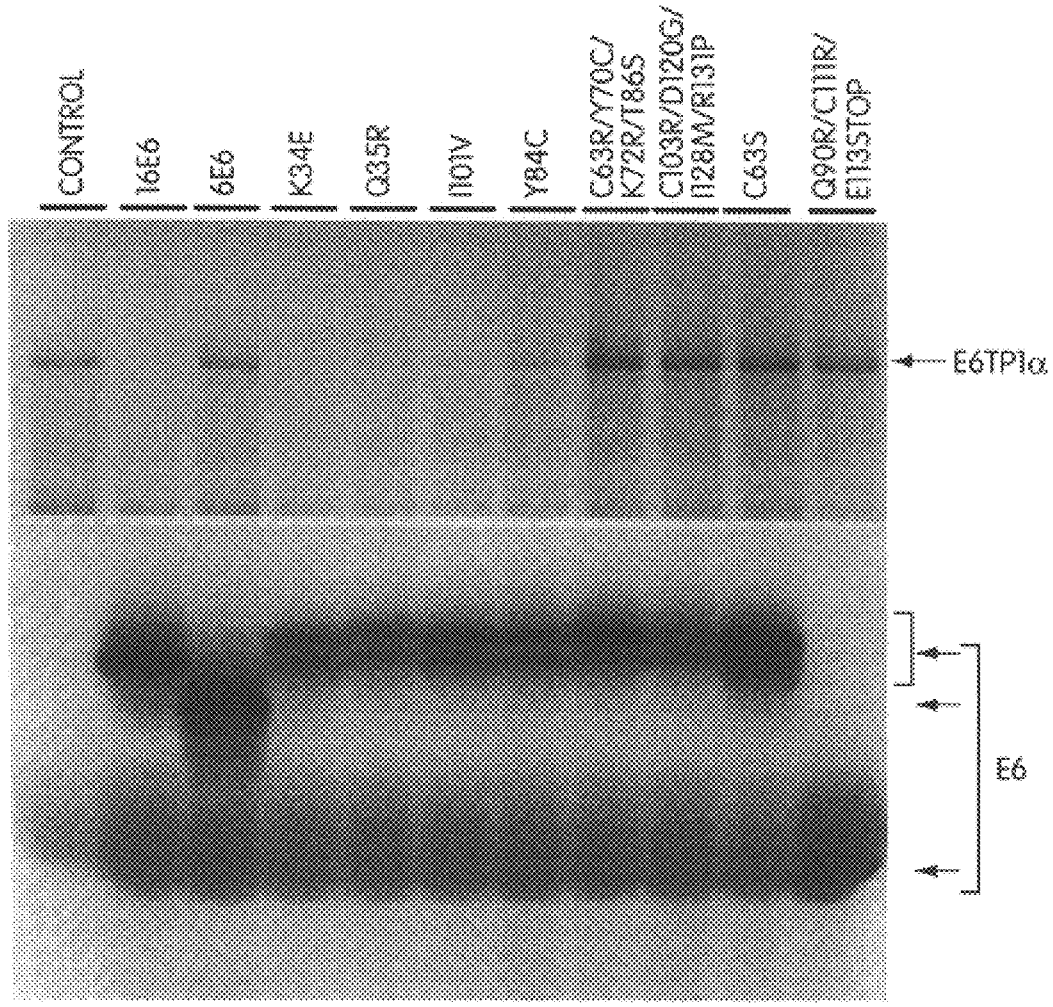
FIG. 6 illustrates degradation of E6TP1 by immortalizing and non-immortalizing HPV16 E6 mutants: (Panel A) in vitro degradation, wherein arrows indicate the locations of E6TP1 and E6 proteins; (Panel B) in vivo degradation, wherein arrows indicate E6TP1; and (Panel C) expression of mutant E6 proteins in transfected 293T cells.
Figure 6B:
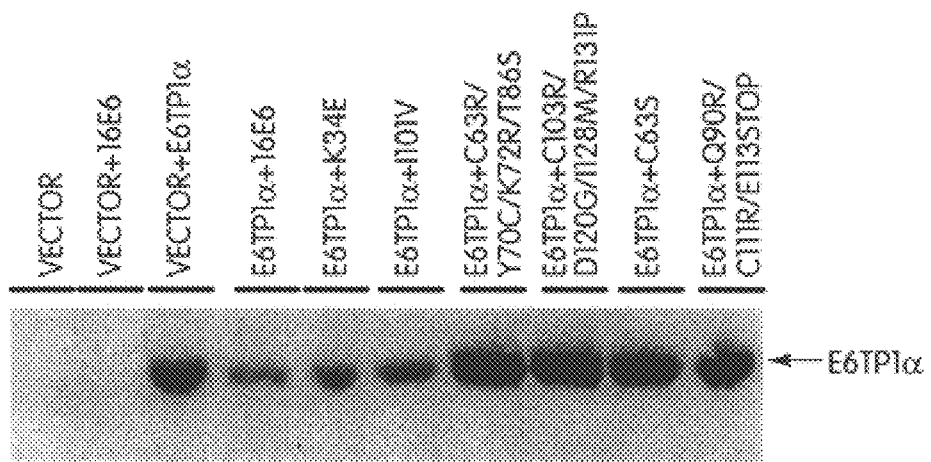
Figure 6C:

Previous analyses of HPV16 E6 have identified immortalizing and non-immortalizing mutants of HPV16 E6, and have demonstrated that immortalizing mutants selectively induce degradation of p53 protein. See, e.g., Dalal et al., J Virol 70: 683–688 (1996). Therefore, we used in vitro as well as in vivo degradation assays to examine whether the ability of E6 protein to induce E6TP1 degradation correlates with their immortalizing abilities. For in vitro analysis of E6TP1 degradation by mutant E6 proteins (see Tables 2 and 3 for details), E6TP1α, HPV16 E6 and its mutants were translated in vitro in rabbit reticulocyte lysate in the presence of $^{35}$S-cysteine. Degradation assays were performed as in Example 2 (FIG. 5A) followed by SDS-PAGE and immunoblotting. Results are shown in FIG. 6A, wherein arrows indicate the locations of E6TP1 and E6 proteins. For in vivo degradation analysis, HPV16 E6 or its mutants were co-transfected with vector or E6TP1 into 293T cells followed by assessment of E6TP1 protein levels by anti-E6TP1 immunoblotting as in Example 2 (FIG. 5B), followed by SDS-PAGE and immunoblotting (FIG. 6B). As a control, expression of mutant E6 proteins in transfected 293T cells was analyzed (FIG. 6C). Paired dishes of 293T transfectants shown in FIG. 6B were labeled with $^{35}$S-cysteine and lysates were immunoprecipitated with an anti-E6 antibody. Bound proteins were resolved by 12% SDS-PAGE and visualized by fluorography.

As shown in FIGS. 6A–B and Tables 2 and 3, both in vitro and in vivo experiments demonstrated that, similar to wild-type E6, E6 mutants capable of immortalizing mammary epithelial cells were also efficient in inducing E6TP1 degradation. In contrast, E6 mutants that are deficient in mammary epithelial cell immortalization were also incapable of inducing E6TP1 degradation, even though all E6 proteins were expressed at easily detectable levels (FIG. 6C). Thus, the ability of HPV16 E6 mutants to target E6TP1 for degradation directly correlates with their immortalizing ability.

TABLE 3

In vitro and in vivo degradation of E6TP1α by HPV16 E6 mutants.

| Construct | Degradation in vitro | Degradation in vivo | Immortalization [a] |
|---|---|---|---|
| HPV16 E6 | + | + | + |
| Lys-34 Glu* | + | + | + |
| Gln-35 Arg* | + | + | + |
| Tyr-54-His* | ND | + | + |
| Tyr-54-Asp* | ND | + | + |
| Tyr-84 Cys* | + | + | + |
| Ile-101 Val* | + | + | + |
| Gln-107-Leu* | ND | + | + |
| Pro-109-Ser* | ND | + | + |
| Pro-109-Thr* | ND | + | + |
| Cys-111-Ser* | ND | + | + |
| Cys-63 Ser* | − | − | +/− |
| Cys-63 Arg/Tyr-70 Cys*/Lys 72 Arg/Thr-86 Ser | − | − | − |
| Cys-103 Arg/Asp-120 Gly*/Ile-128 Met/Arg-131 Pro | − | − | − |
| Gln-90 Arg/Cys-111 Arg*/Glu-113 Stop | − | − | − |
| Δ9–13[#] | ND | − | − |
| Δ73–77[#] | ND | − | − |
| Δ78–82[#] | ND | − | − |
| Δ96–100[#] | ND | − | − |
| Δ101–105[#] | ND | − | − |
| Δ106–110[#] | ND | − | − |
| Δ111–115[#] | ND | − | − |
| Δ118–122[#] | ND | − | − |
| Δ123–127[#] | ND | − | − |
| Δ133–137[#] | ND | − | − |
| Δ143–147[#] | ND | − | − |

*These HPV16 E6 mutants and immortalization experiments are described in detail in Dalal et al., J. Virol., 70: 683–688 (1996) (incorporated herein by reference in its entirety).
[#]These mutants are from Crook et al., Cell, 67: 547–556 (1991).
+ Mutants able to degrade E6TP1 and immortalize MECs.
− Mutants that are unable to degrade E6TP1 and do not immortalize MECs.
+/− Rare immortalization events were observed.
ND Not done.

Example 4

Anti-E6TP1 Antibody Production

Initial Production and Characterization of Anti-E6TP1 Antibody

We have prepared two kinds of antibodies, anti-GST-E6TP1 fusion protein antibodies and anti-E6TP1 peptides antibodies. Anti-GST E6TP1 fusion protein antibodies were prepared with GST-E6TP1 C-378 as immunogen. Briefly, GST-E6TP1 C-378 fusion protein emulsified in the synthetic adjuvant Titremax (CytRx Corp., Norcross, Ga.) was injected subcutaneously into rabbits at 50 μg per rabbit. After three initial injections given at day 1, day 28, and day 35, respectively, the rabbits were subsequently boosted every month thereafter. Blood samples were obtained to check their reactivity against E6TP1 transfected 293T cell lysates by Western blotting.

The anti-E6TP1 peptide antibodies were prepared against 4 E6TP1 peptides. Three of the 4 peptides are common to E6TP1α and β (E6TP1α aa 86–102, 1063–1077, 1521–1535) and one peptide is unique to E6TP1β (aa 1218–1227). These peptides were chosen because they are unique to E6TP1, and are predicted to be hydrophilic and immunogenic. Peptides were HPLC-purified, coupled to keyhole limpet hemocyanin ("KLH") via an introduced C-terminal cysteine using the cross-linker maleim-idobenzoyl-N-hydroxysuccinimide ester. Two rabbits per peptide were subcutaneously injected with 150 µg peptide-KLH conjugate emulsified in Freund's complete adjuvant at day 1, and boosted at day 28, 35, 42, 49, 56, 77, 84, 91, 98, 105 with 100 µg peptide-KLH conjugate emulsified in Freund's incomplete adjuvant. Blood samples were obtained at day 42, 49, 56, 77, 84, 91, 105 and tested for reactivity by immunoprecipitation and immunoblotting against E6TP1-transfected 293T cells.

We also plan to develop monoclonal antibody. E6TP1 purified from insect expression system will be used as antigen. Groups of 5 female Balb/C mice will be intraperitoneally injected with purified E6TP1 polypeptides (200 µg/mouse) in Titremax adjuvant followed by monthly boosts in the same adjuvant. The antibody titer in tail bleeds will be monitored by immunoblotting and immunoprecipitation and mice with high titers will be used for derivation of monoclonal antibodies using procedures described in Lane and Harlow, 1988, In: Antibody, A Laboratory Manual, Cold Spring Harbor Laboratory press, New York. Reactive hybridomas will be cloned by limiting dilution technique, and antibodies will be tested by immunoblotting and immunoprecipitation.

Development of High Specificity Anti-E6TP1 Antibodies

Initial cloning has identified two alternative splice products, designated E6TP1α and E6TP1β; E6TP1β has an in-frame 63 bp insert after nucleotide 4025 in E6TP1α (FIGS. 2A and 2B). Our rabbit anti-GST-E6TP-C378 antibodies, supra, efficiently detects the exogenous overexpressed E6TP1, but not the endogenous E6TP1, in cells that are mRNA-positive. Therefore, we have selected 4 peptides as immunogens, three common to E6TP1α and β (E6TP1α aa 86–102, 1063–1077, 1521–1535) and one unique to E6TP1 (aa 1218–1227) (FIGS. 2 and 7). The underlined amino acid residues in FIG. 7 represented the 4 selected peptides. Said peptides are unique to E6TP1, and are predicted to be hydrophilic and immunogenic. Hydrophilicity was calculated using the Kyte-Doolittle method and the antigenic index was calculated using the Jameson-Wolf method. Peptides will be HPLC-purified, coupled to keyhole limpet hemocyanin (KLH) via an introduced C-terminal cysteine using the cross-linker maleim-idobenzoyl-N-hydroxysuccinimide ester (Pierce). Based on our previous experience, two rabbits per peptide will be subcutaneously injected with 100 mg peptide-KLH conjugate emulsified in a synthetic adjuvant Titremax (CytRx Corp. Norcross, Ga.) at monthly intervals. 10 days after third and subsequent injections, blood samples will be obtained from the ear vein. The antisera will be initially tested for reactivity by immunoprecipitation and immunoblotting against E6TP1-transfected 293T cells in comparison to our previous anti-GST-E6TP1-C374 antisera. The specificity of antisera will be tested using 293T cells transfected with E6TP1α and β or SPA-1. To generate the E6TP1 expression construct, a SacII and BamHI fragment (nucleotides 3448 to 4200 of E6TP1β) will be swapped for the corresponding fragment (nucleotide 3448–4137) in existing pSG5-E6TP1α (FIG. 2). The sera with the expected specificity and high titers will be affinity purified using the immunizing peptide conjugated to BSA.

In addition, we will generate monoclonal antibodies against E6TP1. E6TP1α and β will be His-tagged, cloned in pBacPAK9 baculovirus vector and expressed in insect cells. See, e.g., Liu et al., In: Antibodies. A Laboratory Manual. Cold Spring Harbor Laboratory (1988). Groups of female Balb/C mice will be intraperitoneally injected with Nickel affinity column-purified E6TP1α or β, polypeptides (200 mg/mouse) in Titremax adjuvant followed by monthly boosts in the same adjuvant. The antibody titer in tail bleeds will be monitored by immunoprecipitation (as above) and mice with high titers will be used for derivation of monoclonal antibodies, using standard procedures. See, e.g., Harlow and Lane, eds. In: Antibodies. A Laboratory Manual. Cold Spring Harbor Laboratory (1988). Reactive hybridomas will be cloned by limiting dilution and antibodies will be characterized for specificity as delineated above.

The specific anti-peptide and/or monoclonal antibodies will be used in immunoprecipitation analyses of $^{35}$S-met/cys-labeled untransfected cells (e.g., 76N and other E6TP1 mRNA-positive cells) to assess their recognition of the endogenous E6TP1 polypeptide(s). The identity of the antibody-reactive polypeptides will be assessed by their tryptic peptide map and two-dimensional gel comparison with transfected E6TP1α and β. Furthermore, immunoblotting and/or immunodepletion with E6TP1β-specific antipeptide antibody can be used to farther verify the identity of the polypeptides.

Example 5

Effects of Overexpression of E6TP1 on Cell Cycle and Senescence in Normal MECs

If E6TP1 participates in a growth-inhibitory pathway, then similar to p53, and E6TP1-related GAP proteins (e.g, tuberin and SPA-1), its overexpression in normal cells is predicted to exaggerate the inhibitory controls on cell growth. This may manifest as reduced cellular proliferation, induction of cell cycle arrest or apoptosis, or premature senescence. We will introduce E6TP1 into normal MECs (e.g., 76N) by retroviral infection which has been successfully used in the laboratory for efficient expression of proteins in nearly 100% of cells. See, e.g., Wazer et al., *Proc Natl Acad Sci USA,* 92: 3687–3691(1995). E6TP1 will be cloned into pLXSN vector, transfected into PA317 packaging cell line, and clones of PA317 cell line expressing high levels of E6TP1 protein will be isolated. Supernatants of these PA317 cells transfected with either vector, sense E6TP1, or antisense E6TP1, will be added to logarithmically growing normal MEC strain 76N and either examined transiently after 48 hours or after selection in G418 (selectable marker in pLXSN vector) for proliferation, cell cycle arrest, apoptosis, and cell senescence. E6TP1 expression will be examined by anti-E6TP1 immunoblotting and/or immunoprecipitation.

The effect on cell proliferation will be quantified by $^3$H-thymidine uptake and cell numbers at different time points in culture. To ensure that subtle effects can be discerned, cell proliferation will be assessed at various concentrations of essential growth factors such as EGF. Cellular senescence will be assessed by comparing the passages at which an increase in cell number fails to occur upon regular subculture, and morphological changes of senescence are visible. Normal MECs invariably senesce in culture at passage 15–20 making it feasible to assess an earlier onset of senescence. The cell cycle distribution will be analyzed by the fluorescence-activated cell sorter (FACS) of the propidium iodide/bromodeoxyuridine stained cells (through core FACS facility at the Tufts Medical Center). In these analyses, transfection of wild-type p53 will serve as an internal control that is known to reduce cell proliferation and induce G1 cell cycle arrest. See, e.g., Baker et al., *Science,* 249: 912–915 (1990). Apoptosis will be assessed using the Tunnel assay or ELISA methods (Boehringer Mannheim)

which have been found suitable for MECs (data not shown). See, e.g., Sumantran et al., *Cancer Res.*, 55: 2507–2510 (1995) and Cavrieli et al., *J. Cell Biol.*, 119: 493–501 (1992).

Based on our hypothesis, we anticipate that overexpression of sense but not antisense E6TP1 or vector alone will reduce proliferation of normal MECs, and may induce cell cycle arrest or apoptosis. These results will be used to assess the appropriate levels for treatment of non-HPV associated diseases and neoplasms.

Example 6

Effect of E6TP1 Overexpression on HPV E6 Function

We hypothesize that inactivation of E6TP1 function is important for E6-induced immortalization. If this is the case, then overexpression of E6TP1 may be expected to reduce the efficiency with which E6 induces MEC immortalization. Therefore, we will transfect 76N MECs with vector, sense E6TP1 or antisense E6TP1 together with E6 using the retroviral system (described in Example 5, supra), and examine the frequency of immortalization. E6TP1 will be used in LXSN vector (G418-selectable marker) and E6 in the pBabepuro vector (puromycin-selectable marker). See, e.g., Wazer et al., *Proc Natl Acad Sci USA*, 92: 3687–3691 (1995). G418 and puromycin-resistant MECs will be plated at different cell densities in D2 medium (which allows growth of only the immortal cells) and then the proportion of immortal clones will be assessed. See, e.g., Wazer et al., *Proc Natl Acad Sci USA*, 92: 3687–3691 (1995). Wild-type p53 will be used as a positive control, as it is expected to antagonize the effect of E6. If over-expression of E6TP1 reduces the efficiency of immortalization, as we anticipate, these analyses would provide strong evidence that E6TP1 is a target for E6 whose functional inactivation is important for E6-mediated immortalization. These results will be used to assess the appropriate levels for treatment of HPV associated diseases and carcinomas.

Example 7

Effect of E6TP1 Overexpression on Growth and Tumorigenicity of Established Tumor Cell Lines While our analyses implicate E6TP1 in E6-induced immortalization, it is possible that its tumor suppressor effect may also be exerted at a later stage of oncogenic transformation. For example, while p53 degradation is clearly critical for E6-induced MEC immortalization, p53 is also important in later stages of oncogenic transformation and its overexpression can suppress the tumorigenic phenotype. See, e.g., Baker et al., *Science*, 249: 912–915 (1990) and Baker et al., *Science*, 244: 217–221 (1989). Therefore, to further address the potential tumor suppressor role of E6TP1, we will overexpress E6TP1 in selected breast (MDA-MB-23 1) and cervical ( HeLa, HPV-positive, and C33A, HPV-negative) tumor cell lines and assess its potential to suppress their tumorigenicity by in vitro and in vivo assays. A full-length sense E6TP1 cDNA or anti-sense control, cloned into pCMVneo vector (which works efficiently in mammary and cervical cells) will be transfected into cells by calcium phosphate method, as previously described. See, e.g., Band et al., *Proc Natl Acad Sci USA*, 87: 463–467 (1990). Stably transfected clones will be examined for expression of E6TP1 mRNA and protein. Transfectants over-expressing low, moderate or high levels of E6TP1 protein will be compared with vector and anti-sense-transfected and parental cells for growth and oncogenic behavior (see infra). Wild-type p53 will serve as a control. Control and transfected cells will be compared for rate of growth (measured as population doubling time), growth in low versus high serum, in the presence or absence of exogenous growth factors (such as EGF, insulin), and distribution of cells in different phases of cell cycle (using bromodeoxyuridine and propidium iodide staining in FACS analysis; see, e.g., Keyomarsi et al., *Cancer Res.*, 51: 3602–3609 (1991)). In addition, we will examine the ability of cells to form colonies (clonal growth) which serves as a sensitive index to monitor growth suppression by other genes (e.g., p53). See, e.g., Wazer et al., *Mol Cell Biol*, 14: 2468–2478 (1994). We will also examine the effect of E6TP1-overexpression on anchorage-independent growth, property usually correlates with oncogenic behavior of cells and thus may serve as an indicator of altered oncogenicity of transfectants. See, e.g., Wazer et al., *Mol Cell Biol*, 14: 2468–2478 (1994).

To examine the potential suppressive effect of E6TP1 on tumorigenic potential in vivo, control and E6TP1-transfected tumor cells will be implanted subcutaneously in the mammary gland of Balb/C nude mice. See, e.g., Wazer et al., *Mol Cell Biol*, 14: 2468–2478 (1994). We will then measure the tumor size and rapidity of tumor growth, assess any tumor regression and the ability of tumor cells to be reestablished in culture, as we have done before. See, e.g., Wazer et al., *Mol Cell Biol*, 14: 2468–2478 (1994) and Band et al., *Cancer Res.*, 50: 7351–7357 (1990). To determine the influence of E6TP1 on metastatic growth of transfected cells, we will compare vector-transfected and E6TP1-transfected MDA-MB-231 cells for their ability to form metastatic tumors when injected subcutaneously into nude mice. See, e.g., Price et al., *Cancer Res.*, 50: 747–721 (1990). We will determine the number and size of metastatic lesions in lung and lymph nodes by visual and histopathologic examination. These analyses should reveal if E6TP1 decreases the metastatic potential, as we anticipate.

Since we anticipate E6TP1 to be involved in inhibition of cell growth, this property may prevent establishment of stable transfectants akin to transfection of p53 and Rb tumor suppressor genes.

To examine the growth inhibitory properties of E6TP1 in detail, we will then resort to an inducible expression system. Several such systems are currently available, including the IPTG-inducible Lac-switch system (Stratagene), tetracycline-regulated system (Invitrogen), and the ecdysone-inducible system (Invitrogen). Additional advantages of inducible systems are that the levels and duration of expression can be precisely controlled, and uninduced cells serve as their own controls.

Altogether, the level of reversal of oncogenic phenotype in established tumor cell lines should directly assess the level of tumor suppressor function by E6TP1 in the absence (MDA-MB-231; C33A) or presence (HeLa) of E6.

Example 8

Cellular Effects of Inhibiting E6TP1 Expression

If E6TP1 is involved in a growth suppressive pathway, as we predict, then elimination of its expression may promote growth resulting in extended life span or immortalization of normal MECs either by itself or in conjunction with other oncogenic stimuli. At present, methodologies to specifically inhibit gene expression in primary epithelial cells have not been established. However, expression of antisense mRNA (using 5' cDNA fragment in reverse orientation) or use of antisense oligonucleotides has been shown to inhibit gene expression in selected primary cell types. See, e.g., Melino et al., *Mol Cell Biol*, 14: 6584–6596 (1994) and Kook et al., *EMBO J*, 13: 3983–3991 (1994). Interestingly, antisense inhibition of tuberin expression decreased the proportion of cells in G1 and abolished the entry of cells into $G_0$ upon serum withdrawal. See, e.g., Soucek et al.,*J Biol Chem*, 272: 29301–29308 (1997). We will therefore attempt to express an anti-sense E6TP1 cDNA in normal MECs using retroviral infection. See, e.g., Wazer et al., *Proc Natl Acad Sci USA*, 92: 3687–3691 (1995). In addition, antisense oligonucleotide (e.g., phosphorothioate methyl-phosphonate or O-methylribonucleotide analogs), corresponding to N-terminal region (e.g. first 5 codons) of the mature protein will be introduced into MECs to block mRNA translation. See, e.g., Soucek et al., *J Biol Chem*, 272: 29301–29308 (1997); Kook et al., *EMBO J*, 13: 3983–3991 (1994). Cells infected with antisense retroviral expression vectors or treated with different concentrations (typically micromolar) of oligonucleotides will be examined for expression of E6TP1 mRNA (using an anti-sense strand probe generated by asymmetric PCR or an anti-sense oligonucleotide) and E6TP1 protein (with antibodies). If sufficient inhibition of E6TP1 expression can be achieved, the effect of treatments on cell growth under various conditions will be assessed (see above).

One anticipated consequence of reduced E6TP1 expression may be an inability of cells to undergo growth arrest in response to stimuli such as (-irradiation, as is seen after E6-immortalization. See, e.g., Wazer et al., *Proc Natl Acad Sci USA*, 92: 3687–3691 (1995). Alternatively, cells may show extended life span or proceed to immortality. To explore the latter possibility further, we will simultaneously introduce relatively weakly immortalizing bovine papilloma virus (BPV)-1 or HPV6 E6 genes into anti-sense treated cells to determine if immortalization may be facilitated. See, e.g., Band et al., *EMBO J*, 12: 1847–1852 (1993). Ultimately, however, a more directed approach to ablate E6TP1 function using knock-out technology will be more suitable for definitive assessment of the role of E6TP1.

Example 9

Transgenic Animals

E6TP1 cDNA will be cloned into a general mammalian expression vector such as vector under the control of CMV promoter, or tissue specific promoter such as vector under the control of WAP promoter which is specific for mammary gland. The fragment containing the promoter, the E6TP1 cDNA, and the polyadenylation sequences will be digested out from the plasmid and injected into fertilized eggs. Mice born from these eggs will be screened for the presence of transgene in their genome by southern blotting analysis or PCR of genomic DNA prepared from the tail biopsies.

Knock out mice: The first step to make the knock out mice is to clone the mouse homologous of E6TP1. We have obtained the mouse homologous of E6TP1 gene by screening the mouse strain 129 bac genomic library using E6TP1 cDNA as a probe. We have mapped and partially sequenced the mouse gene to obtain information to construct the knockout vector. Appropriate regions of the E6TP1 mouse gene were cloned into the knockout vector with both positive selectable and negative selectable markers. We then transfected ES cells, selected for transfected clones, amplified the selected ES cell cultures, and prepared genomic DNA from the resulting ES cultures. The successfully targeted clones are being identified by southern blotting or PCR. After identification of successfully targeted ES clones, the positive ES cell clones will be injected into isolated host blastocysts to generate several chimeric animals. The chimeric animals will be bred to screen for animals with germline transmission of the mutant allele by southern blot analysis of tail DNA. Both heterozygous and homozygous mice will be generated by breeding the selected animals.

Example 10

Defining the Function of E6TP1 Structural Domains

Assess the role of the E6-binding Domain in E6TP1 function

Using a series of N- and C-terminal truncations of E6TP1α (FIG. 2), we have demonstrated that the C-terminal 194 amino acids of E6TP1, which include a leucine zipper motif, are sufficient to mediate binding to E6 (FIG. 3). We will perform further in vitro binding studies between GST-E6 and additional truncations of E6TP1 to define the minimal region required for E6-E6TP1 association. Point mutations (e.g. substituting leucines in the zipper with hydrophilic/charged residues) will be used to identify mutants that fail to bind to E6. E6TP1 cDNA constructs incorporating deletion or point mutation of the E6-binding motif will be generated and these will be expressed in normal MECs and tumor cell lines (see Examples 5–7, supra) to assess their tumor suppressor/growth inhibitory function in comparison to wild-type protein. Similar levels of E6TP1 protein expression will be verified by Immunoblotting and/or immunoprecipitation.

If E6 targets a functionally important region in E6TP1, as is common with other viral oncogenes, a deletion or point mutations in this region may result in loss of E6TP1 function. It is also possible that the E6 binding site mediates interaction with endogenous proteins that are needed for the tumor suppressor function of E6TP1, and hence the mutant forms of E6TP1 may gain a growth promoting effect; for example, SV40 T antigen binds to the DNA-binding domain of p53 and mutations in this region abolish SV40 T binding but are dominantly transforming. See, e.g., Levine, *Cell*, 88: 323–331 (1997). If E6-binding region corresponds to the non-zipper part of the C-terminal region, then the leucine zipper will be separately mutated to determine its role in E6TP1 function. If the leucine zipper is functionally important, we will assess if this region may be due to homo- or hetero-dimerization, similar to other leucine zipper motifs. See, e.g., LandSchulz et al., *Science*, 240: 1759–1764 (1988).

Assess the Role of the GAP Domain

Amino acids 489 to 820 of E6TP1 show high homology to the catalytic domains of documented Rap-specific GAPs. Significantly, GAP activity was shown to be essential for the tumor suppressor function of tuberin. See, e.g., Jin et al., *Proc Natl Acad Sci USA*, 93: 9154–9159 (1996). Thus, the GAP domain is likely to be important for E6TP1 function. We will use a mutational approach to assess the role of the GAP domain in tumor suppressor and growth-inhibitory activity of E6TP1. In one approach, the GAP domain (amino acid 489 to 820) will be deleted from E6TP1 using recombinant PCR. The sequences that encode regions N-terminal and C-terminal to the GAP domain will be separately amplified and used in a second PCR reaction to generate a GAP-deleted E6TP1. Confirmed cDNAs will be cloned in pCMV-neo vector for expression. In a second approach mutations will be introduced in selected residues that are highly conserved among Rap-GAP family members (see supra). The GAP domain-mutated or -deleted E6TP1, or wild-type E6TP1, will be introduced into normal MECs and tumor cell lines (as in Examples 5–7, supra), to ascertain the impact of inactivating the GAP domain on E6TP1 function.

One anticipated outcome of these experiments is that GAP mutants will be ineffective as tumor suppressors. However, since other domains of mutant E6TP1 proteins may still interact with cellular proteins that mediate E6TP1 function, the mutant proteins may attain a dominant inhibitory phenotype and produce an effect opposite to that of the wild-type E6TP1. Overall, these analyses should provide a direct insight into the requirement of the GAP domain for E6TP1 function.

Assess the Role of PDZ Domain

A distinctive feature of E6TP1 and its closely related homologue SPA-1 is the presence of a PDZ-domain (amino acid 947–1018) C-terminal to the GAP domain. PDZ domains are independently folding modules found in a large array of signaling and structural proteins that recognize short C-terminal peptide sequences that are typically in transmembrane proteins. As a result, many PDZ domain-containing proteins are targeted to submembranous regions where they participate in a scaffolding or signaling function. See, e.g., Ponting et al., *Bioessays,* 19: 469–479 (1997). We will use deletional and mutational inactivation to assess the role of the PDZ domain in E6TP1 function. Recombinant PCR will be used to generate E6TP1 mutants in which the PDZ domain has been deleted, as proposed above for the GAP domain. In the mutational approach, based on recently demonstrated crystal structures of the third PDZ domains of the hdlg alone and PSD-95 bound to a peptide, we will target the residues that are highly conserved among PDZ domains and are critical for ligand binding. See, e.g., Cabral et al., *Nature,* 386: 649–652 (1996). The F residue (F966 in E6TP1) in the highly conserved GLGF motif (QLGF in E6TP1) is directly involved in ligand binding; as is a highly conserved R (or K) in the presumptive b1 strand (R958 in E6TP1). See, e.g., Cabral et al., ibid. Based on this information, F966 will be mutated to a charged residue (e.g., R or D) and R958 will be changed to an A or D residue. The PDZ-deleted or -mutated E6TP1 will be introduced into normal MECs and tumor cell lines (as in Examples 5–7) to assess the role of the PDZ domain in E6TP1 function.

We anticipate that mutants in which the PDZ domain has been deleted or inactivated will fail to localize to the physiological cellular location and thus will fail to exert a tumor suppressor and/or growth inhibitory function. It is possible that a mutant protein may be mislocalized into a cellular compartment where E6TP1 is not normally localized, and this may create an unexpected phenotype. As point mutations may alter specificity rather than abrogate binding, it is possible that such mutants may interact with non-physiological ligands, mislocalizing the GAP activity. Based on these results, future studies will utilize the modified yeast two hybrid assay, supra, to identify additional cellular polypeptides with which the E6TP1 PDZ domain interacts, as these may represent upstream or downstream elements in the biochemical pathway in which E6TP1 functions.

In the mutational approaches described supra, it is important to note that deletions, and sometime point mutations, may inactivate the function of a protein due to global misfolding. Misfolded proteins are usually degraded and hence if mutants are stably expressed they are relatively unlikely to be misfolded. In addition, the targeted functional domains are known to fold independently, reducing the likelihood of inducing misfolding of other domains. Finally, the use of structural analyses of related polypeptides to select of residues for mutations further minimizes the likelihood of inducing gross misfolding. It is possible that the structural domains of E6TP1, such as the PDZ and leucine zipper, provide regulatory functions and hence mutations or deletions of these domains may result in exaggerated activity of E6TP1.

In summary, the above analyses should help in assessing the contribution of defined structural domains of E6TP1 in its tumor suppressor and/or growth inhibitory function. Other potential functions of the cellular pathways in which E6TP1 participate may emerge in the course of our studies, and the mutants generated herein should provide suitable reagents to analyze E6TP1 in the context of these additional functions. Future analyses of the protein-protein interaction and/or regulatory functions of the functional domains of E6TP1 should help clarify the exact mechanistic basis of its function.

Example 11

Characterizing GAP Activity in E6TP1

We wish to characterize the GAP activity of E6TP1 in order to link it to a specific G-protein biochemical cascade. The E6TP1 structure predicts its specificity as a GAP toward Rap family of G proteins. However, the closely related SPA-1 protein did show some activity toward Ran (later ascribed to use of a partial protein), although its activity toward Rap is substantially more prominent. See, e.g., Kurachi et al., *J Biol Chem,* 272: 28081–28088 (1997); Hattori et al., *Mol Cell Biol,* 15: 552–560 (1995). Spa1 and rap1GAP are both specific for Rap1 and Rap2, but their expression appears to be mutually exclusive. Thus, their function may be determined by their distinct context, depending on cell types and/or states. See e.g., Kurachi et al *J Biol Chem* 272: 28081–28188 (1997). Further studies suggest that, while Spa1 exhibits Rap-specific GAP activity, it has a higher affinity for a different Ras-related GTPase called Rsr 1. See e.g., Nur-e-Kamal, *Int J Biochem Cell Biol* 28: 1241–1247 (1996). Tuberin, another Rap GAP, will also target Rab, which regulates receptor endocytosis. See, e.g., Xiao et at., *J Biol Chem,* 272: 6097–6100 (1997). Thus, it is essential to directly define the target G protein(s) of E6TP1 and to perform in vivo analyses to demonstrate its participation in the predicted G-protein signaling pathway.

Demonstrate the GAP Activity and Specificity of E6TP1 in vitro

The E6TP1 polypeptide shows highest homology to GAP proteins (RapGAP, SPA-1, and tuberin), with demonstrated selectivity towards Rap1. We have obtained a C-terminally His-tagged human SPA-1 CDNA that is available in the art. E6TP1 cDNA will be similarly tagged (using PCR). Both cDNAs will be cloned into baculovirus expression vector (pBacPAK9) for high level expression in insect cells and affinity purified on nickel-agarose. Purification will be monitored by anti-SPA-1 (available in the art) and anti-E6TP1 (see supra) immunoblotting and Coomassie blue staining. Purified proteins will be used for GAP assays (see infra). We have previously used this approach to purify an enzymatically-active serine protease NESI (see, e.g., Liu et al., In: Antibodies. A Laboratory Manual. Cold Spring Harbor Laboratory (1988)), and baculovirus-purified GAP proteins have been used for functional studies by others. See, e.g., Kurachi et al., *J Biol Chem,* 272: 28081–28088 (1997). A number of potential target G-proteins, including Rap1A, Rapb1B, Rap2A, Ran, Rab5, RhoA, cdc42, Rac, K-Ras, H-Ras, and N-Ras, have also been obtained as GST-fusion proteins. The GST-fusion proteins will be purified on glutathione-sepharose beads for GAP assays.

To determine the GAP activity of E6TP1, we will assess its ability, in comparison to SPA-1, to stimulate the GTPase activity of various $^{32}$P-GTP-loaded G-protein. Said GTP loading is performed by incubating the GST-G protein (typically 5 μg in 20 μl reaction) with 5 nM [γ-$^{32}$P] GTP in exchange buffer (50 mM Tris-HCl, pH 7.5, 2.5 mM EDTA, 1 mM DTT, 0.5 mg/ml BSA) for 10–30 minutes at room temp or 30° C., depending on the G-protein. Aliquots of the [γ-$^{32}$P] GTP-loaded G proteins are then incubated in exchange buffer containing 15 mM MgCl$_2$ with various amounts of purified GAP proteins (usually ng to μg) or buffer control. The samples are incubated for various time periods (typically minutes) and radioactive GTP remaining on G-proteins is assessed by immobilizing it by vacuum filtration onto NC45 nitrocellulose membrane filter. The decrease in counts relative to buffer control (without GAP protein) provides a measure of GTP hydrolysis (GAP activity).

While we anticipate that, similar to SPA-1, E6TP1 will exhibit a Rap-specific GAP activity, inclusion of a wide array of G-proteins should ensure that the relative specificity of this effect can be determined. While the use of an intact polypeptide for determination of GAP activity is designed to maintain a physiological context, it is possible that the GAP domain is regulated by other regions of the protein and the whole protein may not exhibit significant activity in vitro. Although this scenario is unlikely (via comparison with SPA-1), it may be necessary to express the GAP domain by itself in order to demonstrate the GAP activity. See, e.g., Kurachi et al., *J Biol Chem*, 272: 28081–28088 (1997). Further studies can then be directed toward elucidating the regulatory role of other domains for GAP activity of E6TP1. If GAP activity of E6TP1 toward Rap and/or other G-proteins can be demonstrated in vitro, as we anticipate, we will mutate selective residues in the GAP domain to derive GAP-deficient mutants suitable for functional analyses (as previously described, supra).

While the determined structures of Ras- and Rho-specific GAP domains have revealed a critical role of certain residues for GAP activity, at present the structure of Rap-specific GAP domains has not been determined. See, e.g., Au et al., *Am J Hum Genet*, 62: 286–294 (1998). Therefore, mutations will be introduced in conserved residues found to be mutated in tuberin in tuberous sclerosis patients (Y617C, corresponding to tuberin mutation Y1526C or highly conserved sequence boxes (e.g., KRH 704–706→DDD; GND 708–710→AAA; RTR 808–810→AAA). See, e.g., Au et al., *Am J Hum Genet*, 62: 286–294 (1998). The mutations will be generated by site-directed mutagenesis using the Altered-Sites system (Promega) and mutants will be expressed in baculovirus. Purified wild-type and mutant E6TP1 proteins will be compared for GAP activity. We anticipate that this approach will yield mutants with a selective loss of GAP activity, which will provide reagents for in vivo functional assays.

Impact of E6TP1 on the in vivo Function of its Target G Proteins

The studies above are designed to establish the GAP activity of E6TP1 towards Rap (or other) small G-proteins. Here, we wish to explore the role of E6TP1 as a regulator of the Rap G-protein signaling in vivo.

Identification of Rap1 during a screen for reversion of activated K-ras transformation, along with the ability of Rap1 to bind to Ras effectors (e.g, Raf and Ras GAP) without functional effects, led to suggestions that Rap G-proteins antagonize Ras function. See, e.g., Kitayama et al., *Cell*, 56: 77–84 (1989); Sprang, *Annu Rev Biochem*, 66: 639–678 (1997); Feig, *Curr Opin Cell Biol*, 6: 204–211 (1994); Polakis and McCormick, *Cancer Surveys*, 12: 25–42 (1992); Polakis and McCormick, *J Biol Chem*, 268: 9157–9160(1993). On the other hand, a substantial amount of recent literature suggests that Rap proteins initiate a distinct signaling pathway that positively regulates cell growth or differentiation: i.e., microinjection of GTP-loaded Rap into Swiss 3T3 cells induced DNA synthesis (see, e.g., Yoshida et al., *Mol Cell Biol*, 12: 3407–3414 (1992)); Rap proteins positively contribute toward activation of the NADPH oxidase system in phagocytic cells (see, e.g., Abo et al., *Nature*, 353: 668–670 (1991)); and Rap1 specifically activates B-Raf leading to Ras-independent late phase MAP kinase activation linked to differentiation of PC-12 cells. See, e.g., Vossler et al., *Cell*, 89: 73–82 (1997). GTP loading of Rap1 is seen upon thrombin activation of platelets and anti-CD3 stimulation of T lymphocytes (see, e.g., Reedquist and Bos, *J Biol Chem*, 9: 4944–4949 (1998)); and overexpression of C3G, a Rap-specific GEF, leads to increased JNK activity in 293T cells. See, e.g., Tanaka and Hanafusa, *J Biol Chem*, 273: 1281–1284 (1998). These more recent studies lead us to propose that Rap G protein activation initiates a positive signal in epithelial cells and that this signal is negatively regulated by E6TP1. Alternatively, if Rap proteins initiate an inhibitory signal in epithelial cells (e.g., via Ras-antagonism), E6TP1 may participate in this pathway as a Rap effector, similar to the proposed role of RasGAP downstream of Ras. See, e.g., Background Section. We will begin to address the role of E6TP1 in Rap signaling and to investigate the mechanism of its action. The exploratory nature of these experiments needs to be emphasized given the controversy in the Rap G-protein signaling field and lack of a clear paradigm. Perhaps, Rap pathway participates in distinct functions in distinct cells, resulting in the apparently contradictory findings in the literature.

In an effort to discern if E6TP1 is a negative regulator via GAP activity toward Rap-GAP or a positive regulator (by serving as an effector) of Rap function, we will use the well-studied PC12 neuroblastoma model. E6TP1 or a GAP-inactive mutant of E6TP1 will be transiently or stably expressed in PC12 cells. The transfectants will be stimulated with NGF and the sustained phase MAP kinase activity in response to NGF will be monitored by immunoblotting with phospho-MAPK-specific antibodies (New England Biolabs) or by in vitro kinase analysis of anti-MAPK immunoprecipitants on GST-Elk. See, e.g., York et al., *Nature*, 392: 622–626 (1998). Further experiments will be directed at determining if the effect of E6TP1 is dependent on its GAP activity (using GAP mutants) toward Rap1 (assaying GTP-loading of Rap1). Based on these results, further analyses will be initiated to analyze the role of E6TP1 in Rap G-protein signaling cascade in epithelial cells. However, since the role of this pathway in MECs is at present unknown, potential experimental approaches will include analyses of the Rap pathway downstream of the EGF-receptor or other growth factor-initiated pathways. For example, we will first need to determine if these cells express B-raf and Rap proteins, although these have been reported to be widely expressed. If E6TP1 is shown to be a regulator of Rap GTPase in MECs, we will assess the effect of expressing the activated Rap (RapV12), which may be anticipated to increase downstream effects (e.g. MAP kinase activity), or a dominant-negative Rap (RapN17), which may have an opposite effect. Similarly, the effect of E6TP1 (or its mutants) can be assessed by co-expressing said E6TP1 or E6TP1 mutants with Rap G-proteins. If these initial experiments implicate E6TP1 in a Rap signaling pathway, future directions will be to identify specific downstream targets of said Rap G-protein signaling pathway in epithelial cells, as well as upstream events that lead to RapGTP loading.

Overall, the studies described herein are designed to gain an insight into the specific biochemical signaling pathway(s) regulated by E6TP1 based on its GAP activity.

EQUIVALENTS

From the foregoing detailed description of the specific embodiments of the invention, it should be apparent that a novel Human Papilloma Virus (HPV) E6-targeted protein ("E6TP1") for control of cell growth and/or suppression and its use as a Therapeutic in carcinomas and HPV-associated diseases have been described. Although particular embodiments have been disclosed herein in detail, this has been done by way of example for purposes of illustration only, and is not intended to be limiting with respect to the scope of the appended claims which follow. In particular, it is contemplated by the inventors that various substitutions, alterations, and modifications may be made to the invention without departing from the spirit and scope of the invention as defined by the claims. For instance, the choice of E6TP1 product, expression construct, or disease type (e.g., HPV-infected cells, HPV-associated carcinomas, or other tissues or neoplasms) is believed to be a matter of routine for a person of ordinary skill in the art with knowledge of the embodiments described herein.

What is claimed is:

1. An isolated nucleic acid encoding a human E6TP1 isoform, wherein said isoform binds to human papillomavirus E6 protein and comprises amino acids 489–819 of SEQ ID NO:2.

2. The nucleic acid of claim 1, wherein said nucleic acid comprises the sequence shown in SEQ ID NO:1 or the complement thereof.

3. The nucleic acid of claim 1, wherein said nucleic acid comprises the sequence shown in SEQ ID NO:3 or the complement thereof.

4. A method of producing an isolated E6TP1 protein comprising:
   a) culturing a host cell transformed with an expression vector comprising the nucleic acid of claim 1;
   b) expressing said nucleic acid to produce an E6TP1 protein, and
   c) recovering said E6TP1 protein.

5. The nucleic acid of claim 1, wherein said isoform further comprises amino acids 947–1018 of SEQ ID NO:2.

6. The nucleic acid of claim 1, wherein said isoform further comprises amino acids 1705–1779 of SEQ ID NO:2.

7. The nucleic acid of claim 1, wherein said isoform further comprises amino acids 1726–1790 of SEQ ID NO:4.

8. The nucleic acid of claim 1, wherein said isoform further comprises the amino acid sequence of SEQ ID NO:13.

9. The nucleic acid of claim 1, wherein said isoform comprises the amino acid sequence of SEQ ID NO:2.

10. The nucleic acid of claim 1, wherein said isoform comprises the amino acid sequence of SEQ ID NO:4.

11. The nucleic acid of claim 1, wherein the sequence of said nucleic acid comprises the coding region of SEQ ID NO:1.

12. The nucleic acid of claim 1, wherein the sequence of said nucleic acid comprises the coding region of SEQ ID NO:3.

13. The nucleic acid of claim 1, wherein the sequence of said nucleic acid comprises nucleotides 1813–2805 of SEQ ID NO:1.

14. The nucleic acid of claim 1, wherein the sequence of said nucleic acid comprises nucleotides 3187–3403 of SEQ ID NO:1.

15. The nucleic acid of claim 1, wherein the sequence of said nucleic acid comprises nucleotides 5461–5685 of SEQ ID NO:1.

16. The nucleic acid of claim 1, wherein the sequence of said nucleic acid comprises nuclcotides 5524–5718 of SEQ ID NO:3.

17. The nucleic acid of claim 1, wherein said nucleic acid further comprises a transcriptional promoter, a transcription terminator, an origin of replication, a selectable marker, a transcription enhancer element, a transcription repressor element, or an artificial splice site.

18. A host cell transformed with an expression vector, wherein said expression vector encodes an E6TP1 polypeptide comprising amino acids 489–819 of SEQ ID NO:2.

19. A host cell transformed with an expression vector, wherein said expression vector encodes an E6TP1 polypeptide comprising the amino acid sequence of SEQ ID NO:2 or SEQ ID NO:4.

* * * * *

SEQUENCE LISTING

```
<160> NUMBER OF SEQ ID NOS: 17

<210> SEQ ID NO 1
<211> LENGTH: 5965
<212> TYPE: DNA
<213> ORGANISM: Homo sapiens
<220> FEATURE:
<221> NAME/KEY: CDS
<222> LOCATION: (349)..(5697)

<400> SEQUENCE: 1
ggtgtggacg ttgtctaaat ttcggtagcc atggcacaag aatataagaa agcatgggat      60
tatggcaacc acagaatctc agtagtacaa gttccattca gttttttctg aaagaaagcc     120
ctctgttaaa gtgaagcaaa gaaactgttg tggattataa cgtttagaag ttccaatttt     180
tcagtgcttt acaaataaag catcatttaa ccttttaaat gaaaaagatt aagatctcat     240
gcaactgttg tattttctgg aagccattct ccaaaaggga agtgcacatt taaaacacag     300
atatgatggt ccttgctgca gggatttaag tctacttgct tttacatc atg acc agc      357
                                                      Met Thr Ser
                                                        1 ttg aaa cgg tca cag aca gaa agg cct ctt gcc act gac agg gcc tct      405
Leu Lys Arg Ser Gln Thr Glu Arg Pro Leu Ala Thr Asp Arg Ala Ser
       5                  10                  15 gtt gtt ggc aca gac ggc acc ccc aaa gtc cac act gat gat ttc tac      453
Val Val Gly Thr Asp Gly Thr Pro Lys Val His Thr Asp Asp Phe Tyr
 20                  25                  30                  35 atg cgg cgc ttc cgg tcc caa aat ggc agc tta gga tca tca gtt atg      501
Met Arg Arg Phe Arg Ser Gln Asn Gly Ser Leu Gly Ser Ser Val Met
                 40                  45                  50 gct cct gta gga ccc ccc cga agt gaa ggt tct cac cat ata acc tca      549
Ala Pro Val Gly Pro Pro Arg Ser Glu Gly Ser His His Ile Thr Ser
             55                  60                  65 acc ccc gga gtc cca aaa atg ggg gta agg gca agg att gca gat tgg      597
Thr Pro Gly Val Pro Lys Met Gly Val Arg Ala Arg Ile Ala Asp Trp
         70                  75                  80 ccc cca aga aag gaa aac ata aaa gaa tct agc cgt tca agc cag gaa      645
Pro Pro Arg Lys Glu Asn Ile Lys Glu Ser Ser Arg Ser Ser Gln Glu
     85                  90                  95 ata gaa acc tca agt tgc ctt gat agc ctg tcc tcc aaa agc agt cct      693
Ile Glu Thr Ser Ser Cys Leu Asp Ser Leu Ser Ser Lys Ser Ser Pro
100                 105                 110                 115 gtg agt cag gga agt tct gtt agc ctc aat tcc aat gac tca gcc atg      741
Val Ser Gln Gly Ser Ser Val Ser Leu Asn Ser Asn Asp Ser Ala Met
                120                 125                 130
```

-continued

| | | | | | | | | | | | | | | | | |
|---|---|---|---|---|---|---|---|---|---|---|---|---|---|---|---|---|
| ctg | aaa | agc | ata | cag | aac | acg | ctg | aaa | aac | aag | aca | aga | ccg | tcg | gag | 789 |
| Leu | Lys | Ser | Ile | Gln | Asn | Thr | Leu | Lys | Asn | Lys | Thr | Arg | Pro | Ser | Glu | |
| | | | 135 | | | | 140 | | | | | 145 | | | | |
| aac | atg | gac | tcc | aga | ttt | ctc | atg | cct | gaa | gcc | tac | ccc | agc | tcc | ccc | 837 |
| Asn | Met | Asp | Ser | Arg | Phe | Leu | Met | Pro | Glu | Ala | Tyr | Pro | Ser | Ser | Pro | |
| | | 150 | | | | | 155 | | | | | 160 | | | | |
| aga | aaa | gct | ctt | cgc | aga | ata | cgc | cag | cga | agc | aac | agt | gat | atc | acc | 885 |
| Arg | Lys | Ala | Leu | Arg | Arg | Ile | Arg | Gln | Arg | Ser | Asn | Ser | Asp | Ile | Thr | |
| | 165 | | | | | 170 | | | | | 175 | | | | | |
| ata | agt | gaa | ctt | gat | gtg | gat | agc | ttt | gat | gaa | tgt | atc | tca | cct | aca | 933 |
| Ile | Ser | Glu | Leu | Asp | Val | Asp | Ser | Phe | Asp | Glu | Cys | Ile | Ser | Pro | Thr | |
| 180 | | | | | 185 | | | | | 190 | | | | | 195 | |
| tac | aag | act | gga | cca | tca | ctg | cac | agg | gaa | tat | ggt | agc | aca | tct | tca | 981 |
| Tyr | Lys | Thr | Gly | Pro | Ser | Leu | His | Arg | Glu | Tyr | Gly | Ser | Thr | Ser | Ser | |
| | | | | 200 | | | | | 205 | | | | | 210 | | |
| att | gat | aaa | cag | gga | aca | tct | gga | gaa | agc | ttt | ttt | gat | ttg | tta | aag | 1029 |
| Ile | Asp | Lys | Gln | Gly | Thr | Ser | Gly | Glu | Ser | Phe | Phe | Asp | Leu | Leu | Lys | |
| | | | | 215 | | | | | 220 | | | | | 225 | | |
| ggc | tac | aaa | gat | gac | aaa | tct | gat | cga | ggt | cca | act | cca | acc | aag | ctc | 1077 |
| Gly | Tyr | Lys | Asp | Asp | Lys | Ser | Asp | Arg | Gly | Pro | Thr | Pro | Thr | Lys | Leu | |
| | | 230 | | | | | 235 | | | | | 240 | | | | |
| agt | gac | ttt | ctc | att | act | ggt | ggt | ggc | aag | ggt | tct | ggt | ttc | tct | ttg | 1125 |
| Ser | Asp | Phe | Leu | Ile | Thr | Gly | Gly | Gly | Lys | Gly | Ser | Gly | Phe | Ser | Leu | |
| | 245 | | | | | 250 | | | | | 255 | | | | | |
| gat | gta | ata | gac | ggg | cct | atc | tca | cag | aga | gag | aac | ctc | agg | ctt | ttt | 1173 |
| Asp | Val | Ile | Asp | Gly | Pro | Ile | Ser | Gln | Arg | Glu | Asn | Leu | Arg | Leu | Phe | |
| 260 | | | | | 265 | | | | | 270 | | | | | 275 | |
| aag | gaa | agg | gaa | aaa | cca | ctc | aag | cga | cgt | tca | aaa | tct | gaa | act | gga | 1221 |
| Lys | Glu | Arg | Glu | Lys | Pro | Leu | Lys | Arg | Arg | Ser | Lys | Ser | Glu | Thr | Gly | |
| | | | | 280 | | | | | 285 | | | | | 290 | | |
| gac | tcc | tct | att | ttt | cgt | aaa | ttg | cgc | aat | gcc | aaa | ggt | gaa | gaa | ctt | 1269 |
| Asp | Ser | Ser | Ile | Phe | Arg | Lys | Leu | Arg | Asn | Ala | Lys | Gly | Glu | Glu | Leu | |
| | | | 295 | | | | | 300 | | | | | 305 | | | |
| ggg | aag | tca | tca | gat | ctt | gaa | gat | aac | cga | tca | gaa | gac | tct | gtc | agg | 1317 |
| Gly | Lys | Ser | Ser | Asp | Leu | Glu | Asp | Asn | Arg | Ser | Glu | Asp | Ser | Val | Arg | |
| | | 310 | | | | | 315 | | | | | 320 | | | | |
| ccc | tgg | aca | tgt | cca | aag | tgc | ttt | gcc | cac | tat | gat | gtc | cag | agt | ata | 1365 |
| Pro | Trp | Thr | Cys | Pro | Lys | Cys | Phe | Ala | His | Tyr | Asp | Val | Gln | Ser | Ile | |
| | 325 | | | | | 330 | | | | | 335 | | | | | |
| tta | ttt | gat | ttg | aat | gag | gca | att | atg | aac | agg | cac | aat | gtt | att | aag | 1413 |
| Leu | Phe | Asp | Leu | Asn | Glu | Ala | Ile | Met | Asn | Arg | His | Asn | Val | Ile | Lys | |
| 340 | | | | | 345 | | | | | 350 | | | | | 355 | |
| agg | aga | aac | acc | acc | act | gga | gct | tcc | gca | gct | gcc | gtg | gca | tcc | ttg | 1461 |
| Arg | Arg | Asn | Thr | Thr | Thr | Gly | Ala | Ser | Ala | Ala | Ala | Val | Ala | Ser | Leu | |
| | | | | 360 | | | | | 365 | | | | | 370 | | |
| gtc | tct | gga | cct | ctg | tct | cat | tca | gcc | agt | ttt | agc | tcc | cca | atg | ggc | 1509 |
| Val | Ser | Gly | Pro | Leu | Ser | His | Ser | Ala | Ser | Phe | Ser | Ser | Pro | Met | Gly | |
| | | | 375 | | | | | 380 | | | | | 385 | | | |
| agc | aca | gag | gac | ctg | aat | tcc | aaa | gga | agc | ctc | agc | atg | gac | cag | gga | 1557 |
| Ser | Thr | Glu | Asp | Leu | Asn | Ser | Lys | Gly | Ser | Leu | Ser | Met | Asp | Gln | Gly | |
| | | 390 | | | | | 395 | | | | | 400 | | | | |
| gat | gat | aaa | agc | aat | gag | ctt | gta | atg | agc | tgt | cca | tat | ttt | cgg | aat | 1605 |
| Asp | Asp | Lys | Ser | Asn | Glu | Leu | Val | Met | Ser | Cys | Pro | Tyr | Phe | Arg | Asn | |
| | 405 | | | | | 410 | | | | | 415 | | | | | |
| gag | ata | ggt | gga | gaa | ggg | gag | agg | aaa | atc | agc | ctt | tca | aaa | tca | aat | 1653 |
| Glu | Ile | Gly | Gly | Glu | Gly | Glu | Arg | Lys | Ile | Ser | Leu | Ser | Lys | Ser | Asn | |
| 420 | | | | | 425 | | | | | 430 | | | | | 435 | |
| tct | ggc | tcc | ttt | agt | gga | tgt | gaa | agt | gcc | tcc | ttt | gag | tct | acc | ctt | 1701 |
| Ser | Gly | Ser | Phe | Ser | Gly | Cys | Glu | Ser | Ala | Ser | Phe | Glu | Ser | Thr | Leu | |
| | | | | 440 | | | | | 445 | | | | | 450 | | |

```
agt tcc cat tgc aca aat gca gga gtg gca gta ctt gaa gtg ccc aag    1749
Ser Ser His Cys Thr Asn Ala Gly Val Ala Val Leu Glu Val Pro Lys
            455                 460                 465 gag aac ttg gtg ttg cac cta gat aga gtg aaa aga tac atc gtg gaa    1797
Glu Asn Leu Val Leu His Leu Asp Arg Val Lys Arg Tyr Ile Val Glu
470                 475                 480 cac gta gat ctg ggt gca tac tat tat aga aaa ttt ttc tac cag aag    1845
His Val Asp Leu Gly Ala Tyr Tyr Tyr Arg Lys Phe Phe Tyr Gln Lys
        485                 490                 495 gaa cac tgg aac tat ttt ggg gct gat gag aat ctt ggt cca gtg gct    1893
Glu His Trp Asn Tyr Phe Gly Ala Asp Glu Asn Leu Gly Pro Val Ala
500                 505                 510                 515 gtg agc att cga agg gaa aaa cca gat gaa atg aaa gaa aat gga tct    1941
Val Ser Ile Arg Arg Glu Lys Pro Asp Glu Met Lys Glu Asn Gly Ser
            520                 525                 530 ccg tac aac tac cga ata att ttt aga act agt gag ctc atg aca ctg    1989
Pro Tyr Asn Tyr Arg Ile Ile Phe Arg Thr Ser Glu Leu Met Thr Leu
                535                 540                 545 aga ggt tcg gtc ctg gag gac gcc att ccg tcg aca gcc aag cac tcg    2037
Arg Gly Ser Val Leu Glu Asp Ala Ile Pro Ser Thr Ala Lys His Ser
        550                 555                 560 aca gcc aga ggc ctg cct ctc aaa gaa gtg ctg gag cac gtg gtt cct    2085
Thr Ala Arg Gly Leu Pro Leu Lys Glu Val Leu Glu His Val Val Pro
565                 570                 575 gag ctc aat gtc cag tgc ctg cgg ttg gcc ttc aac aca ccc aag gtc    2133
Glu Leu Asn Val Gln Cys Leu Arg Leu Ala Phe Asn Thr Pro Lys Val
            580                 585                 590         595 aca gag cag ctc atg aaa ctg gat gaa caa ggg ctg aac tac cag cag    2181
Thr Glu Gln Leu Met Lys Leu Asp Glu Gln Gly Leu Asn Tyr Gln Gln
                600                 605                 610 aaa gta ggc atc atg tac tgc aaa gct gga cag agc act gaa gaa gag    2229
Lys Val Gly Ile Met Tyr Cys Lys Ala Gly Gln Ser Thr Glu Glu Glu
        615                 620                 625 atg tac aac aat gag tca gct ggc cca gcc ttt gaa gaa ttc ctt caa    2277
Met Tyr Asn Asn Glu Ser Ala Gly Pro Ala Phe Glu Glu Phe Leu Gln
630                 635                 640 cta ttg gga gag cga gtt cgg ctc aaa gga ttt gag aag tat cga gca    2325
Leu Leu Gly Glu Arg Val Arg Leu Lys Gly Phe Glu Lys Tyr Arg Ala
            645                 650                 655 cag ctt gat acc aaa act gac tcc act gga acc cat tct ctg tac aca    2373
Gln Leu Asp Thr Lys Thr Asp Ser Thr Gly Thr His Ser Leu Tyr Thr
660                 665                 670                 675 aca tac aaa gat tat gaa att atg ttc cat gtt tct acc atg ctg cca    2421
Thr Tyr Lys Asp Tyr Glu Ile Met Phe His Val Ser Thr Met Leu Pro
            680                 685                 690 tac aca ccc aac aac aaa caa cag ctc ctg agg aag cgg cac att gga    2469
Tyr Thr Pro Asn Asn Lys Gln Gln Leu Leu Arg Lys Arg His Ile Gly
                695                 700                 705 aat gat atc gta aca att gtt ttc caa gag cct gga gca cag cca ttc    2517
Asn Asp Ile Val Thr Ile Val Phe Gln Glu Pro Gly Ala Gln Pro Phe
        710                 715                 720 agc cca aaa aac atc cga tcc cac ttc cag cac gtt ttc gtc atc gtc    2565
Ser Pro Lys Asn Ile Arg Ser His Phe Gln His Val Phe Val Ile Val
725                 730                 735 agg gtg cac aat ccg tgc tct gac agt gtc tgt tat agt gtg gct gtt    2613
Arg Val His Asn Pro Cys Ser Asp Ser Val Cys Tyr Ser Val Ala Val
740                 745                 750                 755 acc agg tcc aga gat gtg cct tcc ttt ggg cct ccc att cct aaa ggg    2661
Thr Arg Ser Arg Asp Val Pro Ser Phe Gly Pro Pro Ile Pro Lys Gly
```

-continued

|  |  |
|---|---|
| gtc act ttc cct aag tca aat gtg ttc agg gac ttc ctt ttg gcg aaa<br>Val Thr Phe Pro Lys Ser Asn Val Phe Arg Asp Phe Leu Leu Ala Lys<br>            775                  780                  785 | 2709 |
| gtg att aat gca gaa aat gct gct cat aaa tcg gag aag ttt cgg gcc<br>Val Ile Asn Ala Glu Asn Ala Ala His Lys Ser Glu Lys Phe Arg Ala<br>      790                  795                  800 | 2757 |
| atg gca act cgg acc cgc cag gaa tac ctg aaa gat ctg gca gaa aag<br>Met Ala Thr Arg Thr Arg Gln Glu Tyr Leu Lys Asp Leu Ala Glu Lys<br>805                  810                  815 | 2805 |
| aat gtc acc aac acc cct atc gac cct tct ggc aag ttt ccg ttc atc<br>Asn Val Thr Asn Thr Pro Ile Asp Pro Ser Gly Lys Phe Pro Phe Ile<br>820                  825                  830                  835 | 2853 |
| tct ctg gct tcc aag aag aag gaa aag tct aag cca tat cca gga gcc<br>Ser Leu Ala Ser Lys Lys Lys Glu Lys Ser Lys Pro Tyr Pro Gly Ala<br>            840                  845                  850 | 2901 |
| gag ctc agc agc atg ggg gcc att gta tgg gca gtc cgg gct gaa gac<br>Glu Leu Ser Ser Met Gly Ala Ile Val Trp Ala Val Arg Ala Glu Asp<br>                855                  860                  865 | 2949 |
| tac aac aag gcc atg gaa cta gac tgc ctt tta ggg atc tcc aat gag<br>Tyr Asn Lys Ala Met Glu Leu Asp Cys Leu Leu Gly Ile Ser Asn Glu<br>      870                  875                  880 | 2997 |
| ttc att gtg ctc att gaa cag gaa aca aag agc gtg gtc ttc aat tgt<br>Phe Ile Val Leu Ile Glu Gln Glu Thr Lys Ser Val Val Phe Asn Cys<br>885                  890                  895 | 3045 |
| tcc tgt aga gat gtg ata ggg tgg act tca act gac acc agc ctc aaa<br>Ser Cys Arg Asp Val Ile Gly Trp Thr Ser Thr Asp Thr Ser Leu Lys<br>900                  905                  910                  915 | 3093 |
| atc ttc tat gaa cga gga gaa tgt gtt tca gtg ggt agt ttt att aac<br>Ile Phe Tyr Glu Arg Gly Glu Cys Val Ser Val Gly Ser Phe Ile Asn<br>            920                  925                  930 | 3141 |
| att gag gag atc aaa gag att gtc aaa agg ttg cag ttt gtt tca aaa<br>Ile Glu Glu Ile Lys Glu Ile Val Lys Arg Leu Gln Phe Val Ser Lys<br>              935                  940                  945 | 3189 |
| ggc tgt gaa tcg gtg gag atg act ctg cga aga aat ggg cta gga cag<br>Gly Cys Glu Ser Val Glu Met Thr Leu Arg Arg Asn Gly Leu Gly Gln<br>      950                  955                  960 | 3237 |
| ctt ggc ttc cat gtc aac tat gag ggc att gtg gcg gat gtg gag ccc<br>Leu Gly Phe His Val Asn Tyr Glu Gly Ile Val Ala Asp Val Glu Pro<br>965                  970                  975 | 3285 |
| tac ggt tat gcc tgg cag gca ggg ctg agg cag ggc agt cgc ctg gtg<br>Tyr Gly Tyr Ala Trp Gln Ala Gly Leu Arg Gln Gly Ser Arg Leu Val<br>980                  985                  990                  995 | 3333 |
| gag atc tgc aag gtg gcg gta gcc act ctg agc cat gag cag atg atc<br>Glu Ile Cys Lys Val Ala Val Ala Thr Leu Ser His Glu Gln Met Ile<br>            1000                  1005                  1010 | 3381 |
| gac ctc ctg aga aca tct gtc acg gtg aag gtt gtc atc att ccc ccg<br>Asp Leu Leu Arg Thr Ser Val Thr Val Lys Val Val Ile Ile Pro Pro<br>              1015                  1020                  1025 | 3429 |
| cat gat gac tgc acc ccg cgg agg agt tgc tct gaa acc tac cgc atg<br>His Asp Asp Cys Thr Pro Arg Arg Ser Cys Ser Glu Thr Tyr Arg Met<br>1030                  1035                  1040 | 3477 |
| cca gtg atg gag tac aaa atg aat gaa ggt gtt tca tac gaa ttc aag<br>Pro Val Met Glu Tyr Lys Met Asn Glu Gly Val Ser Tyr Glu Phe Lys<br>            1045                  1050                  1055 | 3525 |
| ttt ccc ttc cga aat aat aac aag tgg cag agg aac gcc agc aag ggg<br>Phe Pro Phe Arg Asn Asn Asn Lys Trp Gln Arg Asn Ala Ser Lys Gly<br>1060                  1065                  1070                  1075 | 3573 |
| cct cat tca cct caa gtc ccg tcc cag gtg cag agt ccc atg acc tcg | 3621 |

-continued

```
Pro His Ser Pro Gln Val Pro Ser Gln Val Gln Ser Pro Met Thr Ser
            1080                1085                1090 cgg ctg aat gct gga aaa gga gat ggg aag atg cct cct cca gaa aga    3669
Arg Leu Asn Ala Gly Lys Gly Asp Gly Lys Met Pro Pro Pro Glu Arg
        1095                1100                1105 gcc gcc aac atc cct cga agc atc tcc agt gac ggg cgc cca cta gag    3717
Ala Ala Asn Ile Pro Arg Ser Ile Ser Ser Asp Gly Arg Pro Leu Glu
    1110                1115                1120 agg cgg ctg tct cct ggt tcg gac atc tat gtg acg gtc tca tcc atg    3765
Arg Arg Leu Ser Pro Gly Ser Asp Ile Tyr Val Thr Val Ser Ser Met
1125                1130                1135 gct tta gca aga tcc cag tgt cgg aac tct cct agc aac ttg tct tca    3813
Ala Leu Ala Arg Ser Gln Cys Arg Asn Ser Pro Ser Asn Leu Ser Ser
1140                1145                1150                1155 tcc agt gat act ggt tct gtg ggg ggc act tac agg cag aag tcc atg    3861
Ser Ser Asp Thr Gly Ser Val Gly Gly Thr Tyr Arg Gln Lys Ser Met
        1160                1165                1170 ccc gaa ggg ttt gga gtg agc cgt aga tcc cca gcc tcc att gac agg    3909
Pro Glu Gly Phe Gly Val Ser Arg Arg Ser Pro Ala Ser Ile Asp Arg
            1175                1180                1185 cag aac acc cag tca gat att ggt ggc agc gga aaa tcc acg cct agc    3957
Gln Asn Thr Gln Ser Asp Ile Gly Gly Ser Gly Lys Ser Thr Pro Ser
        1190                1195                1200 tgg caa aga agt gag gat agc att gct gac cag atg gag cca aca tgc    4005
Trp Gln Arg Ser Glu Asp Ser Ile Ala Asp Gln Met Glu Pro Thr Cys
        1205                1210                1215 cat ctc cca gca gta tca aag gta ctg cca gct ttc cga gag agc ccc    4053
His Leu Pro Ala Val Ser Lys Val Leu Pro Ala Phe Arg Glu Ser Pro
1220                1225                1230                1235 agt ggg aga tta atg cgg cag gat cca gtg gtt cat ttg tct cca aac    4101
Ser Gly Arg Leu Met Arg Gln Asp Pro Val Val His Leu Ser Pro Asn
        1240                1245                1250 aaa caa ggg cat tct gat agc cac tac tcg agc cac tcc agt agc aat    4149
Lys Gln Gly His Ser Asp Ser His Tyr Ser Ser His Ser Ser Ser Asn
        1255                1260                1265 act ctc tcc agc aat gcg tca agt gcc cat agt gat gag aag tgg tac    4197
Thr Leu Ser Ser Asn Ala Ser Ser Ala His Ser Asp Glu Lys Trp Tyr
        1270                1275                1280 gat ggg gac cgc aca gaa tcc gaa ctc aac agc tat aac tat ctg caa    4245
Asp Gly Asp Arg Thr Glu Ser Glu Leu Asn Ser Tyr Asn Tyr Leu Gln
    1285                1290                1295 ggc acc tct gct gac agt ggc att gac acc acc tct tat ggc ccc agc    4293
Gly Thr Ser Ala Asp Ser Gly Ile Asp Thr Thr Ser Tyr Gly Pro Ser
1300                1305                1310                1315 cac ggc agc aca gcc tcg ctg ggg gct gcc aca tcg tca cct cgc tca    4341
His Gly Ser Thr Ala Ser Leu Gly Ala Ala Thr Ser Ser Pro Arg Ser
        1320                1325                1330 ggg cca ggc aag gag aaa gtg gca ccc cta tgg cac agc tcc agt gaa    4389
Gly Pro Gly Lys Glu Lys Val Ala Pro Leu Trp His Ser Ser Ser Glu
        1335                1340                1345 gta atc tcc atg gca gat cgg act ttg gag aca gag agc cac ggc ctg    4437
Val Ile Ser Met Ala Asp Arg Thr Leu Glu Thr Glu Ser His Gly Leu
        1350                1355                1360 gac cgg aaa aca gag tct tcc ctg agc tta gac ata cac agc aag agc    4485
Asp Arg Lys Thr Glu Ser Ser Leu Ser Leu Asp Ile His Ser Lys Ser
1365                1370                1375 caa gcc ggc tcg acc cct ctg aca agg gag aac agc acc ttc agt ata    4533
Gln Ala Gly Ser Thr Pro Leu Thr Arg Glu Asn Ser Thr Phe Ser Ile
1380                1385                1390                1395
```

| | |
|---|---|
| aac gat gct gct tcc cac aca agt acc atg agc tcc cga cac tct gcc<br>Asn Asp Ala Ala Ser His Thr Ser Thr Met Ser Ser Arg His Ser Ala<br>              1400                        1405                        1410 | 4581 |
| agc cca gtg gtt ttc acc agt gcc cgg agt tca cct aaa gaa gag ctt<br>Ser Pro Val Val Phe Thr Ser Ala Arg Ser Ser Pro Lys Glu Glu Leu<br>        1415                        1420                        1425 | 4629 |
| cat cca gct gcc ccc tca cag ctc gca cca tcc ttc tcc tcc tct tcc<br>His Pro Ala Ala Pro Ser Gln Leu Ala Pro Ser Phe Ser Ser Ser Ser<br>    1430                        1435                        1440 | 4677 |
| tcc tcc tcc tct ggt cct agg agt ttt tac cct cgc cag ggc gct act<br>Ser Ser Ser Ser Gly Pro Arg Ser Phe Tyr Pro Arg Gln Gly Ala Thr<br>1445                        1450                        1455 | 4725 |
| agc aag tac ctg att gga tgg aaa aaa ccc gaa gga acc ata aac tcc<br>Ser Lys Tyr Leu Ile Gly Trp Lys Lys Pro Glu Gly Thr Ile Asn Ser<br>1460                        1465                        1470                        1475 | 4773 |
| gtg gga ttt atg gac acg aga aag cgt cat cag agc gat ggc aat gaa<br>Val Gly Phe Met Asp Thr Arg Lys Arg His Gln Ser Asp Gly Asn Glu<br>              1480                        1485                        1490 | 4821 |
| ata gcc cac acc agg ctg cgt gcc tca acc aga gac ctc cgg gca tct<br>Ile Ala His Thr Arg Leu Arg Ala Ser Thr Arg Asp Leu Arg Ala Ser<br>        1495                        1500                        1505 | 4869 |
| cct aag cca acc tcc aag tcc acc att gaa gaa gat cta aag aaa cta<br>Pro Lys Pro Thr Ser Lys Ser Thr Ile Glu Glu Asp Leu Lys Lys Leu<br>    1510                        1515                        1520 | 4917 |
| att gat ctt gaa agc cca act cct gaa tca cag aag agt ttt aag ttc<br>Ile Asp Leu Glu Ser Pro Thr Pro Glu Ser Gln Lys Ser Phe Lys Phe<br>1525                        1530                        1535 | 4965 |
| cac gca ctc tcc tct cct cag tct cct ttc ccc agc acc ccc acc tca<br>His Ala Leu Ser Ser Pro Gln Ser Pro Phe Pro Ser Thr Pro Thr Ser<br>1540                        1545                        1550                        1555 | 5013 |
| cgg cgg gcc ttg cac aga aca ctg tcg gac gag agc att tac aat agc<br>Arg Arg Ala Leu His Arg Thr Leu Ser Asp Glu Ser Ile Tyr Asn Ser<br>              1560                        1565                        1570 | 5061 |
| cag agg gag cac ttt ttc acc tcc agg gcg tca ctt ctg gac caa gcc<br>Gln Arg Glu His Phe Phe Thr Ser Arg Ala Ser Leu Leu Asp Gln Ala<br>        1575                        1580                        1585 | 5109 |
| ctg ccc aac gac gtc ctc ttc agt agc acg tac cct tct ctc ccc aag<br>Leu Pro Asn Asp Val Leu Phe Ser Ser Thr Tyr Pro Ser Leu Pro Lys<br>    1590                        1595                        1600 | 5157 |
| tcg ctc ccg ttg agg agg cct tct tac acc tta gga atg aaa tcg ctg<br>Ser Leu Pro Leu Arg Arg Pro Ser Tyr Thr Leu Gly Met Lys Ser Leu<br>1605                        1610                        1615 | 5205 |
| cat gga gag ttc tca gcc tcg gac agc tcc ctc act gac atc cag gag<br>His Gly Glu Phe Ser Ala Ser Asp Ser Ser Leu Thr Asp Ile Gln Glu<br>1620                        1625                        1630                        1635 | 5253 |
| acc cgc agg cag cct atg ccc gac cct ggc ctg atg ccc ctg cct gac<br>Thr Arg Arg Gln Pro Met Pro Asp Pro Gly Leu Met Pro Leu Pro Asp<br>              1640                        1645                        1650 | 5301 |
| act gct gca gac ttg gat tgg tcc aac ctg gta gat gct gcc aaa gcc<br>Thr Ala Ala Asp Leu Asp Trp Ser Asn Leu Val Asp Ala Ala Lys Ala<br>        1655                        1660                        1665 | 5349 |
| tat gag gtc cag aga gcc tca ttt ttt gct gct agt gat gaa aac cat<br>Tyr Glu Val Gln Arg Ala Ser Phe Phe Ala Ala Ser Asp Glu Asn His<br>    1670                        1675                        1680 | 5397 |
| cgc ccc ttg agt gct gca tcc aac agt gat cag ctg gag gac cag gct<br>Arg Pro Leu Ser Ala Ala Ser Asn Ser Asp Gln Leu Glu Asp Gln Ala<br>1685                        1690                        1695 | 5445 |
| ctg gcc cag atg aag cct tac agc agc agt aaa gac tcc tct ccc act<br>Leu Ala Gln Met Lys Pro Tyr Ser Ser Ser Lys Asp Ser Ser Pro Thr<br>1700                        1705                        1710                        1715 | 5493 |

-continued

```
ctg gct tct aaa gtg gac cag ctg gaa ggt atg ctg aag atg ctt cgg      5541
Leu Ala Ser Lys Val Asp Gln Leu Glu Gly Met Leu Lys Met Leu Arg
        1720                1725                1730 gaa gat ttg aag aag gaa aaa gaa gac aaa gct cac ctt cag gcg gag      5589
Glu Asp Leu Lys Lys Glu Lys Glu Asp Lys Ala His Leu Gln Ala Glu
        1735                1740                1745 gtg cag cac ctg cga gag gac aac ctg agg cta cag gag gag tcc cag      5637
Val Gln His Leu Arg Glu Asp Asn Leu Arg Leu Gln Glu Glu Ser Gln
        1750                1755                1760 aac gcc tcg gac aag ctg aag aag ttc aca gaa tgg gtc ttc aac acc      5685
Asn Ala Ser Asp Lys Leu Lys Lys Phe Thr Glu Trp Val Phe Asn Thr
    1765                1770                1775 ata gac atg agc tagggaaggc tgaggaggac aggagaaggg cccagacact           5737
Ile Asp Met Ser
1780 ccctccagtg agtgtcctgc agcccttatt ccctccatag aaagcatcct cagagcacct     5797 tccctggctt cctactctgc ccccttcgg ggagtgcaca acacaatagt tgcagatcaa      5857 caatcatcac ctgccttttg tagaaaagaa aacaaaaaa agtaaataaa aattttaaac      5917 agtaaaataa aagtttaact gctaaaaaaa aaaaaaaaa aaaaaaaa                    5965

<210> SEQ ID NO 2
<211> LENGTH: 1783
<212> TYPE: PRT
<213> ORGANISM: Homo sapiens

<400> SEQUENCE: 2

Met Thr Ser Leu Lys Arg Ser Gln Thr Glu Arg Pro Leu Ala Thr Asp
  1               5                  10                  15

Arg Ala Ser Val Val Gly Thr Asp Gly Thr Pro Lys Val His Thr Asp
                 20                  25                  30

Asp Phe Tyr Met Arg Arg Phe Arg Ser Gln Asn Gly Ser Leu Gly Ser
             35                  40                  45

Ser Val Met Ala Pro Val Gly Pro Pro Arg Ser Glu Gly Ser His His
         50                  55                  60

Ile Thr Ser Thr Pro Gly Val Pro Lys Met Gly Val Arg Ala Arg Ile
 65                  70                  75                  80

Ala Asp Trp Pro Pro Arg Lys Glu Asn Ile Lys Glu Ser Ser Arg Ser
                 85                  90                  95

Ser Gln Glu Ile Glu Thr Ser Ser Cys Leu Asp Ser Leu Ser Ser Lys
                100                 105                 110

Ser Ser Pro Val Ser Gln Gly Ser Ser Val Ser Leu Asn Ser Asn Asp
            115                 120                 125

Ser Ala Met Leu Lys Ser Ile Gln Asn Thr Leu Lys Asn Lys Thr Arg
        130                 135                 140

Pro Ser Glu Asn Met Asp Ser Arg Phe Leu Met Pro Glu Ala Tyr Pro
145                 150                 155                 160

Ser Ser Pro Arg Lys Ala Leu Arg Arg Ile Arg Gln Arg Ser Asn Ser
                165                 170                 175

Asp Ile Thr Ile Ser Glu Leu Asp Val Asp Ser Phe Asp Glu Cys Ile
            180                 185                 190

Ser Pro Thr Tyr Lys Thr Gly Pro Ser Leu His Arg Glu Tyr Gly Ser
        195                 200                 205

Thr Ser Ser Ile Asp Lys Gln Gly Thr Ser Gly Glu Ser Phe Phe Asp
    210                 215                 220
```

-continued

```
Leu Leu Lys Gly Tyr Lys Asp Asp Lys Ser Asp Arg Gly Pro Thr Pro
225                 230                 235                 240

Thr Lys Leu Ser Asp Phe Leu Ile Thr Gly Gly Lys Gly Ser Gly
            245                 250                 255

Phe Ser Leu Asp Val Ile Asp Gly Pro Ile Ser Gln Arg Glu Asn Leu
                260                 265                 270

Arg Leu Phe Lys Glu Arg Glu Lys Pro Leu Lys Arg Arg Ser Lys Ser
            275                 280                 285

Glu Thr Gly Asp Ser Ser Ile Phe Arg Lys Leu Arg Asn Ala Lys Gly
            290                 295                 300

Glu Glu Leu Gly Lys Ser Ser Asp Leu Glu Asp Asn Arg Ser Glu Asp
305                 310                 315                 320

Ser Val Arg Pro Trp Thr Cys Pro Lys Cys Phe Ala His Tyr Asp Val
                325                 330                 335

Gln Ser Ile Leu Phe Asp Leu Asn Glu Ala Ile Met Asn Arg His Asn
                340                 345                 350

Val Ile Lys Arg Arg Asn Thr Thr Thr Gly Ala Ser Ala Ala Ala Val
            355                 360                 365

Ala Ser Leu Val Ser Gly Pro Leu Ser His Ser Ala Ser Phe Ser Ser
370                 375                 380

Pro Met Gly Ser Thr Glu Asp Leu Asn Ser Lys Gly Ser Leu Ser Met
385                 390                 395                 400

Asp Gln Gly Asp Asp Lys Ser Asn Glu Leu Val Met Ser Cys Pro Tyr
                405                 410                 415

Phe Arg Asn Glu Ile Gly Gly Glu Gly Glu Arg Lys Ile Ser Leu Ser
            420                 425                 430

Lys Ser Asn Ser Gly Ser Phe Ser Gly Cys Glu Ser Ala Ser Phe Glu
            435                 440                 445

Ser Thr Leu Ser Ser His Cys Thr Asn Ala Gly Val Ala Val Leu Glu
            450                 455                 460

Val Pro Lys Glu Asn Leu Val Leu His Leu Asp Arg Val Lys Arg Tyr
465                 470                 475                 480

Ile Val Glu His Val Asp Leu Gly Ala Tyr Tyr Arg Lys Phe Phe
                485                 490                 495

Tyr Gln Lys Glu His Trp Asn Tyr Phe Gly Ala Asp Glu Asn Leu Gly
            500                 505                 510

Pro Val Ala Val Ser Ile Arg Arg Glu Lys Pro Asp Glu Met Lys Glu
            515                 520                 525

Asn Gly Ser Pro Tyr Asn Tyr Arg Ile Ile Phe Arg Thr Ser Glu Leu
530                 535                 540

Met Thr Leu Arg Gly Ser Val Leu Glu Asp Ala Ile Pro Ser Thr Ala
545                 550                 555                 560

Lys His Ser Thr Ala Arg Gly Leu Pro Leu Lys Glu Val Leu Glu His
                565                 570                 575

Val Val Pro Glu Leu Asn Val Gln Cys Leu Arg Leu Ala Phe Asn Thr
            580                 585                 590

Pro Lys Val Thr Glu Gln Leu Met Lys Leu Asp Glu Gln Gly Leu Asn
            595                 600                 605

Tyr Gln Gln Lys Val Gly Ile Met Tyr Cys Lys Ala Gly Gln Ser Thr
            610                 615                 620

Glu Glu Glu Met Tyr Asn Asn Glu Ser Ala Gly Pro Ala Phe Glu Glu
625                 630                 635                 640

Phe Leu Gln Leu Leu Gly Glu Arg Val Arg Leu Lys Gly Phe Glu Lys
```

```
                645                 650                 655
Tyr Arg Ala Gln Leu Asp Thr Lys Thr Asp Ser Thr Gly Thr His Ser
            660                 665                 670
Leu Tyr Thr Thr Tyr Lys Asp Tyr Glu Ile Met Phe His Val Ser Thr
        675                 680                 685
Met Leu Pro Tyr Thr Pro Asn Asn Lys Gln Gln Leu Leu Arg Lys Arg
    690                 695                 700
His Ile Gly Asn Asp Ile Val Thr Ile Val Phe Gln Glu Pro Gly Ala
705                 710                 715                 720
Gln Pro Phe Ser Pro Lys Asn Ile Arg Ser His Phe Gln His Val Phe
                725                 730                 735
Val Ile Val Arg Val His Asn Pro Cys Ser Asp Ser Val Cys Tyr Ser
            740                 745                 750
Val Ala Val Thr Arg Ser Arg Asp Val Pro Ser Phe Gly Pro Pro Ile
        755                 760                 765
Pro Lys Gly Val Thr Phe Pro Lys Ser Asn Val Phe Arg Asp Phe Leu
    770                 775                 780
Leu Ala Lys Val Ile Asn Ala Glu Asn Ala Ala His Lys Ser Glu Lys
785                 790                 795                 800
Phe Arg Ala Met Ala Thr Arg Thr Arg Gln Glu Tyr Leu Lys Asp Leu
                805                 810                 815
Ala Glu Lys Asn Val Thr Asn Thr Pro Ile Asp Pro Ser Gly Lys Phe
            820                 825                 830
Pro Phe Ile Ser Leu Ala Ser Lys Lys Glu Lys Ser Lys Pro Tyr
        835                 840                 845
Pro Gly Ala Glu Leu Ser Ser Met Gly Ala Ile Val Trp Ala Val Arg
    850                 855                 860
Ala Glu Asp Tyr Asn Lys Ala Met Glu Leu Asp Cys Leu Leu Gly Ile
865                 870                 875                 880
Ser Asn Glu Phe Ile Val Leu Ile Glu Gln Glu Thr Lys Ser Val Val
                885                 890                 895
Phe Asn Cys Ser Cys Arg Asp Val Ile Gly Trp Thr Ser Thr Asp Thr
            900                 905                 910
Ser Leu Lys Ile Phe Tyr Glu Arg Gly Glu Cys Val Ser Val Gly Ser
        915                 920                 925
Phe Ile Asn Ile Glu Glu Ile Lys Glu Ile Val Lys Arg Leu Gln Phe
    930                 935                 940
Val Ser Lys Gly Cys Glu Ser Val Glu Met Thr Leu Arg Arg Asn Gly
945                 950                 955                 960
Leu Gly Gln Leu Gly Phe His Val Asn Tyr Glu Gly Ile Val Ala Asp
                965                 970                 975
Val Glu Pro Tyr Gly Tyr Ala Trp Gln Ala Gly Leu Arg Gln Gly Ser
            980                 985                 990
Arg Leu Val Glu Ile Cys Lys Val Ala Val Ala Thr Leu Ser His Glu
        995                 1000                1005
Gln Met Ile Asp Leu Leu Arg Thr Ser Val Thr Val Lys Val Val Ile
    1010                1015                1020
Ile Pro Pro His Asp Asp Cys Thr Pro Arg Arg Ser Cys Ser Glu Thr
1025                1030                1035                1040
Tyr Arg Met Pro Val Met Glu Tyr Lys Met Asn Glu Gly Val Ser Tyr
                1045                1050                1055
Glu Phe Lys Phe Pro Phe Arg Asn Asn Asn Lys Trp Gln Arg Asn Ala
            1060                1065                1070
```

```
Ser Lys Gly Pro His Ser Pro Gln Val Pro Ser Gln Val Gln Ser Pro
    1075                1080                1085

Met Thr Ser Arg Leu Asn Ala Gly Lys Gly Asp Gly Lys Met Pro Pro
    1090                1095                1100

Pro Glu Arg Ala Ala Asn Ile Pro Arg Ser Ile Ser Ser Asp Gly Arg
1105                1110                1115                1120

Pro Leu Glu Arg Arg Leu Ser Pro Gly Ser Asp Ile Tyr Val Thr Val
                1125                1130                1135

Ser Ser Met Ala Leu Ala Arg Ser Gln Cys Arg Asn Ser Pro Ser Asn
            1140                1145                1150

Leu Ser Ser Ser Ser Asp Thr Gly Ser Val Gly Gly Thr Tyr Arg Gln
            1155                1160                1165

Lys Ser Met Pro Glu Gly Phe Gly Val Ser Arg Arg Ser Pro Ala Ser
    1170                1175                1180

Ile Asp Arg Gln Asn Thr Gln Ser Asp Ile Gly Gly Ser Gly Lys Ser
1185                1190                1195                1200

Thr Pro Ser Trp Gln Arg Ser Glu Asp Ser Ile Ala Asp Gln Met Glu
                1205                1210                1215

Pro Thr Cys His Leu Pro Ala Val Ser Lys Val Leu Pro Ala Phe Arg
            1220                1225                1230

Glu Ser Pro Ser Gly Arg Leu Met Arg Gln Asp Pro Val Val His Leu
            1235                1240                1245

Ser Pro Asn Lys Gln Gly His Ser Asp Ser His Tyr Ser Ser His Ser
    1250                1255                1260

Ser Ser Asn Thr Leu Ser Ser Asn Ala Ser Ser Ala His Ser Asp Glu
1265                1270                1275                1280

Lys Trp Tyr Asp Gly Asp Arg Thr Glu Ser Glu Leu Asn Ser Tyr Asn
                1285                1290                1295

Tyr Leu Gln Gly Thr Ser Ala Asp Ser Gly Ile Asp Thr Thr Ser Tyr
            1300                1305                1310

Gly Pro Ser His Gly Ser Thr Ala Ser Leu Gly Ala Ala Thr Ser Ser
            1315                1320                1325

Pro Arg Ser Gly Pro Gly Lys Glu Lys Val Ala Pro Leu Trp His Ser
    1330                1335                1340

Ser Ser Glu Val Ile Ser Met Ala Asp Arg Thr Leu Glu Thr Glu Ser
1345                1350                1355                1360

His Gly Leu Asp Arg Lys Thr Gly Ser Ser Leu Ser Leu Asp Ile His
                1365                1370                1375

Ser Lys Ser Gln Ala Gly Ser Thr Pro Leu Thr Arg Glu Asn Ser Thr
            1380                1385                1390

Phe Ser Ile Asn Asp Ala Ala Ser His Thr Ser Thr Met Ser Ser Arg
    1395                1400                1405

His Ser Ala Ser Pro Val Val Phe Thr Ser Ala Arg Ser Ser Pro Lys
    1410                1415                1420

Glu Glu Leu His Pro Ala Ala Pro Ser Gln Leu Ala Pro Ser Phe Ser
1425                1430                1435                1440

Ser Ser Ser Ser Ser Ser Gly Pro Arg Ser Phe Tyr Pro Arg Gln
                1445                1450                1455

Gly Ala Thr Ser Lys Tyr Leu Ile Gly Trp Lys Lys Pro Glu Gly Thr
            1460                1465                1470

Ile Asn Ser Val Gly Phe Met Asp Thr Arg Lys Arg His Gln Ser Asp
            1475                1480                1485
```

-continued

```
Gly Asn Glu Ile Ala His Thr Arg Leu Arg Ala Ser Thr Arg Asp Leu
    1490                1495                1500
Arg Ala Ser Pro Lys Pro Thr Ser Lys Ser Thr Ile Glu Glu Asp Leu
1505                1510                1515                1520
Lys Lys Leu Ile Asp Leu Glu Ser Pro Thr Pro Glu Ser Gln Lys Ser
                1525                1530                1535
Phe Lys Phe His Ala Leu Ser Ser Pro Gln Ser Pro Phe Pro Ser Thr
            1540                1545                1550
Pro Thr Ser Arg Arg Ala Leu His Arg Thr Leu Ser Asp Glu Ser Ile
        1555                1560                1565
Tyr Asn Ser Gln Arg Glu His Phe Phe Thr Ser Arg Ala Ser Leu Leu
    1570                1575                1580
Asp Gln Ala Leu Pro Asn Asp Val Leu Phe Ser Ser Thr Tyr Pro Ser
1585                1590                1595                1600
Leu Pro Lys Ser Leu Pro Leu Arg Arg Pro Ser Tyr Thr Leu Gly Met
                1605                1610                1615
Lys Ser Leu His Gly Glu Phe Ser Ala Ser Asp Ser Ser Leu Thr Asp
            1620                1625                1630
Ile Gln Glu Thr Arg Arg Gln Pro Met Pro Asp Pro Gly Leu Met Pro
        1635                1640                1645
Leu Pro Asp Thr Ala Ala Asp Leu Asp Trp Ser Asn Leu Val Asp Ala
    1650                1655                1660
Ala Lys Ala Tyr Glu Val Gln Arg Ala Ser Phe Phe Ala Ala Ser Asp
1665                1670                1675                1680
Glu Asn His Arg Pro Leu Ser Ala Ala Ser Asn Ser Asp Gln Leu Glu
                1685                1690                1695
Asp Gln Ala Leu Ala Gln Met Lys Pro Tyr Ser Ser Ser Lys Asp Ser
            1700                1705                1710
Ser Pro Thr Leu Ala Ser Lys Val Asp Gln Leu Glu Gly Met Leu Lys
        1715                1720                1725
Met Leu Arg Glu Asp Leu Lys Lys Glu Lys Glu Asp Lys Ala His Leu
    1730                1735                1740
Gln Ala Glu Val Gln His Leu Arg Glu Asp Asn Leu Arg Leu Gln Glu
1745                1750                1755                1760
Glu Ser Gln Asn Ala Ser Asp Lys Leu Lys Lys Phe Thr Glu Trp Val
                1765                1770                1775
Phe Asn Thr Ile Asp Met Ser
            1780
```

<210> SEQ ID NO 3
<211> LENGTH: 6028
<212> TYPE: DNA
<213> ORGANISM: Homo sapiens
<220> FEATURE:
<221> NAME/KEY: CDS
<222> LOCATION: (349)..(5760)

<400> SEQUENCE: 3

```
ggtgtggacg ttgtctaaat ttcggtagcc atggcacaag aatataagaa agcatgggat    60
tatggcaacc acagaatctc agtagtacaa gttccattca gttttttctg aaagaaagcc   120
ctctgttaaa gtgaagcaaa gaaactgttg tggattataa cgtttagaag ttccaatttt   180
tcagtgcttt acaaataaag catcatttaa ccttttaaat gaaaaagatt aagatctcat   240
gcaactgttg tattttctgg aagccattct ccaaaaggga agtgcacatt taaaacacag   300
atatgatggt ccttgctgca gggatttaag tctacttgct tttacatc atg acc agc   357
```

-continued

```
                                          Met Thr Ser
                                            1
ttg aaa cgg tca cag aca gaa agg cct ctt gcc act gac agg gcc tct      405
Leu Lys Arg Ser Gln Thr Glu Arg Pro Leu Ala Thr Asp Arg Ala Ser
      5                  10                  15 gtt gtt ggc aca gac ggc acc ccc aaa gtc cac act gat gat ttc tac      453
Val Val Gly Thr Asp Gly Thr Pro Lys Val His Thr Asp Asp Phe Tyr
 20                  25                  30                  35 atg cgg cgc ttc cgg tcc caa aat ggc agc tta gga tca tca gtt atg      501
Met Arg Arg Phe Arg Ser Gln Asn Gly Ser Leu Gly Ser Ser Val Met
                 40                  45                  50 gct cct gta gga ccc ccc cga agt gaa ggt tct cac cat ata acc tca      549
Ala Pro Val Gly Pro Pro Arg Ser Glu Gly Ser His His Ile Thr Ser
                         55                  60                  65 acc ccc gga gtc cca aaa atg ggg gta agg gca agg att gca gat tgg      597
Thr Pro Gly Val Pro Lys Met Gly Val Arg Ala Arg Ile Ala Asp Trp
         70                  75                  80 ccc cca aga aag gaa aac ata aaa gaa tct agc cgt tca agc cag gaa      645
Pro Pro Arg Lys Glu Asn Ile Lys Glu Ser Ser Arg Ser Ser Gln Glu
             85                  90                  95 ata gaa acc tca agt tgc ctt gat agc ctg tcc tcc aaa agc agt cct      693
Ile Glu Thr Ser Ser Cys Leu Asp Ser Leu Ser Ser Lys Ser Ser Pro
100                 105                 110                 115 gtg agt cag gga agt tct gtt agc ctc aat tcc aat gac tca gcc atg      741
Val Ser Gln Gly Ser Ser Val Ser Leu Asn Ser Asn Asp Ser Ala Met
                    120                 125                 130 ctg aaa agc ata cag aac acg ctg aaa aac aag aca aga ccg tcg gag      789
Leu Lys Ser Ile Gln Asn Thr Leu Lys Asn Lys Thr Arg Pro Ser Glu
                135                 140                 145 aac atg gac tcc aga ttt ctc atg cct gaa gcc tac ccc agc tcc ccc      837
Asn Met Asp Ser Arg Phe Leu Met Pro Glu Ala Tyr Pro Ser Ser Pro
            150                 155                 160 aga aaa gct ctt cgc aga ata cgc cag cga agc aac agt gat atc acc      885
Arg Lys Ala Leu Arg Arg Ile Arg Gln Arg Ser Asn Ser Asp Ile Thr
165                 170                 175 ata agt gaa ctt gat gtg gat agc ttt gat gaa tgt atc tca cct aca      933
Ile Ser Glu Leu Asp Val Asp Ser Phe Asp Glu Cys Ile Ser Pro Thr
180                 185                 190                 195 tac aag act gga cca tca ctg cac agg gaa tat ggt agc aca tct tca      981
Tyr Lys Thr Gly Pro Ser Leu His Arg Glu Tyr Gly Ser Thr Ser Ser
                    200                 205                 210 att gat aaa cag gga aca tct gga gaa agc ttt ttt gat ttg tta aag     1029
Ile Asp Lys Gln Gly Thr Ser Gly Glu Ser Phe Phe Asp Leu Leu Lys
                215                 220                 225 ggc tac aaa gat gac aaa tct gat cga ggt cca act cca acc aag ctc     1077
Gly Tyr Lys Asp Asp Lys Ser Asp Arg Gly Pro Thr Pro Thr Lys Leu
            230                 235                 240 agt gac ttt ctc att act ggt ggt ggc aag ggt tct ggt ttc tct ttg     1125
Ser Asp Phe Leu Ile Thr Gly Gly Gly Lys Gly Ser Gly Phe Ser Leu
245                 250                 255 gat gta ata gac ggg cct atc tca cag aga gag aac ctc agg ctt ttt     1173
Asp Val Ile Asp Gly Pro Ile Ser Gln Arg Glu Asn Leu Arg Leu Phe
260                 265                 270                 275 aag gaa agg gaa aaa cca ctc aag cga cgt tca aaa tct gaa act gga     1221
Lys Glu Arg Glu Lys Pro Leu Lys Arg Arg Ser Lys Ser Glu Thr Gly
                280                 285                 290 gac tcc tct att ttt cgt aaa ttg cgc aat gcc aaa ggt gaa gaa ctt     1269
Asp Ser Ser Ile Phe Arg Lys Leu Arg Asn Ala Lys Gly Glu Glu Leu
            295                 300                 305
```

```
ggg aag tca tca gat ctt gaa gat aac cga tca gaa gac tct gtc agg      1317
Gly Lys Ser Ser Asp Leu Glu Asp Asn Arg Ser Glu Asp Ser Val Arg
        310                 315                 320 ccc tgg aca tgt cca aag tgc ttt gcc cac tat gat gtc cag agt ata      1365
Pro Trp Thr Cys Pro Lys Cys Phe Ala His Tyr Asp Val Gln Ser Ile
325                 330                 335 tta ttt gat ttg aat gag gca att atg aac agg cac aat gtt att aag      1413
Leu Phe Asp Leu Asn Glu Ala Ile Met Asn Arg His Asn Val Ile Lys
340                 345                 350                 355 agg aga aac acc acc act gga gct tcc gca gct gcc gtg gca tcc ttg      1461
Arg Arg Asn Thr Thr Thr Gly Ala Ser Ala Ala Ala Val Ala Ser Leu
            360                 365                 370 gtc tct gga cct ctg tct cat tca gcc agt ttt agc tcc cca atg ggc      1509
Val Ser Gly Pro Leu Ser His Ser Ala Ser Phe Ser Ser Pro Met Gly
        375                 380                 385 agc aca gag gac ctg aat tcc aaa gga agc ctc agc atg gac cag gga      1557
Ser Thr Glu Asp Leu Asn Ser Lys Gly Ser Leu Ser Met Asp Gln Gly
        390                 395                 400 gat gat aaa agc aat gag ctt gta atg agc tgt cca tat ttt cgg aat      1605
Asp Asp Lys Ser Asn Glu Leu Val Met Ser Cys Pro Tyr Phe Arg Asn
405                 410                 415 gag ata ggt gga gaa ggg gag agg aaa atc agc ctt tca aaa tca aat      1653
Glu Ile Gly Gly Glu Gly Glu Arg Lys Ile Ser Leu Ser Lys Ser Asn
420                 425                 430                 435 tct ggc tcc ttt agt gga tgt gaa agt gcc tcc ttt gag tct acc ctt      1701
Ser Gly Ser Phe Ser Gly Cys Glu Ser Ala Ser Phe Glu Ser Thr Leu
            440                 445                 450 agt tcc cat tgc aca aat gca gga gtg gca gta ctt gaa gtg ccc aag      1749
Ser Ser His Cys Thr Asn Ala Gly Val Ala Val Leu Glu Val Pro Lys
        455                 460                 465 gag aac ttg gtg ttg cac cta gat aga gtg aaa aga tac atc gtg gaa      1797
Glu Asn Leu Val Leu His Leu Asp Arg Val Lys Arg Tyr Ile Val Glu
        470                 475                 480 cac gta gat ctg ggt gca tac tat tat aga aaa ttt ttc tac cag aag      1845
His Val Asp Leu Gly Ala Tyr Tyr Tyr Arg Lys Phe Phe Tyr Gln Lys
485                 490                 495 gaa cac tgg aac tat ttt ggg gct gat gag aat ctt ggt cca gtg gct      1893
Glu His Trp Asn Tyr Phe Gly Ala Asp Glu Asn Leu Gly Pro Val Ala
500                 505                 510                 515 gtg agc att cga agg gaa aaa cca gat gaa atg aaa gaa aat gga tct      1941
Val Ser Ile Arg Arg Glu Lys Pro Asp Glu Met Lys Glu Asn Gly Ser
            520                 525                 530 ccg tac aac tac cga ata att ttt aga act agt gag ctc atg aca ctg      1989
Pro Tyr Asn Tyr Arg Ile Ile Phe Arg Thr Ser Glu Leu Met Thr Leu
        535                 540                 545 aga ggt tcg gtc ctg gag gac gcc att ccg tcg aca gcc aag cac tcg      2037
Arg Gly Ser Val Leu Glu Asp Ala Ile Pro Ser Thr Ala Lys His Ser
        550                 555                 560 aca gcc aga ggc ctg cct ctc aaa gaa gtg ctg gag cac gtg gtt cct      2085
Thr Ala Arg Gly Leu Pro Leu Lys Glu Val Leu Glu His Val Val Pro
565                 570                 575 gag ctc aat gtc cag tgc ctg cgg ttg gcc ttc aac aca ccc aag gtc      2133
Glu Leu Asn Val Gln Cys Leu Arg Leu Ala Phe Asn Thr Pro Lys Val
580                 585                 590                 595 aca gag cag ctc atg aaa ctg gat gaa caa ggg ctg aac tac cag cag      2181
Thr Glu Gln Leu Met Lys Leu Asp Glu Gln Gly Leu Asn Tyr Gln Gln
            600                 605                 610 aaa gta ggc atc atg tac tgc aaa gct gga cag agc act gaa gaa gag      2229
Lys Val Gly Ile Met Tyr Cys Lys Ala Gly Gln Ser Thr Glu Glu Glu
        615                 620                 625
```

-continued

| | | |
|---|---|---|
| atg tac aac aat gag tca gct ggc cca gcc ttt gaa gaa ttc ctt caa<br>Met Tyr Asn Asn Glu Ser Ala Gly Pro Ala Phe Glu Glu Phe Leu Gln<br>630 635 640 | 2277 |
| cta ttg gga gag cga gtt cgg ctc aaa gga ttt gag aag tat cga gca<br>Leu Leu Gly Glu Arg Val Arg Leu Lys Gly Phe Glu Lys Tyr Arg Ala<br>645 650 655 | 2325 |
| cag ctt gat acc aaa act gac tcc act gga acc cat tct ctg tac aca<br>Gln Leu Asp Thr Lys Thr Asp Ser Thr Gly Thr His Ser Leu Tyr Thr<br>660 665 670 675 | 2373 |
| aca tac aaa gat tat gaa att atg ttc cat gtt tct acc atg ctg cca<br>Thr Tyr Lys Asp Tyr Glu Ile Met Phe His Val Ser Thr Met Leu Pro<br>680 685 690 | 2421 |
| tac aca ccc aac aac aaa caa cag ctc ctg agg aag cgg cac att gga<br>Tyr Thr Pro Asn Asn Lys Gln Gln Leu Leu Arg Lys Arg His Ile Gly<br>695 700 705 | 2469 |
| aat gat atc gta aca att gtt ttc caa gag cct gga gca cag cca ttc<br>Asn Asp Ile Val Thr Ile Val Phe Gln Glu Pro Gly Ala Gln Pro Phe<br>710 715 720 | 2517 |
| agc cca aaa aac atc cga tcc cac ttc cag cac gtt ttc gtc atc gtc<br>Ser Pro Lys Asn Ile Arg Ser His Phe Gln His Val Phe Val Ile Val<br>725 730 735 | 2565 |
| agg gtg cac aat ccg tgc tct gac agt gtc tgt tat agt gtg gct gtt<br>Arg Val His Asn Pro Cys Ser Asp Ser Val Cys Tyr Ser Val Ala Val<br>740 745 750 755 | 2613 |
| acc agg tcc aga gat gtg cct tcc ttt ggg cct ccc att cct aaa ggg<br>Thr Arg Ser Arg Asp Val Pro Ser Phe Gly Pro Pro Ile Pro Lys Gly<br>760 765 770 | 2661 |
| gtc act ttc cct aag tca aat gtg ttc agg gac ttc ctt ttg gcg aaa<br>Val Thr Phe Pro Lys Ser Asn Val Phe Arg Asp Phe Leu Leu Ala Lys<br>775 780 785 | 2709 |
| gtg att aat gca gaa aat gct gct cat aaa tcg gag aag ttt cgg gcc<br>Val Ile Asn Ala Glu Asn Ala Ala His Lys Ser Glu Lys Phe Arg Ala<br>790 795 800 | 2757 |
| atg gca act cgg acc cgc cag gaa tac ctg aaa gat ctg gca gaa aag<br>Met Ala Thr Arg Thr Arg Gln Glu Tyr Leu Lys Asp Leu Ala Glu Lys<br>805 810 815 | 2805 |
| aat gtc acc aac acc cct atc gac cct tct ggc aag ttt ccg ttc atc<br>Asn Val Thr Asn Thr Pro Ile Asp Pro Ser Gly Lys Phe Pro Phe Ile<br>820 825 830 835 | 2853 |
| tct ctg gct tcc aag aag aag gaa aag tct aag cca tat cca gga gcc<br>Ser Leu Ala Ser Lys Lys Lys Glu Lys Ser Lys Pro Tyr Pro Gly Ala<br>840 845 850 | 2901 |
| gag ctc agc agc atg ggg gcc att gta tgg gca gtc cgg gct gaa gac<br>Glu Leu Ser Ser Met Gly Ala Ile Val Trp Ala Val Arg Ala Glu Asp<br>855 860 865 | 2949 |
| tac aac aag gcc atg gaa cta gac tgc ctt tta ggg atc tcc aat gag<br>Tyr Asn Lys Ala Met Glu Leu Asp Cys Leu Leu Gly Ile Ser Asn Glu<br>870 875 880 | 2997 |
| ttc att gtg ctc att gaa cag gaa aca aag agc gtg gtc ttc aat tgt<br>Phe Ile Val Leu Ile Glu Gln Glu Thr Lys Ser Val Val Phe Asn Cys<br>885 890 895 | 3045 |
| tcc tgt aga gat gtg ata ggg tgg act tca act gac acc agc ctc aaa<br>Ser Cys Arg Asp Val Ile Gly Trp Thr Ser Thr Asp Thr Ser Leu Lys<br>900 905 910 915 | 3093 |
| atc ttc tat gaa cga gga gaa tgt gtt tca gtg ggt agt ttt att aac<br>Ile Phe Tyr Glu Arg Gly Glu Cys Val Ser Val Gly Ser Phe Ile Asn<br>920 925 930 | 3141 |
| att gag gag atc aaa gag att gtc aaa agg ttg cag ttt gtt tca aaa<br>Ile Glu Glu Ile Lys Glu Ile Val Lys Arg Leu Gln Phe Val Ser Lys | 3189 |

```
                         935                 940                 945
ggc tgt gaa tcg gtg gag atg act ctg cga aga aat ggg cta gga cag          3237
Gly Cys Glu Ser Val Glu Met Thr Leu Arg Arg Asn Gly Leu Gly Gln
        950                 955                 960 ctt ggc ttc cat gtc aac tat gag ggc att gtg gcg gat gtg gag ccc          3285
Leu Gly Phe His Val Asn Tyr Glu Gly Ile Val Ala Asp Val Glu Pro
        965                 970                 975 tac ggt tat gcc tgg cag gca ggg ctg agg cag ggc agt cgc ctg gtg          3333
Tyr Gly Tyr Ala Trp Gln Ala Gly Leu Arg Gln Gly Ser Arg Leu Val
980                 985                 990                 995 gag atc tgc aag gtg gcg gta gcc act ctg agc cat gag cag atg atc          3381
Glu Ile Cys Lys Val Ala Val Ala Thr Leu Ser His Glu Gln Met Ile
                1000                1005                1010 gac ctc ctg aga aca tct gtc acg gtg aag gtt gtc atc att ccc ccg          3429
Asp Leu Leu Arg Thr Ser Val Thr Val Lys Val Val Ile Ile Pro Pro
            1015                1020                1025 cat gat gac tgc acc ccg cgg agg agt tgc tct gaa acc tac cgc atg          3477
His Asp Asp Cys Thr Pro Arg Arg Ser Cys Ser Glu Thr Tyr Arg Met
        1030                1035                1040 cca gtg atg gag tac aaa atg aat gaa ggt gtt tca tac gaa ttc aag          3525
Pro Val Met Glu Tyr Lys Met Asn Glu Gly Val Ser Tyr Glu Phe Lys
    1045                1050                1055 ttt ccc ttc cga aat aat aac aag tgg cag agg aac gcc agc aag ggg          3573
Phe Pro Phe Arg Asn Asn Asn Lys Trp Gln Arg Asn Ala Ser Lys Gly
1060                1065                1070                1075 cct cat tca cct caa gtc ccg tcc cag gtg cag agt ccc atg acc tcg          3621
Pro His Ser Pro Gln Val Pro Ser Gln Val Gln Ser Pro Met Thr Ser
                1080                1085                1090 cgg ctg aat gct gga aaa gga gat ggg aag atg cct cct cca gaa aga          3669
Arg Leu Asn Ala Gly Lys Gly Asp Gly Lys Met Pro Pro Pro Glu Arg
            1095                1100                1105 gcc gcc aac atc cct cga agc atc tcc agt gac ggg cgc cca cta gag          3717
Ala Ala Asn Ile Pro Arg Ser Ile Ser Ser Asp Gly Arg Pro Leu Glu
        1110                1115                1120 agg cgg ctg tct cct ggt tcg gac atc tat gtg acg gtc tca tcc atg          3765
Arg Arg Leu Ser Pro Gly Ser Asp Ile Tyr Val Thr Val Ser Ser Met
    1125                1130                1135 gct tta gca aga tcc cag tgt cgg aac tct cct agc aac ttg tct tca          3813
Ala Leu Ala Arg Ser Gln Cys Arg Asn Ser Pro Ser Asn Leu Ser Ser
1140                1145                1150                1155 tcc agt gat act ggt tct gtg ggg ggc act tac agg cag aag tcc atg          3861
Ser Ser Asp Thr Gly Ser Val Gly Gly Thr Tyr Arg Gln Lys Ser Met
                1160                1165                1170 ccc gaa ggg ttt gga gtg agc cgt aga tcc cca gcc tcc att gac agg          3909
Pro Glu Gly Phe Gly Val Ser Arg Arg Ser Pro Ala Ser Ile Asp Arg
            1175                1180                1185 cag aac acc cag tca gat att ggt ggc agc gga aaa tcc acg cct agc          3957
Gln Asn Thr Gln Ser Asp Ile Gly Gly Ser Gly Lys Ser Thr Pro Ser
        1190                1195                1200 tgg caa aga agt gag gat agc att gct gac cag atg gct tac agt tat          4005
Trp Gln Arg Ser Glu Asp Ser Ile Ala Asp Gln Met Ala Tyr Ser Tyr
    1205                1210                1215 aga gga cct cag gat ttc aat tct ttt gtc ctc gag cag cat gaa tat          4053
Arg Gly Pro Gln Asp Phe Asn Ser Phe Val Leu Glu Gln His Glu Tyr
1220                1225                1230                1235 aca gag cca aca tgc cat ctc cca gca gta tca aag gta ctg cca gct          4101
Thr Glu Pro Thr Cys His Leu Pro Ala Val Ser Lys Val Leu Pro Ala
                1240                1245                1250 ttc cga gag agc ccc agt ggg aga tta atg cgg cag gat cca gtg gtt          4149
```

-continued

```
Phe Arg Glu Ser Pro Ser Gly Arg Leu Met Arg Gln Asp Pro Val Val
        1255                1260                1265 cat ttg tct cca aac aaa caa ggg cat tct gat agc cac tac tcg agc     4197
His Leu Ser Pro Asn Lys Gln Gly His Ser Asp Ser His Tyr Ser Ser
    1270                1275                1280 cac tcc agt agc aat act ctc tcc agc aat gcg tca agt gcc cat agt     4245
His Ser Ser Ser Asn Thr Leu Ser Ser Asn Ala Ser Ser Ala His Ser
    1285                1290                1295 gat gag aag tgg tac gat ggg gac cgc aca gaa tcc gaa ctc aac agc     4293
Asp Glu Lys Trp Tyr Asp Gly Asp Arg Thr Glu Ser Glu Leu Asn Ser
1300                1305                1310                1315 tat aac tat ctg caa ggc acc tct gct gac agt ggc att gac acc acc     4341
Tyr Asn Tyr Leu Gln Gly Thr Ser Ala Asp Ser Gly Ile Asp Thr Thr
        1320                1325                1330 tct tat ggc ccc agc cac ggg agc aca gcc tcg ctg ggg gct gcc aca     4389
Ser Tyr Gly Pro Ser His Gly Ser Thr Ala Ser Leu Gly Ala Ala Thr
        1335                1340                1345 tcg tca cct cgc tca ggg cca ggc aag gag aaa gtg gca ccc cta tgg     4437
Ser Ser Pro Arg Ser Gly Pro Gly Lys Glu Lys Val Ala Pro Leu Trp
    1350                1355                1360 cac agc tcc agt gaa gta atc tcc atg gca gat cgg act ttg gag aca     4485
His Ser Ser Ser Glu Val Ile Ser Met Ala Asp Arg Thr Leu Glu Thr
    1365                1370                1375 gag agc cac ggc ctg gac cgg aaa aca gag tct tcc ctg agc tta gac     4533
Glu Ser His Gly Leu Asp Arg Lys Thr Glu Ser Ser Leu Ser Leu Asp
1380                1385                1390                1395 ata cac agc aag agc caa gcc ggc tcg acc cct ctg aca agg gag aac     4581
Ile His Ser Lys Ser Gln Ala Gly Ser Thr Pro Leu Thr Arg Glu Asn
                1400                1405                1410 agc acc ttc agt ata aac gat gct gct tcc cac aca agt acc atg agc     4629
Ser Thr Phe Ser Ile Asn Asp Ala Ala Ser His Thr Ser Thr Met Ser
        1415                1420                1425 tcc cga cac tct gcc agc cca gtg gtt ttc acc agt gcc cgg agt tca     4677
Ser Arg His Ser Ala Ser Pro Val Val Phe Thr Ser Ala Arg Ser Ser
            1430                1435                1440 cct aaa gaa gag ctt cat cca gct gcc ccc tca cag ctc gca cca tcc     4725
Pro Lys Glu Glu Leu His Pro Ala Ala Pro Ser Gln Leu Ala Pro Ser
    1445                1450                1455 ttc tcc tcc tct tcc tcc tcc tcc tct ggt cct agg agt ttt tac cct     4773
Phe Ser Ser Ser Ser Ser Ser Ser Ser Gly Pro Arg Ser Phe Tyr Pro
1460                1465                1470                1475 cgc cag ggc gct act agc aag tac ctg att gga tgg aaa aaa ccc gaa     4821
Arg Gln Gly Ala Thr Ser Lys Tyr Leu Ile Gly Trp Lys Lys Pro Glu
            1480                1485                1490 gga acc ata aac tcc gtg gga ttt atg gac acg aga aag cgt cat cag     4869
Gly Thr Ile Asn Ser Val Gly Phe Met Asp Thr Arg Lys Arg His Gln
        1495                1500                1505 agc gat ggc aat gaa ata gcc cac acc agg ctg cgt gcc tca acc aga     4917
Ser Asp Gly Asn Glu Ile Ala His Thr Arg Leu Arg Ala Ser Thr Arg
    1510                1515                1520 gac ctc cgg gca tct cct aag cca acc tcc aag tcc acc att gaa gaa     4965
Asp Leu Arg Ala Ser Pro Lys Pro Thr Ser Lys Ser Thr Ile Glu Glu
    1525                1530                1535 gat cta aag aaa cta att gat ctt gaa agc cca act cct gaa tca cag     5013
Asp Leu Lys Lys Leu Ile Asp Leu Glu Ser Pro Thr Pro Glu Ser Gln
1540                1545                1550                1555 aag agt ttt aag ttc cac gca ctc tcc tct cct cag tct cct ttc ccc     5061
Lys Ser Phe Lys Phe His Ala Leu Ser Ser Pro Gln Ser Pro Phe Pro
            1560                1565                1570
```

-continued

```
agc acc ccc acc tca cgg cgg gcc ttg cac aga aca ctg tcg gac gag      5109
Ser Thr Pro Thr Ser Arg Arg Ala Leu His Arg Thr Leu Ser Asp Glu
        1575                1580                1585 agc att tac aat agc cag agg gag cac ttt ttc acc tcc agg gcg tca      5157
Ser Ile Tyr Asn Ser Gln Arg Glu His Phe Phe Thr Ser Arg Ala Ser
    1590                1595                1600 ctt ctg gac caa gcc ctg ccc aac gac gtc ctc ttc agt agc acg tac      5205
Leu Leu Asp Gln Ala Leu Pro Asn Asp Val Leu Phe Ser Ser Thr Tyr
1605                1610                1615 cct tct ctc ccc aag tcg ctc ccg ttg agg agg cct tct tac acc tta      5253
Pro Ser Leu Pro Lys Ser Leu Pro Leu Arg Arg Pro Ser Tyr Thr Leu
1620                1625                1630                1635 gga atg aaa tcg ctg cat gga gag ttc tca gcc tcg gac agc tcc ctc      5301
Gly Met Lys Ser Leu His Gly Glu Phe Ser Ala Ser Asp Ser Ser Leu
        1640                1645                1650 act gac atc cag gag acc cgc agg cag cct atg ccc gac cct ggc ctg      5349
Thr Asp Ile Gln Glu Thr Arg Arg Gln Pro Met Pro Asp Pro Gly Leu
    1655                1660                1665 atg ccc ctg cct gac act gct gca gac ttg gat tgg tcc aac ctg gta      5397
Met Pro Leu Pro Asp Thr Ala Ala Asp Leu Asp Trp Ser Asn Leu Val
1670                1675                1680 gat gct gcc aaa gcc tat gag gtc cag aga gcc tca ttt ttt gct gct      5445
Asp Ala Ala Lys Ala Tyr Glu Val Gln Arg Ala Ser Phe Phe Ala Ala
1685                1690                1695 agt gat gaa aac cat cgc ccc ttg agt gct gca tcc aac agt gat cag      5493
Ser Asp Glu Asn His Arg Pro Leu Ser Ala Ala Ser Asn Ser Asp Gln
1700                1705                1710                1715 ctg gag gac cag gct ctg gcc cag atg aag cct tac agc agc agt aaa      5541
Leu Glu Asp Gln Ala Leu Ala Gln Met Lys Pro Tyr Ser Ser Ser Lys
        1720                1725                1730 gac tcc tct ccc act ctg gct tct aaa gtg gac cag ctg gaa ggt atg      5589
Asp Ser Ser Pro Thr Leu Ala Ser Lys Val Asp Gln Leu Glu Gly Met
    1735                1740                1745 ctg aag atg ctt cgg gaa gat ttg aag aag gaa aaa gaa gac aaa gct      5637
Leu Lys Met Leu Arg Glu Asp Leu Lys Lys Glu Lys Glu Asp Lys Ala
1750                1755                1760 cac ctt cag gcg gag gtg cag cac ctg cga gag gac aac ctg agg cta      5685
His Leu Gln Ala Glu Val Gln His Leu Arg Glu Asp Asn Leu Arg Leu
1765                1770                1775 cag gag gag tcc cag aac gcc tcg gac aag ctg aag aag ttc aca gaa      5733
Gln Glu Glu Ser Gln Asn Ala Ser Asp Lys Leu Lys Lys Phe Thr Glu
        1780                1785                1790                1795 tgg gtc ttc aac acc ata gac atg agc tagggaaggc tgaggaggac            5780
Trp Val Phe Asn Thr Ile Asp Met Ser
                    1800 aggagaaggg cccagacact ccctccagtg agtgtcctgc agcccttatt ccctccatag    5840 aaagcatcct cagagcacct tccctggctt cctactctgc cccctttcgg ggagtgcaca   5900 acacaatagt tgcagatcaa caatcatcac ctgcctttttg tagaaaagaa aaacaaaaaa   5960 agtaaataaa aattttaaac agtaaaataa agtttaact gctaaaaaaa aaaaaaaaa      6020 aaaaaaaa                                                              6028

<210> SEQ ID NO 4
<211> LENGTH: 1804
<212> TYPE: PRT
<213> ORGANISM: Homo sapiens

<400> SEQUENCE: 4

Met Thr Ser Leu Lys Arg Ser Gln Thr Glu Arg Pro Leu Ala Thr Asp
```

-continued

```
  1               5                    10                   15
Arg Ala Ser Val Val Gly Thr Asp Gly Thr Pro Lys Val His Thr Asp
             20                  25                  30

Asp Phe Tyr Met Arg Arg Phe Arg Ser Gln Asn Gly Ser Leu Gly Ser
             35                  40                  45

Ser Val Met Ala Pro Val Gly Pro Pro Arg Ser Glu Gly Ser His His
             50                  55                  60

Ile Thr Ser Thr Pro Gly Val Pro Lys Met Gly Val Arg Ala Arg Ile
 65                  70                  75                  80

Ala Asp Trp Pro Pro Arg Lys Glu Asn Ile Lys Glu Ser Ser Arg Ser
                 85                  90                  95

Ser Gln Glu Ile Glu Thr Ser Ser Cys Leu Asp Ser Leu Ser Ser Lys
            100                 105                 110

Ser Ser Pro Val Ser Gln Gly Ser Ser Val Ser Leu Asn Ser Asn Asp
            115                 120                 125

Ser Ala Met Leu Lys Ser Ile Gln Asn Thr Leu Lys Asn Lys Thr Arg
130                 135                 140

Pro Ser Glu Asn Met Asp Ser Arg Phe Leu Met Pro Glu Ala Tyr Pro
145                 150                 155                 160

Ser Ser Pro Arg Lys Ala Leu Arg Arg Ile Arg Gln Arg Ser Asn Ser
                165                 170                 175

Asp Ile Thr Ile Ser Glu Leu Asp Val Asp Ser Phe Asp Glu Cys Ile
                180                 185                 190

Ser Pro Thr Tyr Lys Thr Gly Pro Ser Leu His Arg Glu Tyr Gly Ser
                195                 200                 205

Thr Ser Ser Ile Asp Lys Gln Gly Thr Ser Gly Glu Ser Phe Phe Asp
210                 215                 220

Leu Leu Lys Gly Tyr Lys Asp Asp Lys Ser Asp Arg Gly Pro Thr Pro
225                 230                 235                 240

Thr Lys Leu Ser Asp Phe Leu Ile Thr Gly Gly Lys Gly Ser Gly
                245                 250                 255

Phe Ser Leu Asp Val Ile Asp Gly Pro Ile Ser Gln Arg Glu Asn Leu
                260                 265                 270

Arg Leu Phe Lys Glu Arg Glu Lys Pro Leu Lys Arg Arg Ser Lys Ser
                275                 280                 285

Glu Thr Gly Asp Ser Ser Ile Phe Arg Lys Leu Arg Asn Ala Lys Gly
290                 295                 300

Glu Glu Leu Gly Lys Ser Ser Asp Leu Glu Asp Asn Arg Ser Glu Asp
305                 310                 315                 320

Ser Val Arg Pro Trp Thr Cys Pro Lys Cys Phe Ala His Tyr Asp Val
                325                 330                 335

Gln Ser Ile Leu Phe Asp Leu Asn Glu Ala Ile Met Asn Arg His Asn
                340                 345                 350

Val Ile Lys Arg Arg Asn Thr Thr Gly Ala Ser Ala Ala Ala Val
                355                 360                 365

Ala Ser Leu Val Ser Gly Pro Leu Ser His Ser Ala Ser Phe Ser Ser
                370                 375                 380

Pro Met Gly Ser Thr Glu Asp Leu Asn Ser Lys Gly Ser Leu Ser Met
385                 390                 395                 400

Asp Gln Gly Asp Asp Lys Ser Asn Glu Leu Val Met Ser Cys Pro Tyr
                405                 410                 415

Phe Arg Asn Glu Ile Gly Gly Glu Gly Arg Lys Ile Ser Leu Ser
                420                 425                 430
```

-continued

```
Lys Ser Asn Ser Gly Ser Phe Ser Gly Cys Glu Ser Ala Ser Phe Glu
        435                 440                 445

Ser Thr Leu Ser Ser His Cys Thr Asn Ala Gly Val Ala Val Leu Glu
    450                 455                 460

Val Pro Lys Glu Asn Leu Val Leu His Leu Asp Arg Val Lys Arg Tyr
465                 470                 475                 480

Ile Val Glu His Val Asp Leu Gly Ala Tyr Tyr Arg Lys Phe Phe
                485                 490                 495

Tyr Gln Lys Glu His Trp Asn Tyr Phe Gly Ala Asp Glu Asn Leu Gly
            500                 505                 510

Pro Val Ala Val Ser Ile Arg Arg Glu Lys Pro Asp Glu Met Lys Glu
            515                 520                 525

Asn Gly Ser Pro Tyr Asn Tyr Arg Ile Ile Phe Arg Thr Ser Glu Leu
    530                 535                 540

Met Thr Leu Arg Gly Ser Val Leu Glu Asp Ala Ile Pro Ser Thr Ala
545                 550                 555                 560

Lys His Ser Thr Ala Arg Gly Leu Pro Leu Lys Glu Val Leu Glu His
                565                 570                 575

Val Val Pro Glu Leu Asn Val Gln Cys Leu Arg Leu Ala Phe Asn Thr
            580                 585                 590

Pro Lys Val Thr Glu Gln Leu Met Lys Leu Asp Glu Gln Gly Leu Asn
    595                 600                 605

Tyr Gln Gln Lys Val Gly Ile Met Tyr Cys Lys Ala Gly Gln Ser Thr
            610                 615                 620

Glu Glu Glu Met Tyr Asn Asn Glu Ser Ala Gly Pro Ala Phe Glu Glu
625                 630                 635                 640

Phe Leu Gln Leu Leu Gly Glu Arg Val Arg Leu Lys Gly Phe Glu Lys
                645                 650                 655

Tyr Arg Ala Gln Leu Asp Thr Lys Thr Asp Ser Thr Gly Thr His Ser
            660                 665                 670

Leu Tyr Thr Thr Tyr Lys Asp Tyr Glu Ile Met Phe His Val Ser Thr
    675                 680                 685

Met Leu Pro Tyr Thr Pro Asn Asn Lys Gln Gln Leu Leu Arg Lys Arg
690                 695                 700

His Ile Gly Asn Asp Ile Val Thr Ile Val Phe Gln Glu Pro Gly Ala
705                 710                 715                 720

Gln Pro Phe Ser Pro Lys Asn Ile Arg Ser His Phe Gln His Val Phe
                725                 730                 735

Val Ile Val Arg Val His Asn Pro Cys Ser Asp Ser Val Cys Tyr Ser
            740                 745                 750

Val Ala Val Thr Arg Ser Arg Asp Val Pro Ser Phe Gly Pro Pro Ile
    755                 760                 765

Pro Lys Gly Val Thr Phe Pro Lys Ser Asn Val Phe Arg Asp Phe Leu
    770                 775                 780

Leu Ala Lys Val Ile Asn Ala Glu Asn Ala Ala His Lys Ser Glu Lys
785                 790                 795                 800

Phe Arg Ala Met Ala Thr Arg Thr Arg Gln Glu Tyr Leu Lys Asp Leu
                805                 810                 815

Ala Glu Lys Asn Val Thr Asn Thr Pro Ile Asp Pro Ser Gly Lys Phe
            820                 825                 830

Pro Phe Ile Ser Leu Ala Ser Lys Lys Glu Lys Ser Lys Pro Tyr
    835                 840                 845
```

-continued

```
Pro Gly Ala Glu Leu Ser Ser Met Gly Ala Ile Val Trp Ala Val Arg
    850                 855                 860
Ala Glu Asp Tyr Asn Lys Ala Met Glu Leu Asp Cys Leu Leu Gly Ile
865                 870                 875                 880
Ser Asn Glu Phe Ile Val Leu Ile Glu Gln Glu Thr Lys Ser Val Val
                885                 890                 895
Phe Asn Cys Ser Cys Arg Asp Val Ile Gly Trp Thr Ser Thr Asp Thr
            900                 905                 910
Ser Leu Lys Ile Phe Tyr Glu Arg Gly Glu Cys Val Ser Val Gly Ser
            915                 920                 925
Phe Ile Asn Ile Glu Glu Ile Lys Glu Ile Val Lys Arg Leu Gln Phe
        930                 935                 940
Val Ser Lys Gly Cys Glu Ser Val Glu Met Thr Leu Arg Arg Asn Gly
945                 950                 955                 960
Leu Gly Gln Leu Gly Phe His Val Asn Tyr Glu Gly Ile Val Ala Asp
                965                 970                 975
Val Glu Pro Tyr Gly Tyr Ala Trp Gln Ala Gly Leu Arg Gln Gly Ser
            980                 985                 990
Arg Leu Val Glu Ile Cys Lys Val Ala Val Ala Thr Leu Ser His Glu
            995                 1000                1005
Gln Met Ile Asp Leu Leu Arg Thr Ser Val Thr Val Lys Val Val Ile
    1010                1015                1020
Ile Pro Pro His Asp Asp Cys Thr Pro Arg Arg Ser Cys Ser Glu Thr
1025                1030                1035                1040
Tyr Arg Met Pro Val Met Glu Tyr Lys Met Asn Glu Gly Val Ser Tyr
                1045                1050                1055
Glu Phe Lys Phe Pro Phe Arg Asn Asn Asn Lys Trp Gln Arg Asn Ala
            1060                1065                1070
Ser Lys Gly Pro His Ser Pro Gln Val Pro Ser Gln Val Gln Ser Pro
            1075                1080                1085
Met Thr Ser Arg Leu Asn Ala Gly Lys Gly Asp Gly Lys Met Pro Pro
    1090                1095                1100
Pro Glu Arg Ala Ala Asn Ile Pro Arg Ser Ile Ser Ser Asp Gly Arg
1105                1110                1115                1120
Pro Leu Glu Arg Arg Leu Ser Pro Gly Ser Asp Ile Tyr Val Thr Val
            1125                1130                1135
Ser Ser Met Ala Leu Ala Arg Ser Gln Cys Arg Asn Ser Pro Ser Asn
            1140                1145                1150
Leu Ser Ser Ser Ser Asp Thr Gly Ser Val Gly Gly Thr Tyr Arg Gln
            1155                1160                1165
Lys Ser Met Pro Glu Gly Phe Gly Val Ser Arg Arg Ser Pro Ala Ser
    1170                1175                1180
Ile Asp Arg Gln Asn Thr Gln Ser Asp Ile Gly Gly Ser Gly Lys Ser
1185                1190                1195                1200
Thr Pro Ser Trp Gln Arg Ser Glu Asp Ser Ile Ala Asp Gln Met Ala
            1205                1210                1215
Tyr Ser Tyr Arg Gly Pro Gln Asp Phe Asn Ser Phe Val Leu Glu Gln
            1220                1225                1230
His Glu Tyr Thr Glu Pro Thr Cys His Leu Pro Ala Val Ser Lys Val
    1235                1240                1245
Leu Pro Ala Phe Arg Glu Ser Pro Ser Gly Arg Leu Met Arg Gln Asp
1250                1255                1260
Pro Val Val His Leu Ser Pro Asn Lys Gln Gly His Ser Asp Ser His
```

-continued

```
1265                1270                1275                1280

Tyr Ser Ser His Ser Ser Ser Asn Thr Leu Ser Ser Asn Ala Ser Ser
                1285                1290                1295

Ala His Ser Asp Glu Lys Trp Tyr Asp Gly Asp Arg Thr Glu Ser Glu
        1300                1305                1310

Leu Asn Ser Tyr Asn Tyr Leu Gln Gly Thr Ser Ala Asp Ser Gly Ile
        1315                1320                1325

Asp Thr Thr Ser Tyr Gly Pro Ser His Gly Ser Thr Ala Ser Leu Gly
    1330                1335                1340

Ala Ala Thr Ser Ser Pro Arg Ser Gly Pro Gly Lys Glu Lys Val Ala
1345                1350                1355                1360

Pro Leu Trp His Ser Ser Ser Glu Val Ile Ser Met Ala Asp Arg Thr
                1365                1370                1375

Leu Glu Thr Glu Ser His Gly Leu Asp Arg Lys Thr Glu Ser Ser Leu
        1380                1385                1390

Ser Leu Asp Ile His Ser Lys Ser Gln Ala Gly Ser Thr Pro Leu Thr
        1395                1400                1405

Arg Glu Asn Ser Thr Phe Ser Ile Asn Asp Ala Ala Ser His Thr Ser
    1410                1415                1420

Thr Met Ser Ser Arg His Ser Ala Ser Pro Val Val Phe Thr Ser Ala
1425                1430                1435                1440

Arg Ser Ser Pro Lys Glu Glu Leu His Pro Ala Ala Pro Ser Gln Leu
                1445                1450                1455

Ala Pro Ser Phe Ser Ser Ser Ser Ser Ser Ser Gly Pro Arg Ser
        1460                1465                1470

Phe Tyr Pro Arg Gln Gly Ala Thr Ser Lys Tyr Leu Ile Gly Trp Lys
        1475                1480                1485

Lys Pro Glu Gly Thr Ile Asn Ser Val Gly Phe Met Asp Thr Arg Lys
    1490                1495                1500

Arg His Gln Ser Asp Gly Asn Glu Ile Ala His Thr Arg Leu Arg Ala
1505                1510                1515                1520

Ser Thr Arg Asp Leu Arg Ala Ser Pro Lys Pro Thr Ser Lys Ser Thr
                1525                1530                1535

Ile Glu Glu Asp Leu Lys Lys Leu Ile Asp Leu Glu Ser Pro Thr Pro
        1540                1545                1550

Glu Ser Gln Lys Ser Phe Lys Phe His Ala Leu Ser Ser Pro Gln Ser
        1555                1560                1565

Pro Phe Pro Ser Thr Pro Thr Ser Arg Arg Ala Leu His Arg Thr Leu
    1570                1575                1580

Ser Asp Glu Ser Ile Tyr Asn Ser Gln Arg Glu His Phe Phe Thr Ser
1585                1590                1595                1600

Arg Ala Ser Leu Leu Asp Gln Ala Leu Pro Asn Asp Val Leu Phe Ser
                1605                1610                1615

Ser Thr Tyr Pro Ser Leu Pro Lys Ser Leu Pro Leu Arg Arg Pro Ser
        1620                1625                1630

Tyr Thr Leu Gly Met Lys Ser Leu His Gly Glu Phe Ser Ala Ser Asp
        1635                1640                1645

Ser Ser Leu Thr Asp Ile Gln Glu Thr Arg Arg Gln Pro Met Pro Asp
    1650                1655                1660

Pro Gly Leu Met Pro Leu Pro Asp Thr Ala Ala Asp Leu Asp Trp Ser
1665                1670                1675                1680

Asn Leu Val Asp Ala Ala Lys Ala Tyr Glu Val Gln Arg Ala Ser Phe
                1685                1690                1695
```

```
Phe Ala Ala Ser Asp Glu Asn His Arg Pro Leu Ser Ala Ala Ser Asn
        1700                1705                1710

Ser Asp Gln Leu Glu Asp Gln Ala Leu Ala Gln Met Lys Pro Tyr Ser
    1715                1720                1725

Ser Ser Lys Asp Ser Ser Pro Thr Leu Ala Ser Lys Val Asp Gln Leu
    1730                1735                1740

Glu Gly Met Leu Lys Met Leu Arg Glu Asp Leu Lys Lys Glu Lys Glu
1745                1750                1755                1760

Asp Lys Ala His Leu Gln Ala Glu Val Gln His Leu Arg Glu Asp Asn
            1765                1770                1775

Leu Arg Leu Gln Glu Glu Ser Gln Asn Ala Ser Asp Lys Leu Lys Lys
        1780                1785                1790

Phe Thr Glu Trp Val Phe Asn Thr Ile Asp Met Ser
        1795                1800
```

```
<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: PCR primer

<400> SEQUENCE: 5
ccggcggccg cgaaagctgg cagtaccttt gatactgc                              38

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: PCR primer

<400> SEQUENCE: 6
ccggcggccg caggtcctct ataactgtaa gccatctg                              38

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: PCR primer

<400> SEQUENCE: 7
ccggcggccg ctcactctat ctaggtgcaa caccaagttc                            40

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: PCR primer

<400> SEQUENCE: 8
ccggcggccg caatgggaac taagggtaga ctcaaaggag                            40

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: PCR primer

<400> SEQUENCE: 9
```

```
ccggcggccg cggtgtggac gttgtctaaa tttcggtagc c                41
```

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: PCR primer

<400> SEQUENCE: 10

```
ccggcggccg caggtgctct gaggatgctt tctatgg                    37
```

<210> SEQ ID NO 11
<211> LENGTH: 62
<212> TYPE: DNA
<213> ORGANISM: Artificial Sequence
<220> FEATURE:
<223> OTHER INFORMATION: Description of Artificial Sequence: PCR primer

<400> SEQUENCE: 11

```
gcggaattca tggactacaa ggacgacgat gacaagtttc aggacccaca ggagcgaccc    60
ag                                                                  62
```

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: PCR primer

<400> SEQUENCE: 12

```
gccggatcct tacagctggg tttctctacg tgttcttgat ga              42
```

<210> SEQ ID NO 13
<211> LENGTH: 21
<212> TYPE: PRT
<213> ORGANISM: Homo sapiens
<220> FEATURE:
<223> OTHER INFORMATION: E6TP1 beta polypeptide residues 1216-1236

<400> SEQUENCE: 13

```
Ala Tyr Ser Tyr Arg Gly Pro Gln Asp Phe Asn Ser Phe Val Leu Glu
 1               5                  10                  15

Gln His Glu Tyr Thr
            20
```

<210> SEQ ID NO 14
<211> LENGTH: 747
<212> TYPE: PRT
<213> ORGANISM: Homo sapiens
<220> FEATURE:
<223> OTHER INFORMATION: residues 104-850 of GenBank Accession No.
      2389009

<400> SEQUENCE: 14

```
Glu Pro Ala Phe Pro Pro Val Leu Glu Pro Arg Trp Phe Ala His Tyr
 1               5                  10                  15

Asp Val Gln Ser Leu Leu Phe Asp Trp Ala Pro Arg Ser Gln Gly Met
            20                  25                  30

Gly Ser His Ser Glu Ala Ser Ser Gly Thr Leu Ala Ser Ala Glu Asp
        35                  40                  45

Gln Ala Ala Ser Ser Asp Leu Leu His Gly Ala Pro Gly Phe Val Cys
    50                  55                  60
```

-continued

```
Glu Leu Gly Gly Glu Gly Leu Gly Leu Gly Pro Ala Phe Pro
 65                  70                  75                  80

Pro Val Pro Pro Ala Leu Pro Asn Ala Ala Val Ser Ile Leu Glu Glu
             85                  90                      95

Pro Gln Asn Arg Thr Ser Ala Tyr Ser Leu Glu His Ala Asp Leu Gly
             100                 105                 110

Ala Gly Tyr Tyr Arg Lys Tyr Phe Tyr Gly Lys Glu His Gln Asn Phe
             115                 120                 125

Phe Gly Met Asp Glu Ser Leu Gly Pro Val Ala Val Ser Leu Arg Arg
         130                 135                 140

Glu Glu Lys Glu Gly Ser Gly Gly Gly Thr Leu His Ser Tyr Arg Val
145                 150                 155                 160

Ile Val Arg Thr Thr Gln Leu Arg Thr Leu Arg Gly Thr Ile Ser Glu
             165                 170                 175

Asp Ala Leu Pro Pro Gly Pro Pro Arg Gly Leu Ser Pro Arg Lys Leu
             180                 185                 190

Leu Glu His Val Ala Pro Gln Leu Ser Pro Ser Cys Leu Arg Leu Gly
         195                 200                 205

Ser Ala Ser Pro Lys Val Pro Arg Thr Leu Leu Thr Leu Asp Glu Gln
210                 215                     220

Val Leu Ser Phe Gln Arg Lys Val Gly Ile Leu Tyr Cys Arg Ala Gly
225                 230                 235                 240

Gln Gly Ser Glu Glu Glu Met Tyr Asn Asn Gln Glu Ala Gly Pro Ala
             245                 250                 255

Phe Met Gln Phe Leu Thr Leu Leu Gly Asp Val Val Arg Leu Lys Gly
             260                 265                 270

Phe Glu Ser Tyr Arg Ala Gln Leu Asp Thr Lys Thr Asp Ser Thr Gly
         275                 280                 285

Thr His Ser Leu Tyr Thr Thr Tyr Gln Asp His Glu Ile Met Phe His
         290                 295                 300

Val Ser Thr Met Leu Pro Tyr Thr Pro Asn Asn Gln Gln Gln Leu Leu
305                 310                 315                 320

Arg Lys Arg His Ile Gly Asn Asp Ile Val Thr Ile Val Phe Gln Glu
             325                 330                 335

Pro Gly Ser Lys Pro Phe Cys Pro Thr Thr Ile Arg Ser His Phe Gln
             340                 345                 350

His Val Phe Leu Val Val Arg Ala His Thr Pro Cys Thr Pro His Thr
         355                 360                 365

Thr Tyr Arg Val Ala Val Ser Arg Thr Gln Asp Thr Pro Ala Phe Gly
         370                 375                 380

Pro Ala Leu Pro Ala Gly Gly Pro Phe Ala Ala Asn Ala Asp Phe
385                 390                 395                 400

Arg Ala Phe Leu Leu Ala Lys Ala Leu Asn Gly Glu Gln Ala Ala Gly
                 405                 410                 415

His Ala Arg Gln Phe His Ala Met Ala Thr Arg Thr Arg Gln Gln Tyr
             420                 425                 430

Leu Gln Asp Leu Ala Thr Asn Glu Val Thr Thr Thr Ser Leu Asp Ser
             435                 440                 445

Ala Ser Arg Phe Gly Leu Pro Ser Leu Gly Gly Arg Arg Ala Ala
             450                 455                 460

Pro Arg Gly Pro Gly Ala Glu Leu Gln Ala Ala Gly Ser Leu Val Trp
465                 470                 475                 480
```

```
Gly Val Arg Ala Ala Pro Gly Arg Val Ala Ala Gly Ala Gln Ala
                485                 490                 495

Ser Gly Pro Glu Gly Ile Glu Val Pro Cys Leu Leu Gly Ile Ser Ala
                500                 505                 510

Glu Ala Leu Val Leu Val Ala Pro Arg Asp Gly Arg Val Val Phe Asn
                515                 520                 525

Cys Ala Cys Arg Asp Val Leu Ala Trp Thr Phe Ser Glu Gln Gln Leu
                530                 535                 540

Asp Leu Tyr His Gly Arg Gly Glu Ala Ile Thr Leu Arg Phe Asp Gly
545                 550                 555                 560

Ser Pro Gly Gln Ala Val Gly Glu Val Val Ala Arg Leu Gln Leu Val
                565                 570                 575

Ser Arg Gly Cys Glu Thr Arg Glu Leu Ala Leu Pro Arg Asp Gly Gln
                580                 585                 590

Gly Arg Leu Gly Phe Glu Val Asp Ala Glu Gly Phe Val Thr His Val
                595                 600                 605

Glu Arg Phe Thr Phe Ala Glu Thr Ala Gly Leu Arg Pro Gly Ala Arg
                610                 615                 620

Leu Leu Arg Val Cys Gly Gln Thr Leu Pro Ser Leu Arg Pro Glu Ala
625                 630                 635                 640

Ala Ala Gln Leu Leu Arg Ser Ala Pro Lys Val Cys Val Thr Val Leu
                645                 650                 655

Pro Pro Asp Glu Ser Gly Arg Pro Arg Arg Ser Phe Ser Glu Leu Tyr
                660                 665                 670

Thr Leu Ser Leu Gln Glu Pro Ser Arg Arg Gly Ala Pro Asp Pro Val
                675                 680                 685

Gln Asp Glu Val His Gly Val Thr Leu Leu Pro Thr Thr Lys Gln Leu
                690                 695                 700

Leu His Leu Cys Leu Gln Asp Gly Gly Ser Pro Pro Gly Pro Gly Asp
705                 710                 715                 720

Leu Ala Glu Glu Arg Thr Glu Phe Leu His Ser Gln Asn Ser Leu Ser
                725                 730                 735

Pro Arg Ser Ser Leu Ser Asp Glu Ala Pro Val
                740                 745

<210> SEQ ID NO 15
<211> LENGTH: 65
<212> TYPE: PRT
<213> ORGANISM: Homo sapiens
<220> FEATURE:
<223> OTHER INFORMATION: residues 963-1027 of GenBank Accession no.
      2389009

<400> SEQUENCE: 15

Pro Lys Ser Asp Ala Glu Pro Glu Pro Gly Asn Leu Ser Glu Lys Val
1               5                   10                  15

Ser His Leu Glu Ser Met Leu Arg Lys Leu Gln Glu Asp Leu Gln Lys
                20                  25                  30

Glu Lys Ala Asp Arg Ala Ala Leu Glu Glu Glu Val Arg Ser Leu Arg
            35                  40                  45

His Asn Asn Arg Arg Leu Gln Ala Glu Ser Glu Ser Ala Ala Thr Arg
        50                  55                  60

Leu
 65

<210> SEQ ID NO 16
```

-continued

```
<211> LENGTH: 314
<212> TYPE: PRT
<213> ORGANISM: Drosophila melanogaster
<220> FEATURE:
<223> OTHER INFORMATION: residues 87-400 of GenBank Accession no.
      2655096

<400> SEQUENCE: 16
```

Ala Arg Ile Tyr Arg Lys His Phe Leu Gly Lys Glu His Phe Asn Tyr
 1               5                  10                  15

Tyr Ser Leu Asp Thr Ala Leu Gly His Leu Val Phe Ser Leu Lys Tyr
            20                  25                  30

Asp Val Ile Gly Asp Gln Glu His Leu Arg Leu Leu Arg Thr Lys
        35                  40                  45

Cys Arg Thr Tyr His Asp Val Ile Pro Ile Ser Cys Leu Thr Glu Phe
 50                  55                  60

Pro Asn Val Val Gln Met Ala Lys Leu Val Cys Glu Asp Val Asn Val
 65                  70                  75                  80

Asp Arg Phe Tyr Pro Val Leu Tyr Pro Lys Ala Ser Arg Leu Ile Val
                85                  90                  95

Thr Phe Asp Glu His Val Ile Ser Asn Asn Phe Lys Phe Gly Val Ile
            100                 105                 110

Tyr Gln Lys Leu Gly Gln Thr Ser Glu Glu Leu Phe Ser Thr Asn
        115                 120                 125

Glu Glu Ser Pro Ala Phe Val Glu Phe Leu Glu Phe Leu Gly Gln Lys
130                 135                 140

Val Lys Leu Gln Asp Phe Lys Gly Phe Arg Gly Leu Asp Val Thr
145                 150                 155                 160

His Gly Gln Thr Gly Thr Glu Ser Val Tyr Cys Asn Phe Arg Asn Lys
                165                 170                 175

Glu Ile Met Phe His Val Ser Thr Lys Leu Pro Tyr Thr Glu Gly Asp
            180                 185                 190

Ala Gln Gln Leu Gln Arg Lys Arg His Ile Gly Asn Asp Ile Val Ala
        195                 200                 205

Val Val Phe Gln Asp Glu Asn Thr Pro Phe Val Pro Asp Met Ile Ala
210                 215                 220

Ser Asn Phe Leu His Ala Tyr Val Val Gln Ala Glu Gly Gly Gly
225                 230                 235                 240

Pro Asp Gly Pro Leu Tyr Lys Val Ser Val Thr Ala Arg Asp Val
                245                 250                 255

Pro Phe Phe Gly Pro Pro Leu Pro Asp Pro Ala Val Phe Arg Lys Gly
            260                 265                 270

Pro Glu Phe Gln Glu Phe Leu Leu Thr Lys Leu Ile Asn Ala Glu Tyr
        275                 280                 285

Ala Cys Tyr Lys Ala Glu Lys Phe Ala Lys Leu Glu Glu Arg Thr Arg
    290                 295                 300

Ala Ala Leu Leu Glu Thr Leu Tyr Glu Glu
305                 310

```
<210> SEQ ID NO 17
<211> LENGTH: 152
<212> TYPE: PRT
<213> ORGANISM: Homo sapiens
<220> FEATURE:
<223> OTHER INFORMATION: residues 1499-4650 of GenBank Accession no.
      450352

<400> SEQUENCE: 17
```

-continued

```
Asn Glu Ser Gln Ser Phe Glu Arg Ser Val Gln Leu Leu Asp Gln Ile
  1               5                  10                  15

Pro Ser Tyr Asp Thr His Lys Ile Ala Val Leu Tyr Val Gly Glu Gly
             20                  25                  30

Gln Ser Asn Ser Glu Leu Ala Ile Leu Ser Asn Glu His Gly Ser Tyr
             35                  40                  45

Arg Tyr Thr Glu Phe Leu Thr Gly Leu Gly Arg Leu Ile Glu Leu Lys
         50                  55                  60

Asp Cys Gln Pro Asp Lys Val Tyr Leu Gly Gly Leu Asp Val Cys Gly
 65                  70                  75                  80

Glu Asp Gly Gln Phe Thr Tyr Cys Trp His Asp Asp Ile Met Gln Ala
                 85                  90                  95

Val Phe His Ile Ala Thr Leu Met Pro Thr Lys Asp Val Asp Lys His
             100                 105                 110

Arg Cys Asp Lys Lys Arg His Leu Gly Asn Asp Phe Val Ser Ile Val
             115                 120                 125

Tyr Asn Asp Ser Gly Glu Asp Phe Lys Leu Gly Thr Ile Lys Gly Gln
         130                 135                 140

Phe Asn Phe Val His Val Ile Val
145                 150
```